(12) United States Patent
Sugimoto et al.

(10) Patent No.: US 9,724,333 B2
(45) Date of Patent: *Aug. 8, 2017

(54) PYRAZOLE DERIVATIVE

(71) Applicant: GREEN TECH CO., LTD., Mie (JP)

(72) Inventors: Hachiro Sugimoto, Kyoto (JP); Michiaki Okuda, Kyoto (JP); Shinichi Nakayama, Hyogo (JP); Yoshikazu Inoue, Osaka (JP); Yoko Sakata, Osaka (JP); Yuki Fujita, Shiga (JP); Rie Tokizane, Hyogo (JP)

(73) Assignee: GREEN TECH CO., LTD., Mie (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/132,763

(22) Filed: Apr. 19, 2016

(65) Prior Publication Data

US 2016/0228412 A1    Aug. 11, 2016

Related U.S. Application Data

(62) Division of application No. 14/434,185, filed as application No. PCT/JP2013/074998 on Sep. 17, 2013, now Pat. No. 9,321,752.

(30) Foreign Application Priority Data

Oct. 10, 2012 (JP) ................ 2012-225273

(51) Int. Cl.
| | |
|---|---|
| *A61K 31/4155* | (2006.01) |
| *A61K 31/4439* | (2006.01) |
| *A61K 31/444* | (2006.01) |
| *A61K 31/4709* | (2006.01) |
| *A61K 31/496* | (2006.01) |
| *A61K 31/5377* | (2006.01) |
| *A61K 31/551* | (2006.01) |
| *C07D 401/14* | (2006.01) |
| *C07D 231/12* | (2006.01) |
| *C07D 403/06* | (2006.01) |
| *C07D 405/06* | (2006.01) |
| *C07D 403/10* | (2006.01) |
| *C07D 405/10* | (2006.01) |
| *C07D 405/14* | (2006.01) |

(52) U.S. Cl.
CPC ........ *A61K 31/4155* (2013.01); *A61K 31/444* (2013.01); *A61K 31/4439* (2013.01); *A61K 31/4709* (2013.01); *A61K 31/496* (2013.01); *A61K 31/5377* (2013.01); *A61K 31/551* (2013.01); *C07D 231/12* (2013.01); *C07D 401/14* (2013.01); *C07D 403/06* (2013.01); *C07D 403/10* (2013.01); *C07D 405/06* (2013.01); *C07D 405/10* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 4,877,881 A | 10/1989 | Belliotti et al. | |
| 9,321,752 B2 * | 4/2016 | Sugimoto | ............ C07D 401/14 |
| 9,399,635 B2 * | 7/2016 | Sugimoto | ............ C07D 209/12 |
| 2006/0160812 A1 | 7/2006 | Schubert et al. | |
| 2007/0293507 A1 | 12/2007 | Baik et al. | |
| 2010/0048901 A1 | 2/2010 | Takahashi et al. | |
| 2010/0190803 A1 | 7/2010 | Shin et al. | |
| 2010/0197784 A1 | 8/2010 | Lee et al. | |
| 2010/0216859 A1 | 8/2010 | Chen | |
| 2011/0082295 A1 | 4/2011 | Sugimoto et al. | |

FOREIGN PATENT DOCUMENTS

| | | | |
|---|---|---|---|
| CN | 101570512 A | | 11/2009 |
| JP | 63-22079 | | 1/1988 |
| JP | 2005534626 A | | 11/2005 |
| JP | 2008513464 A | | 5/2008 |
| JP | 2008-137914 | * | 6/2008 |
| JP | 2008129132 A | | 6/2008 |
| JP | 2008137914 A | | 6/2008 |
| JP | 2010168344 A | | 8/2010 |
| JP | WO2012/141228 | * | 10/2012 |
| JP | 2012229208 A | | 11/2012 |
| WO | WO-03105751 A2 | | 12/2003 |
| WO | WO-2005006945 A2 | | 1/2005 |

(Continued)

OTHER PUBLICATIONS

Narlawar et al., "Curcumin-Derived Pyrazoles and Isoxazoles: Swiss Army Knives or Blunt Tools for Alzheimer's Disease?" *ChemMedChem*, 3, pp. 165-172 (2008).

(Continued)

*Primary Examiner* — Samantha Shterengarts

(74) *Attorney, Agent, or Firm* — Marshall, Gerstein & Borun LLP

(57) ABSTRACT

Provided is a novel therapeutic means for Alzheimer's disease.

In particular, provided is a compound represented by the following general formula (I):

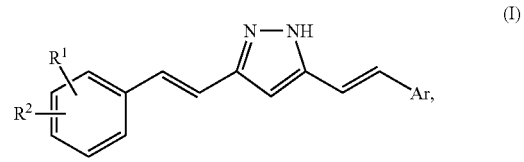

or
a salt thereof.

12 Claims, No Drawings

(56) References Cited

FOREIGN PATENT DOCUMENTS

| WO | WO-2006/033943 | A2 | 3/2006 |
|---|---|---|---|
| WO | WO-2008030072 | A1 | 3/2008 |
| WO | WO-2008066151 | A1 | 6/2008 |
| WO | WO-2009145219 | A1 | 12/2009 |
| WO | WO-2010045395 | A2 | 4/2010 |
| WO | WO-2012141228 | A1 | 10/2012 |

OTHER PUBLICATIONS

Kong et al., "Protectors of Oxidative Stress Inhibit Aβ(1-42) Aggregation in vitro", Bull. Korean Chem. Soc., vol. 23, No. 12, pp. 1773-1777 (2002).

Yang et al., "Protein Structure and Folding: Curcumin Inhibits Formation of Amyloid β Oligomers and Fibrils, Binds Plaques, and Reduces Amyloid in Vivo." J. Biol. Chem., 280 (7), pp. 5892-5901 (2005).

International Search Report and Written Opinion in PCT/JP2013/074998 dated Oct. 22, 2013.

International Search Report in corresponding PCT/JP2012/059944 mailed Apr. 27, 2012.

Li, Q. et al., "Styryl-based compounds as potential in vivo imaging agents for β-amyloid plaques", ChemBioChem, pp. 1679-1687 (2007).

Written Opinion in corresponding PCT/JP2012/059944 mailed Apr. 27, 2012.

Yang et al., "Curcumin Inhibits Formation of Amyloid β Oligomers and Fibrils, Binds Plaques, and Reduces Amyloid in Vivo", J. Biol. Chem., pp. 5892-5901 (2005).

Extended European Search Report for Application No. 13845800.5-1462, dated Feb. 23, 2016.

Amolins M. W. et al., "Synthesis and evaluation of electron-rich curcumin analogues", Bioorganic & Medicinal Chemistry, vol. 17, No. 1. Oct. 29, 2008, pp. 360-367.

Selvam C. et al., "Design, synthesis, biological evaluation and molecular docking of curcumin analogues as antioxidant, cyclooxygenase inhibitory and anti-inflammatory agents", Bioorganic & Medicinal Chemistry Letters, vol. 15, No. 7, 2005, pp. 1793-1797.

Ohtsu H. et al., "Antitumor Agents. 217. Curcumin Analogues as Novel Androgen Receptor Antagonists with Potential as Anti-Prostate Cancer Agents", Journal of Medicinal Chemistry, vol. 45, No. 23, Oct. 12, 2002, pp. 5037-5042.

\* cited by examiner

PYRAZOLE DERIVATIVE

CROSS-REFERENCE TO RELATED APPLICATION

This application is a divisional which claims benefit to U.S. patent application Ser. No. 14/434,185, filed Apr. 8, 2015, which is a National Phase Application of PCT/JP2013/074998, filed Sep. 17, 2013, which claims the benefit of priority from Japanese Patent Application No. 2012-225273, filed Oct. 10, 2012, all of which are incorporated in their entirety by reference herein.

TECHNICAL FIELD

The present invention relates to a novel compound; a tau protein (hereinafter also referred to as tau) aggregation inhibitor, a β-secretase inhibitor, and a μ-amyloid protein (hereinafter also referred to as Aβ) aggregation inhibitor using the same; and a novel pyrazole derivative useful for the prevention or treatment of diseases such as dementia and Alzheimer's disease and a pharmaceutical composition containing the same.

BACKGROUND ART

Senile dementia has become a serious medical and social problem along with the rapid aging of society in recent years and the development of effective anti-dementia drugs has been greatly desired. There are already very many studies on Alzheimer's disease but the cause of the disease has not been clearly defined. Drugs such as acetylcholinesterase inhibitors including donepezil (Aricept (registered trademark)), galantamine (Reminyl) and rivastigmine (Exelon/Rivastach), and NMDA receptor antagonists including memantine hydrochloride (Memary) have been used as Alzheimer's therapeutic drugs. These drugs are very useful as symptomatic therapy but are not drugs for fundamental treatment.

Alzheimer's disease is considered to be caused by aggregation of Aβ, aggregation of tau, and the like. Hence, a substance that inhibits aggregation of these proteins could be used as a fundamental therapeutic drug for Alzheimer's disease.

Yang et al. have reported that curcumin has an Aβ aggregation inhibitory activity, a disaggregation activity on Aβ aggregate, and the like (Non Patent Literature 1). The inventors of the present invention have revealed that curcumin and its derivatives have an inhibitory activity against secretase, which is involved in the generation of Aβ (Patent Literature 1 and 2). Narlawar et al. have synthesized curcumin derivatives by replacing the 1,3-dicarbonyl moiety with a pyrazole ring and reported that these compounds have a tau aggregation inhibitory activity (Non Patent Literature 2).

CITATION LIST

Patent Literature

Patent Literature 1: WO 2008/066151
Patent Literature 2: WO 2009/145219

Non Patent Literature

Non Patent Literature 1: Fusheng Yang et al., J. Biol. Chem. 2005, Feb. 18; 280 (7) 5892-5901
Non Patent Literature 2: Rajeshwar Narlawar et al., ChemMedChem 2008, 3, 165-172

SUMMARY OF INVENTION

Technical Problem

As described in the above literature, a curcumin derivative can be a promising candidate for a fundamental therapeutic drug for Alzheimer's disease. Under this technical background, an object of the present invention is thus to provide a novel therapeutic means for Alzheimer's disease.

Solution to Problem

The inventors succeeded in creating a novel compound based on technical ideas that are distinct from those forming the basis of known compounds and found that the compound has an excellent pharmacological activity. The inventors further conducted extensive studies to complete the present invention.

That is, as a result of the extensive investigations to solve the above problems, the inventors succeeded in synthesizing a curcumin derivative by replacing the 1,3-dicarbonyl moiety of curcumin with a pyrazole ring and replacing at least one of the 4-hydroxy-3-methoxyphenyl groups at both ends with a substituent, and found that this novel compound has a potent tau aggregation inhibitory activity. The inventors also found that this derivative has a high brain penetration and also possesses a β-secretase inhibitory activity and an Aβ aggregation inhibitory activity.

A curcumin derivative in which the 1,3-dicarbonyl moiety of curcumin is replaced with a pyrazole ring is described in Non Patent Literature 2 etc. A curcumin derivative in which one of the 4-hydroxy-3-methoxyphenyl groups at both ends of curcumin is replaced with a substituent is described in Patent Literature 1 and 2, etc. However, the derivative of the present invention which has a pyrazole ring and in which at least one of the 4-hydroxy-3-methoxyphenyl groups at both ends is replaced with a substituent is a novel compound having a chemical structure that is unique to the present invention and distinct from those of compounds disclosed in known literature.

The tau aggregation inhibitory activity of a curcumin derivative is described in Non Patent Literature 2. In this literature, the nitrogen atom at position 1 of the pyrazole ring is replaced with various groups, and the tau aggregation inhibitory activities of the derivatives significantly vary with the groups introduced into the ring. However, no modification was made to the benzene rings at both ends and thus all the synthesized derivatives have the 4-hydroxy-3-methoxyphenyl groups as curcumin does. Therefore, the person skilled in the art who has read Non Patent Literature 2 is expected to consider that the group introduced into the pyrazole ring plays an important role for the tau aggregation inhibitory activity and that the 4-hydroxy-3-methoxyphenyl groups at both ends are irrelevant to the tau aggregation inhibitory activity. Thus the person skilled in the art would not attempt to replace the 4-hydroxy-3-methoxyphenyl groups with a substituent.

That is, the present invention relates to the following.

[1] A compound represented by the following general formula (I):

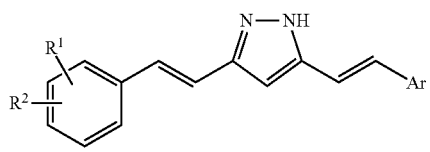

[wherein

R¹ represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, or a carbamoyl group optionally having one or more substituents;

R² represents a group represented by the following general formula (II):

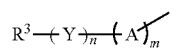

(wherein m and n each represent an integer of 0 or 1,

A represents —O—, —NH—, —S—, —SO— or —SO₂—,

Y represents a $C_{1-6}$ alkylene group, a $C_{2-6}$ alkenylene group or a $C_{2-6}$ alkynylene group, and R³ represents a nitrogen-containing heterocyclic group optionally having one or more substituents, a $C_{1-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents);

R¹ and R² may be joined to form a ring together with the benzene ring; and

Ar represents a homocyclic or heterocyclic group optionally having one or more substituents], or a salt thereof.

[2] The compound according to the above [1] or a salt thereof, wherein m is 1 and A is —O—.

[3] The compound according to the above [2] or a salt thereof, wherein R² is a morpholinomethoxy group, a morpholinoethoxy group, a pyridylmethoxy group, a pyridylethoxy group, a 2-pyrrolidinoethoxy group, a 2-piperidinoethoxy group, a 2-(4-(substituted)piperazino)ethoxy group, or a 2-(1,1-dioxo-1,4-thiazinan-4-yl)ethoxy group.

[4] The compound according to the above [3] or a salt thereof, wherein R² is a morpholinoethoxy group.

[5] The compound according to the above [1] or a salt thereof, wherein R² is a morpholinomethyl group, a (4-(substituted)piperazino)methyl group, a (1,1-dioxo-1,4-thiazinan-4-yl)methyl group, a piperidinomethyl group, a pyrrolidinomethyl group, a 2-morpholinoethyl group, a 2-(4-(substituted)piperazino)ethyl group, a 2-(1,1-dioxo-1,4-thiazinan-4-yl)ethyl group, a 2-piperidinoethyl group, a 2-pyrrolidinoethyl group, or a 2-morpholinoethanesulfonyl group.

[6] The compound according to the above [1] or a salt thereof, wherein R² is a 4-(substituted)piperazino group or a 4-(substituted)-1,4-diazepano group, with the exception of the case where Ar is a homocyclic group optionally having a substituent.

[7] The compound according to any one of the above [1] to [6] or a salt thereof, wherein Ar is a bicyclic group having a benzene skeleton and optionally having one or more substituents.

[8] The compound according to the above [7] or a salt thereof, wherein the bicyclic group having a benzene skeleton is a 1,3-benzodioxole group, a 1,4-benzodioxan-5-yl group, a 1,4-benzodioxan-6-yl group, a 1,4-benzodioxin-2-yl group, a quinolino group, or an indolyl group.

[9] The compound according to any one of the above [1] to [5] or a salt thereof, wherein Ar is a phenyl group optionally having one or more substituents, a pyrrolyl group optionally having one or more substituents, a pyridyl group optionally having one or more substituents, a pyrazyl group optionally having one or more substituents, an imidazolyl group optionally having one or more substituents, or a furyl group optionally having one or more substituents.

[10] The compound according to the above [6] or a salt thereof, wherein Ar is a pyrrolyl group optionally having one or more substituents, a pyridyl group optionally having one or more substituents, a pyrazyl group optionally having one or more substituents, an imidazolyl group optionally having one or more substituents, or a furyl group optionally having one or more substituents.

[11] The compound according to the above [1] or a salt thereof, wherein Ar is represented by the following general formula (III):

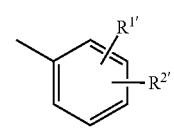

(wherein

R¹' represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, or a carbamoyl group optionally having one or more substituents;

$R^{2'}$ represents a group represented by the following general formula (IV):

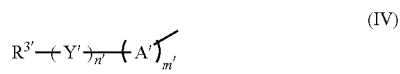

(IV)

(wherein m' and n' each represent an integer of 0 or 1,

A' represents —O—, —NH—, —S—, —SO— or —SO$_2$—,

Y' represents a $C_{1-6}$ alkylene group, a $C_{2-6}$ alkenylene group or a $C_{2-6}$ alkynylene group, and $R^{3'}$ represents a nitrogen-containing heterocyclic group optionally having one or more substituents, a $C_{1-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents), and $R^{1'}$ and $R^{2'}$ may form a ring together with the benzene ring).

[12] A tau aggregation inhibitor comprising the compound according to any one of the above [1] to [11] or a salt thereof as an active ingredient.

[13] A β-secretase inhibitor comprising the compound according to any one of the above [1] to [11] or a salt thereof as an active ingredient.

[14] An Aβ aggregation inhibitor comprising the compound according to any one of the above [1] to [11] or a salt thereof as an active ingredient.

[15] A pharmaceutical composition comprising the compound according to any one of the above [1] to [11] or a salt thereof as an active ingredient.

[16] The pharmaceutical composition according to the above [15] for use in the prevention or treatment of a disease in which tau, β-secretase or Aβ is involved.

[17] Use of the compound according to the above [1] or a salt thereof in the production of a prophylactic or therapeutic preparation for a disease in which tau, β-secretase or Aβ is involved.

[18] The compound according to any one of the above [1] to [11] or a salt thereof for use in the prevention or treatment of a disease in which tau, β-secretase or Aβ is involved.

[19] A method for preventing or treating a disease in which tau, β-secretase or Aβ is involved, the method comprising the step of administering the compound according to the above [1] to a patient.

[20] The pharmaceutical composition according to the above [15] for use in the prevention or treatment of Alzheimer's disease.

[21] Use of the compound according to the above [1] or a salt thereof in the production of a prophylactic or therapeutic preparation for Alzheimer's disease.

[22] The compound according to any one of the above [1] to [11] or a salt thereof for use in the prevention or treatment of Alzheimer's disease.

[23] A method for preventing or treating Alzheimer's disease, the method comprising the step of administering the compound according to the above [1] to a patient.

[24] An oral or parenteral preparation comprising the compound according to any one of the above [1] to [11] or a salt thereof and one or more pharmacologically acceptable carriers.

Advantageous Effects of Invention

The compound of the present invention is remarkably excellent in a tau aggregation inhibitory activity, a β-secretase inhibitory activity, an Aβ aggregation inhibitory activity, and/or the like, and is thus useful as a therapeutic drug for Alzheimer's disease and the like. The compound of the present invention also has a high brain penetration, and thus a highly efficient therapeutic drug can be provided.

DESCRIPTION OF EMBODIMENTS

The present invention will be described in detail below.

In the present invention, the term "halogen atom" means a fluorine atom, a chlorine atom, a bromine atom, and an iodine atom. The term "$C_{1-6}$ alkyl group" means a linear or branched alkyl group of 1 to 6 carbon atoms, and examples thereof include methyl, ethyl, n-propyl, isopropyl, n-butyl, isobutyl, sec-butyl, tert-butyl, n-pentyl, neopentyl, and n-hexyl groups. The term "halo $C_{1-6}$ alkyl group" means a linear or branched 1- to 6-carbon alkyl group substituted with one or more halogen atoms that may be the same or different, and examples thereof include trifluoromethyl, difluoromethyl, perfluoroethyl, hexafluoroisopropyl, perfluoroisopropyl, chloromethyl, bromomethyl, 1-bromoethyl, and 2,3-dibromopropyl groups.

The term "$C_{1-6}$ alkoxy group" means a linear or branched alkoxy group of 1 to 6 carbon atoms, and examples thereof include methoxy, ethoxy, n-propoxy, isopropoxy, n-butoxy, sec-butoxy, tert-butoxy, n-pentyloxy, isopentyloxy, neopentyloxy, and n-hexyloxy groups. The term "halo $C_{1-6}$ alkoxy group" means a linear or branched 1- to 6-carbon alkoxy group substituted with one or more halogen atoms that may be the same or different, and examples thereof include trifluoromethoxy, difluoromethoxy, perfluoroethoxy, perfluoroisopropoxy, chloromethoxy, bromomethoxy, 1-bromoethoxy, and 2,3-dibromopropoxy groups.

The term "$C_{1-6}$ acyl group" means a linear or branched acyl group of 1 to 6 carbon atoms, and examples thereof include formyl, acetyl, propionyl, butyryl, 2-methylpropionyl, pivaloyl, pentanoyl, 3-methylbutyryl, and hexanoyl groups. The term "halo $C_{1-6}$ acyl group" means a linear or branched 1- to 6-carbon acyl group substituted with one or more halogen atoms that may be the same or different, and examples thereof include chloroformyl, bromoformyl, dichloroacetyl, dibromoacetyl, and trifluoroacetyl groups.

The term "$C_{1-6}$ alkylsulfonyl group" means a linear or branched alkylsulfonyl group of 1 to 6 carbon atoms, and examples thereof include methylsulfonyl, ethylsulfonyl, n-propylsulfonyl, isopropylsulfonyl, n-butylsulfonyl, sec-butylsulfonyl, tert-butylsulfonyl, n-pentylsulfonyl, isopentylsulfonyl, and n-hexylsulfonyl groups. The term "halo $C_{1-6}$ alkylsulfonyl group" means a linear or branched 1- to 6-carbon alkylsulfonyl group substituted with one or more halogen atoms that may be the same or different, and examples thereof include trifluoromethylsulfonyl, difluoromethylsulfonyl, perfluoroethylsulfonyl, perfluoroisopropylsulfonyl, chloromethylsulfonyl, bromomethylsulfonyl, 1-bromoethylsulfonyl, and 2,3-dibromopropylsulfonyl groups.

The term "mono- or di($C_{1-6}$ alkyl)amino group" means an amino group mono- or di-substituted with the above $C_{1-6}$ alkyl group, and examples thereof include methylamino, ethylamino, propylamino, isopropylamino, butylamino, sec-butylamino, tert-butylamino, dimethylamino, diethylamino, ethylmethylamino, dipropylamino, methylpropylamino, and diisopropylamino groups. The term "$C_{1-6}$ alkylthio group"

means a linear or branched alkylthio group of 1 to 6 carbon atoms, and examples thereof include methylthio, ethylthio, n-propylthio, isopropylthio, n-butylthio, sec-butylthio, tert-butylthio, n-pentylthio, isopentylthio, and n-hexylthio groups. The term "$C_{1-6}$ acylamino group" means an amino group substituted with the above $C_{1-6}$ acyl group, and examples thereof include acetylamino and propionylamino groups.

The term "$C_{2-6}$ alkenyl group" means a linear or branched alkenyl group of 2 to 6 carbon atoms, and examples thereof include vinyl, propenyl, and butenyl groups. The term "$C_{2-6}$ alkenyloxy group" means a linear or branched alkenyloxy group of 2 to 6 carbon atoms, and examples thereof include propenyloxy, butenyloxy, and pentenyloxy groups. The term "mono- or di($C_{2-6}$ alkenyl)amino group" means an alkenyl amino group mono- or di-substituted with the above $C_{2-6}$ alkenyl group, and examples thereof include vinylamino, propenylamino, butenylamino, and divinylamino groups.

The term "$C_{2-6}$ alkenylthio group" means a linear or branched alkenylthio group of 2 to 6 carbon atoms, and examples thereof include vinylthio, 1-propenylthio, isopropenylthio, 1-butenylthio, 2-butenylthio, and 2-methylallylthio groups. The term "nitrogen-containing heterocyclic group" means a saturated or unsaturated heterocyclic group containing one or more nitrogen atoms and optionally containing one or more oxygen and/or sulfur atoms, and examples thereof include pyridyl, pyrimidyl, pyrazyl, morpholino, 4-(substituted)piperazino (e.g., 4-methylpiperazino etc.), 1,1-dioxo-1,4-thiazinan-4-yl, piperidino, pyrrolidino, thiazolyl, azepan-1-yl, and 4-(substituted)-1,4-diazepano (e.g., 4-methyl-1,4-diazepano) groups.

The present invention relates to a compound represented by the following general formula (I):

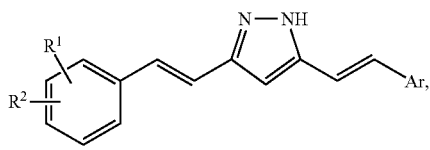

(I)

and
a salt thereof.

In the above general formula (I), $R^1$ represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, a carbamoyl group optionally having one or more substituents, or the like.

The substituents in $R^1$ are not particularly limited as long as the effects of the present invention are not impaired, and examples thereof include a halogen atom, a hydroxy group, a nitro group, an amino group, a morpholino group, and a pyridyl group. $R^1$ is preferably a hydroxy group, a $C_{1-6}$ alkyl group optionally having one or more substituents, a $C_{1-6}$ alkoxy group optionally having one or more substituents, or the like, and is more preferably hydroxy, methoxy, ethoxy, morpholinomethoxy, morpholinoethoxy, pyridylmethoxy, or pyridylethoxy group, or the like. The position of $R^1$ on the benzene ring is not particularly limited as long as the effects of the present invention are not impaired, but when the position of the carbon atom bound to the pyrazole ring via the vinyl group is assigned position 1, the position of $R^1$ on the benzene ring is preferably position 2 or 3, more preferably position 2.

In the above general formula (I), $R^2$ represents a group represented by the following general formula (II):

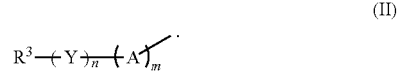

(II)

In the above general formula (II), m and n each represent an integer of 0 or 1. A represents —O—, —NH—, —S—, —SO—, —SO$_2$—, or the like, and preferably represents —O—, —SO$_2$—, or the like. Y represents a $C_{1-6}$ alkylene group, a $C_{2-6}$ alkenylene group, a $C_{2-6}$ alkynylene group, or the like, and preferably represents a methylene group, an ethylene group, or the like. $R^3$ represents a nitrogen-containing heterocyclic group optionally having one or more substituents, a $C_{1-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents.

The substituents in $R^3$ in the above general formula (II) are not particularly limited as long as the effects of the present invention are not impaired. In cases where $R^3$ is a nitrogen-containing heterocyclic group, the substituents are preferably a halogen atom, a hydroxy group, a nitro group, an amino group, a $C_{1-6}$ alkyl group, a halo $C_{1-6}$ alkyl group, a $C_{1-6}$ alkoxy group, a halo $C_{1-6}$ alkoxy group, a $C_{1-6}$ acyl group, a halo $C_{1-6}$ acyl group, a $C_{1-6}$ alkylsulfonyl group, a halo $C_{1-6}$ alkylsulfonyl group, or the like. In cases where $R^3$ is a $C_{1-6}$ alkoxy group, the substituents are preferably a methoxy group, an ethoxy group, a 2-methoxyethoxy group, or the like. In cases where $R^3$ is a mono- or di($C_{1-6}$ alkyl)amino group or a mono- or di(alkenyl)amino group, the substituents are preferably a $C_{1-6}$ alkoxy group, a halo $C_{1-6}$ alkoxy group, a $C_{1-6}$ alkylsulfonyl group, a halo $C_{1-6}$ alkylsulfonyl group, or the like. In cases where $R^3$ is a carbamoyl group, the substituents are preferably a $C_{1-6}$ alkyl group, a $C_{1-6}$ alkoxy group, or the like.

Preferred specific examples of the group represented by $R^3$ include pyridyl, pyrimidyl, pyrazyl, morpholino, 4-(substituted)piperazino (e.g., 4-methylpiperazino), 4-(substituted)-1,4-diazepano (e.g., 4-methyl-1,4-diazepano), 1,1-dioxo-1,4-thiazinan-4-yl, piperidino, pyrrolidino, thiazolyl, methoxy, ethoxy, propoxy, dimethylamino, diethylamino, isopropylamino, N,N-bis(2-methoxyethyl)amino, N-2-methoxyethyl-N-methylamino, N,N-bis(2-methylsulfonylethyl)amino, N-methyl-N-(2-methylsulfonylethyl)amino, and dimethylcarbamoyl groups.

Particularly preferred specific examples of the group represented by $R^2$ include morpholinoethoxy, morpholinomethoxy, pyridylmethoxy, pyridylethoxy, 2-pyrrolidinoethoxy, 2-piperidinoethoxy, 2-(4-(substituted)piperazino) ethoxy, 2-(1,1-dioxo-1,4-thiazinan-4-yl)ethoxy, morpholinomethyl, (4-(substituted)piperazino)methyl, (1,1-dioxo-1,4-thiazinan-4-yl)methyl, piperidinomethyl, pyrrolidinomethyl, 2-morpholinoethyl, 2-(4-(substituted)piperazino)ethyl, 2-(1,1-dioxo-1,4-thiazinan-4-yl)ethyl, 2-piperidinoethyl, 2-pyrrolidinoethyl, 2-morpholinoethanesulfonyl, methoxymethoxy, methoxyethoxy, methoxymethyl, methoxyethyl, dimethylamino, diethylamino, isopropylamino, N,N-bis(2-methoxyethyl)amino, N-2-methoxyethyl-N-methylamino, N,N-bis(2-methylsulfonylethyl)amino, N-methyl-N-(2-methylsulfonylethyl)amino, dimethylaminomethyl, diethylaminomethyl, N,N-bis(2-methoxyethyl)aminomethyl, dimethylaminoethoxy, 4-(substituted)piperazino, 4-(substituted)-1,4-diazepano, and dimethylcarbamoylethoxy groups. The substituents represented by the term "substituted" enclosed in the parentheses are not particularly limited as long as the present invention is not impaired, but are preferably a hydrogen atom, a $C_{1-6}$ alkyl group, or the like, and are particularly preferably a hydrogen atom, a methyl group, an ethyl group, an isopropyl group, or the like. The position of $R^2$ on the benzene ring is not particularly limited as long as the effects of the present invention are not impaired, but when the position of the carbon atom bound to the pyrazole ring via the vinyl group is assigned position 1, the position of $R^2$ on the benzene ring is preferably position 3 or 4, more preferably position 4.

In the above general formula (I), $R^1$ and $R^2$ may be joined together to form a ring. In this case, $R^1$ and $R^2$ form a fused ring or the like together with the benzene ring to which $R^1$ and $R^2$ are attached. Examples of the fused ring include a 1,3-benzodioxole group optionally having one or more substituents, a 1,4-benzodioxan-5-yl group optionally having one or more substituents, a 1,4-benzodioxan-6-yl group optionally having one or more substituents, a 1,4-benzodioxin-6-yl group optionally having one or more substituents, a 1,4-benzodioxin-2-yl group optionally having one or more substituents, a quinolino group optionally having one or more substituents, an isoquinolino group optionally having one or more substituents, a quinoxalino group optionally having one or more substituents, and an indolyl group optionally having one or more substituents.

The substituents in the above fused rings are not particularly limited and examples thereof include those exemplified above for $R^1$, $R^2$ and $R^3$.

In the above general formula (I), Ar represents a homocyclic or heterocyclic group optionally having one or more substituents. The substituents are not particularly limited as long as the effects of the present invention are not impaired. Preferred examples thereof include a halogen atom, a hydroxy group, a nitro group, an amino group, a $C_{1-6}$ alkyl group, a halo $C_{1-6}$ alkyl group, a $C_{1-6}$ alkoxy group, a halo $C_{1-6}$ alkoxy group, a $C_{1-6}$ acyl group, a halo $C_{1-6}$ acyl group, a $C_{1-6}$ alkylsulfonyl group, and a halo $C_{1-6}$ alkylsulfonyl group, and particularly preferred examples thereof include amino, hydroxy, methyl, ethyl, methoxy, and ethoxy groups. Preferred examples of the homocyclic or heterocyclic group include a monocyclic group such as phenyl, pyrrolyl, imidazolyl, furyl, pyridyl, and pyrazyl groups, and a bicyclic group having a benzene skeleton.

Preferred examples of the bicyclic group having a benzene skeleton include 1,3-benzodioxole, 1,4-benzodioxan-5-yl, 1,4-benzodioxan-6-yl, 1,4-benzodioxin-6-yl, 1,4-benzodioxin-2-yl, quinolino, isoquinolino, quinoxalino, and indolyl groups. Particularly preferred examples of the indolyl group optionally having one or more substituents include a 1-methylindolyl group.

In cases where Ar is a phenyl group optionally having one or more substituents, Ar is preferably a substituent represented by, for example, the following general formula (III):

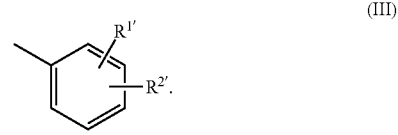

(III)

In the above general formula (I), $R^{1'}$ represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, a carbamoyl group optionally having one or more substituents, or the like.

The substituents in $R^{1'}$ are not particularly limited as long as the effects of the present invention are not impaired, and examples thereof include a halogen atom, a hydroxy group, a nitro group, an amino group, a morpholino group, and a pyridyl group. $R^{1'}$ is preferably a hydroxy group, a $C_{1-6}$ alkyl group optionally having one or more substituents, a $C_{1-6}$ alkoxy group optionally having one or more substituents, or the like, and is more preferably hydroxy, methoxy, ethoxy, morpholinomethoxy, morpholinoethoxy, pyridylmethoxy, or pyridylethoxy group, or the like. The position of $R^{1'}$ on the benzene ring is not particularly limited as long as the effects of the present invention are not impaired, but when the position of the carbon atom bound to the pyrazole ring via the vinyl group is assigned position 1, the position of $R^{1'}$ on the benzene ring is preferably position 2 or 3, more preferably position 2.

In the above general formula (III), $R^{2'}$ represents a group represented by the following general formula (IV):

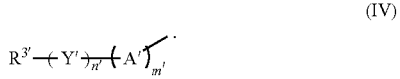

(IV)

In the above general formula (IV), m' and n' each represent an integer of 0 or 1. A' represents —O—, —NH—, —S—, —SO—, —SO$_2$—, or the like, and preferably represents —O—, —SO$_2$—, or the like. Y' represents a $C_{1-6}$ alkylene group, a $C_{2-6}$ alkenylene group, a $C_{2-6}$ alkynylene group, or the like, and preferably represents a methylene group, an ethylene group, or the like. $R^{3'}$ represents a nitrogen-containing heterocyclic group optionally having one or more substituents, a $C_{1-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents.

The substituents in $R^{3'}$ in the above general formula (IV) are not particularly limited as long as the effects of the present invention are not impaired. In cases where $R^{3'}$ is a nitrogen-containing heterocyclic group, the substituents are preferably a halogen atom, a hydroxy group, a nitro group, an amino group, a $C_{1-6}$ alkyl group, a halo $C_{1-6}$ alkyl group, a $C_{1-6}$ alkoxy group, a halo $C_{1-6}$ alkoxy group, a $C_{1-6}$ acyl group, a halo $C_{1-6}$ acyl group, a $C_{1-6}$ alkylsulfonyl group, a halo $C_{1-6}$ alkylsulfonyl group, or the like. In cases where $R^{3'}$ is a $C_{1-6}$ alkoxy group, the substituents are preferably a methoxy group, an ethoxy group, a 2-methoxyethoxy group, or the like. In cases where $R^{3'}$ is a mono- or di($C_{1-6}$ alkyl)amino group or a mono- or di(alkenyl)amino group, the substituents are preferably a $C_{1-6}$ alkoxy group, a halo $C_{1-6}$ alkoxy group, a $C_{1-6}$ alkylsulfonyl group, a halo $C_{1-6}$ alkylsulfonyl group, or the like. In cases where $R^{3'}$ is a carbamoyl group, the substituents are preferably a $C_{1-6}$ alkyl group, a $C_{1-6}$ alkoxy group, or the like.

Preferred specific examples of the group represented by $R^{3'}$ include pyridyl, pyrimidyl, pyrazyl, morpholino, 4-(substituted)piperazino (e.g., 4-methylpiperazino), 1,1-dioxo-1,4-thiazinan-4-yl, piperidino, pyrrolidino, thiazolyl, methoxy, ethoxy, propoxy, dimethylamino, diethylamino, isopropylamino, N,N-bis(2-methoxyethyl)amino, N-2-methoxyethyl-N-methylamino, N,N-bis(2-methylsulfonylethyl)amino, N-methyl-N-(2-methylsulfonylethyl)amino, and dimethylcarbamoyl groups.

Particularly preferred specific examples of the group represented by $R^{2'}$ include morpholinoethoxy, morpholinomethoxy, pyridylmethoxy, pyridylethoxy, 2-pyrrolidinoethoxy, 2-piperidinoethoxy, 2-(4-(substituted)piperazino)ethoxy, 2-(1,1-dioxo-1,4-thiazinan-4-yl)ethoxy, morpholinomethyl, (4-(substituted)piperazino)methyl, (1,1-dioxo-1,4-thiazinan-4-yl)methyl, piperidinomethyl, pyrrolidinomethyl, 2-morpholinoethyl, 2-(4-(substituted)piperazino)ethyl, 2-(1,1-dioxo-1,4-thiazinan-4-yl)ethyl, 2-piperidinoethyl, 2-pyrrolidinoethyl, 2-morpholinoethanesulfonyl, methoxymethoxy, methoxyethoxy, methoxymethyl, methoxyethyl, dimethylamino, diethylamino, isopropylamino, N,N-bis(2-methoxyethyl)amino, N-2-methoxyethyl-N-methylamino, N,N-bis(2-methylsulfonylethyl)amino, N-methyl-N-(2-methylsulfonylethyl)amino, dimethylaminomethyl, diethylaminomethyl, N,N-bis(2-methoxyethyl)aminomethyl, dimethylaminoethoxy, and dimethylcarbamoylethoxy groups. The substituents represented by the term "substituted" enclosed in the parentheses are not particularly limited as long as the present invention is not impaired, but are preferably a hydrogen atom, a $C_{1-6}$ alkyl group, or the like, and are particularly preferably a hydrogen atom, a methyl group, an ethyl group, an isopropyl group, or the like. The position of $R^{2'}$ on the benzene ring is not particularly limited as long as the effects of the present invention are not impaired, but when the position of the carbon atom bound to the pyrazole ring via the vinyl group is assigned position 1, the position of $R^{2'}$ on the benzene ring is preferably position 3 or 4, more preferably position 4.

In the above general formula (III), $R^{1'}$ and $R^{2'}$ may be joined together to form a ring. In this case, $R^{1'}$ and $R^{2'}$ form a fused ring or the like together with the benzene ring to which $R^{1'}$ and $R^{2'}$ are attached. Examples of the fused ring include those exemplified above for the bicyclic group having a benzene skeleton.

The substituent represented by the general formula (III) may be the same as or different from the phenyl group substituted with $R^1$ and $R^2$ in the general formula (I). When they are the same, the compound or a salt thereof is easier to synthesize and is thus industrially preferable.

In the general formula (I), in cases where $R^2$ is a morpholinomethoxy, morpholinoethoxy or pyridylmethoxy group, Ar is particularly preferably, for example, a phenyl group optionally having one or more substituents (e.g., a morpholinomethoxy phenyl group, a dimethylcarbamoylmethoxy phenyl group, a dimethoxyphenyl group, or the like), a pyrrolyl group optionally having one or more substituents, or a bicyclic group having a benzene skeleton and optionally having one or more substituents (e.g., a 1,3-benzodioxole group, a 1,4-benzodioxan-6-yl group, an indolyl group, a 1-methylindolyl group, or the like). In cases where $R^2$ is a pyridylmethoxy group, Ar is particularly preferably, for example, a pyrrolyl group optionally having one or more substituents, or a bicyclic group having a benzene skeleton (e.g., a 1-methylindolyl group or the like). Preferably, $R^1$, $R^2$ and/or Ar are basic groups so that the compound or a salt thereof is excellent in water solubility and therefore can readily undergo oral absorption and the like.

A salt of the compound represented by the general formula (I) is also encompassed in the present invention. The salt is preferably a pharmacologically acceptable salt and examples thereof include hydrohalic acid salts such as hydrofluoride, hydrochloride, hydrobromide, and hydroiodide; inorganic acid salts such as sulfate, nitrate, perchlorate, phosphate, carbonate, and bicarbonate; organic carboxylic acid salts such as acetate, oxalate, maleate, tartrate, and fumarate; organic sulfonic acid salts such as methanesulfonate, trifluoromethanesulfonate, ethanesulfonate, benzenesulfonate, toluenesulfonate, and camphorsulfonate; amino acid salts such as aspartate and glutamate; amine salts such as trimethylamine salt, triethylamine salt, procaine salt, pyridine salt, and phenethylbenzylamine salt; alkali metal salts such as sodium salt and potassium salt; alkaline earth metal salts such as magnesium salt and calcium salt; etc. In view of the water solubility, oral absorbability, efficacy, and the like, preferred are hydrochloride and oxalate.

The compound represented by the general formula (I) can be produced by known methods described in, for example, Rajeshwar Narlawar et al., ChemMedChem 2008, 3, 165-172, WO 2008/066151, WO 2009/145219, or the like, or by any combination of the methods described in the literature, or by a method known per se or an equivalent method thereto. Specifically, the compound can be produced by, for example, the following Steps 1 and 2, but the production method is not limited thereto.

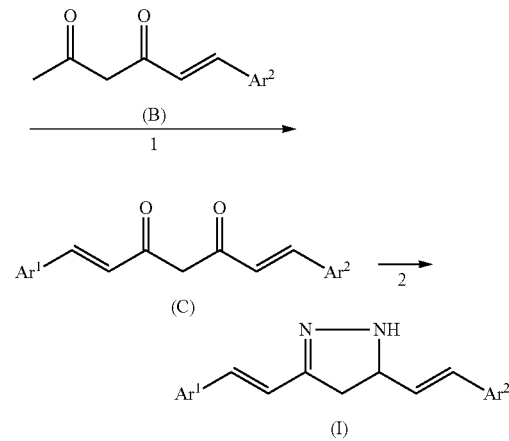

$Ar^1$ in the above formula is either the phenyl ring substituted with $R^1$ and $R^2$ or a ring represented by Ar in the compound represented by the general formula (I) of the present invention, and $Ar^2$ is the other one. In Step 1, an aldehyde represented by the general formula (A) is allowed to react with a compound represented by the general formula (B) in the presence of a solvent and a catalyst to give a diketone represented by the general formula (C).

The solvent used in the reaction is not particularly limited as long as it does not inhibit the reaction, and examples thereof include ethyl acetate, N,N-dimethylacetamide, N,N-dimethylformamide, 1-methyl-2-pyrrolidone, dimethylsulfoxide, tetrahydrofuran, acetonitrile, etc. These solvents may be used alone or in combination of two or more kinds thereof at a given mixing ratio.

The catalyst used in the reaction is also not particularly limited. Examples thereof include bases such as a primary amine and a secondary amine, and specific examples thereof include n-butylamine, ethanolamine, piperidine, morpholine, etc.

In Step 1, a water scavenger may be added in order to capture the water produced by the reaction. Examples of the water scavenger include an alkyl borate, an alkyl phosphate, an orthoester, etc., and specific examples thereof include trimethyl orthoformate and tri-n-butyl borate.

In Step 1, the quantitative ratio of the aldehyde represented by the general formula (A) and the compound represented by the general formula (B) is not particularly limited as long as the reaction proceeds. However, in view of the reaction efficiency and the like, the amount of the compound is preferably 0.5 to 10 mol, more preferably 0.5 to 2 mol, relative to 1 mol of the aldehyde.

In Step 1, the reaction temperature is not particularly limited as long as the reaction proceeds. However, in view of the reaction efficiency and the like, the reaction temperature is preferably 0 to 200° C., more preferably 50 to 100° C.

In Step 1, the reaction duration is not particularly limited as long as the reaction proceeds. However, in view of the production efficiency and the like, the reaction duration is preferably 0.5 to 48 hours, more preferably 1 to 24 hours.

The aldehyde represented by the general formula (A) and the compound represented by the general formula (B) that are used in Step 1 may be commercially available products or those synthesized by a known method (for example, the method described in WO 2008/066151 or WO 2009/145219) or other methods.

In Step 2, a diketone represented by the general formula (C) is allowed to react with a hydrazine in the presence of a solvent to give a compound represented by the general formula (I).

The hydrazine used in the reaction is not particularly limited and examples thereof include hydrazine monohydrate, hydrazine aqueous solution, anhydrous hydrazine, hydrazine acetate, hydrazine monohydrochloride, hydrazine dihydrochloride, a derivative thereof, etc.

The solvent used in the reaction is not particularly limited as long as it does not inhibit the reaction and examples thereof include protic solvents such as acetic acid, methanol, ethanol, and water; non-protic solvents such as ethyl acetate, toluene, tetrahydrofuran, methylene chloride, chloroform, etc. These solvents may be used alone or, if desired, in combination of two or more kinds thereof at a given mixing ratio.

In Step 2, the quantitative ratio of the diketone represented by the general formula (C) and the hydrazine is not particularly limited as long as the reaction proceeds. However, in view of the reaction efficiency and the like, the amount of the hydrazine is preferably 1 to 50 mol, more preferably 2 to 10 mol, relative to 1 mol of the diketone.

In Step 2, the reaction temperature is not particularly limited as long as the reaction proceeds. However, in view of the reaction efficiency and the like, the reaction temperature is preferably 20 to 120° C., more preferably 50 to 80° C.

In Step 2, the reaction duration is not particularly limited as long as the reaction proceeds. However, in view of the production efficiency and the like, the reaction duration is preferably 0.2 to 24 hours, more preferably 0.5 to 6 hours.

The compound of the present invention may be administered to a subject, alone or in combination with one or more of other compounds of the present invention, or with one or more compounds other than the compounds of the present invention. The compound of the present invention may be administered as a preparation or pharmaceutical composition comprising one or more pharmacologically acceptable carriers. The effective dosage of the compound of the present invention as an active ingredient and frequency of administration may vary with the dosage form, the age, body weight, symptoms, etc. of the patient, and the like, but the daily dosage is usually about 0.01 to 100 mg/kg, more preferably about 1 to 50 mg/kg.

The subject is not particularly limited and examples thereof include mammals such as a human, a monkey, a hamadryas baboon, a chimpanzee, a mouse, a rat, a guinea pig, a hamster, a rabbit, a cat, a dog, a sheep, a goat, a pig and a cattle.

The route of administration of the preparation or pharmaceutical composition comprising the compound of the present invention as an active ingredient is not particularly limited, and the preparation or pharmaceutical composition may be administered orally or parenterally by a usual method. Examples of the parenteral administration include rectal administration, nasal administration, transpulmonary administration, dermal administration, and injection administration (e.g., intravenous administration, intraspinal administration, epidural administration, intramuscular administration, subcutaneous administration, intraperitoneal administration, intraarterial administration, intraarticular administration, intracardiac administration, intracystic administration, intracutaneous administration, intralesional administration, intraocular administration, intrathoracic administration, subarachnoid administration, intrauterine administration, intraventricular administration, etc.).

The form of the preparation or pharmaceutical composition comprising the compound of the present invention as an active ingredient is not particularly limited, and examples thereof include oral or parenteral preparations such as tablets, powders, granules, capsules, oral solutions, emulsions, elixirs, lemonades, suspensions, syrups, oromucosal tablets, oral jellies, inhalations, suppositories, injections, ointments, ophthalmic ointments, ophthalmic preparations, nasal preparations, ear preparations, patches, solutions for external application.

The dosage of the preparation or pharmaceutical composition of the present invention can be determined as appropriate depending on the severity of the symptom, the age, sex, and body weight of the patient, the route of administration, the type of the salt, the specific disease, etc.

Since the compound of the present invention has a tau aggregation inhibitory activity, a β-secretase inhibitory activity, and/or an Aβ aggregation inhibitory activity, the compound of the present invention is effective in preventing and treating diseases in which tau, β-secretase or Aβ is involved, such as Alzheimer's disease (familial Alzheimer's disease and sporadic Alzheimer's disease), senile dementia, Down syndrome, Parkinson's disease, Creutzfeldt-Jakob disease, amyotrophic lateral sclerosis, diabetic neuropathy, Huntington's chorea, multiple sclerosis, etc. Among these nervous diseases, the compound of the present invention is especially effective in preventing and treating Alzheimer's disease.

The compound of the present invention can be formulated by a commonly used method into dosage forms such as tablets, powders, granules, capsules, oral solutions, emulsions, elixirs, lemonades, suspensions, syrups, oromucosal tablets, oral jellies, inhalations, suppositories, injections, ointments, ophthalmic ointments, ophthalmic preparations, nasal preparations, ear preparations, patches, solutions for external application, etc. For the formulation into such dosage forms, excipients, binders, lubricants, colorants and flavor modifiers that are usually used for the formulation of medicines can be used, and as needed stabilizers, emulsifiers, absorption enhancers, surfactants, pH adjusters, preservatives, antioxidants, and/or the like can also be used. Thus, ingredients that are usually used as raw materials of a pharmaceutical preparation may be mixed with the compound and formulated into a dosage form by a conventional method.

For example, in the production of oral preparations, a crystalline or amorphous compound of the present invention is mixed with excipients, and as needed with additives such as binders, disintegrators, lubricants, colorants, flavor modifiers, etc., and formed into powders, fine granules, granules, tablets, coated tablets, capsules, etc. by a conventional method. Examples of the additives include animal and vegetable fats and oils such as soybean oil, beef tallow, and synthetic glyceride; hydrocarbons such as liquid paraffin, squalane, and hard paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid ester, sorbitan fatty acid ester, glycerin fatty acid ester, polyoxyethylene sorbitan fatty acid ester, polyoxyethylene hardened castor oil, and polyoxyethylene-polyoxypropylene block copolymer; water soluble polymers such as hydroxyethyl cellulose, hydroxypropyl methylcellulose, hydroxypropyl methylcellulose phthalate, polyacrylate, carboxy vinyl polymer, polyethylene glycol, polyvinylpyrrolidone, and methylcellulose; lower alcohols such as ethanol and isopropanol; polyalcohols such as glycerin, propylene glycol, dipropylene glycol, and sorbitol; sugars such as glucose and sucrose; inorganic powders such as anhydrous silicic acid, magnesium aluminum silicate, and aluminium silicate; purified water; etc.

Examples of the excipients include lactose, corn starch, saccharose, glucose, mannitol, sorbitol, crystalline cellulose, silicon dioxide, etc. Examples of the binders include polyvinyl alcohol, polyvinyl ether, methylcellulose, ethylcellulose, gum arabic, tragacanth, gelatin, shellac, hydroxypropyl methylcellulose, hydroxypropyl cellulose, polyvinylpyrrolidone, polypropylene glycol-polyoxyethylene block polymer, meglumine, etc. Examples of the disintegrators include starch, agar, gelatin powder, crystalline cellulose, calcium carbonate, sodium bicarbonate, calcium citrate, dextrin, pectin, carboxymethyl cellulose calcium, etc. Examples of the lubricants include magnesium stearate, talc, polyethylene glycol, silica, hydrogenated vegetable oil, etc. Examples of the colorants include a colorant that is approved as additives to a medicine, etc. Examples of the flavor modifiers include cocoa powder, menthol, aromatic powder, mentha oil, borneol, cinnamon powder, etc.

Needless to say, in the production of the tablets or granules, coating of the tablets or granules with a sugar or the like may be performed as needed. In the production of solutions such as syrups, emulsions, elixirs, lemonades, suspensions, and injections, the compound of the present invention can be mixed as needed with further additives such as pH adjusters, solubilizers, emulsifiers, disintegrators, isotonic agents, solubilization assisting agents, stabilizers, and the like, and formed into such solutions by a conventional method.

In the production of external medicines, the production method is not limited and the production can be carried out by a conventional method. That is, for the formulation of external medicines, various types of raw materials that are usually used for medicines, quasi drugs, cosmetics, or the like can be used as a base ingredient. Specific examples of the base ingredients to be used include animal and vegetable oils, mineral oils, ester oils, waxes, higher alcohols, fatty acids, silicone oils, surfactants, phospholipids, alcohols, polyalcohols, water soluble polymers, clay minerals, water-insoluble natural or synthetic polymers such as resins, plastics and rubbers, purified water, etc. Further, pH adjusters, antioxidants, chelating agents, antibacterial and antifungal agents, colorants, flavors, and/or the like can be added as needed. The base ingredients of the external medicines of the present invention are not limited to the above ingredients. As needed, other ingredients can be added and examples thereof include ingredients having a differentiation inducing activity, blood flow increasing agents, bactericides, anti-inflammatories, cell activators, vitamins, amino acids, moisturizers, keratolytic agents, etc. The amount of the base ingredients to be added is determined so that the concentration will be a usual base ingredient concentration in the production of external medicines.

The compound of the present invention may be provided as a food or drink, a feed, or a food additive.

The food or drink of the present invention may contain one or more types of food additives commonly used in food or drink, and examples of the food additives include sweeteners, colorants, preservatives, thickening stabilizers, antioxidants, color fixatives, bleaching agents, antifungal agents, gum bases, bittering agents, enzymes, brighteners, acidulants, seasonings, emulsifiers, fortifiers, processing aids, flavors, and spice extracts. The food or drink of the present invention includes health foods, functional foods, foods for specified health use, foods for babies, foods for small children, foods for pregnant women and nursing mothers, foods for elderly people, and foods for sick people.

The form of the food or drink of the present invention is not particularly limited. Specific examples thereof include so-called dietary supplements in forms of tablets, granules, powders, energy drinks, or the like. Other examples thereof include drinks, such as tea drink, refreshing drink, carbonated drink, nutritional drink, fruit juice, and lactic drink; noodles, such as buckwheat noodle, wheat noodle, Chinese noodle, and instant noodle; sweets and bakery products, such as drop, candy, gum, chocolate, snack, biscuit, jelly, jam, cream, pastry, and bread; fishery or livestock products, such as fish sausage, ham, and sausage; dairy products, such as processed milk and fermented milk; fats, oils and processed foods thereof, such as vegetable oil, oil for deep frying, margarine, mayonnaise, shortening, whipped cream, and dressing; seasonings, such as sauce and dipping sauce; retort pouch foods, such as curry, stew, rice-bowl cuisine, porridge, and rice soup; and frozen desserts, such as ice cream, sherbet, and shaved ice.

The amount of intake of the food or drink of the present invention is not particularly limited, and may be determined depending on the form of the food or drink, the age, sex, condition, and the like of the subject who is to take the food or drink, and other conditions.

The compound of the present invention or a salt thereof can be used for a therapeutic method for a disease in which tau, β-secretase or Aβ is involved. Specific examples of the method include the following (a) to (c):

(a) a therapeutic method for a disease in which tau is involved, the method comprising the step of administering a compound represented by the general formula (I) or a salt thereof to a patient with a disease in which tau is involved;

(b) a therapeutic method for a disease in which β-secretase is involved, the method comprising the step of administering a compound represented by the general formula (I) or a salt thereof to a patient with a disease in which β-secretase is involved; and (c) a therapeutic method for a disease in which Aβ is involved, the method comprising the step of administering a compound represented by the general formula (I) or a salt thereof to a patient with a disease in which Aβ is involved.

The diseases in which tau, β-secretase or Aβ is involved preferably include diseases of which the onset mechanism involves tau, β-secretase or Aβ. Specific examples of such diseases include Alzheimer's disease (familial Alzheimer's disease and sporadic Alzheimer's disease), senile dementia, Down syndrome, Parkinson's disease, Creutzfeldt-Jakob disease, amyotrophic lateral sclerosis, diabetic neuropathy, Huntington's chorea, multiple sclerosis, etc. Among these, preferred is Alzheimer's disease.

The route of administration, dosage form, and dosage of the compound of the present invention, and the subject to which the compound is to be administered may be the same as those described above for the preparation comprising the compound of the present invention.

The compound of the present invention can also be used for a method for inhibiting tau aggregation, a method for inhibiting β-secretase, and a method for inhibiting Aβ aggregation. Specific examples of the method include the following (d) to (i):

(d) a method for inhibiting tau aggregation, the method comprising the step of administering a compound represented by the general formula (I) or a salt thereof to a mammal including human, thereby inhibiting tau aggregation in the body of the mammal including human;

(e) a method for inhibiting tau aggregation, the method comprising the step of bringing a compound represented by the general formula (I) or a salt thereof in contact with tau;

(f) a method for inhibiting β-secretase, the method comprising the step of administering a compound represented by the general formula (I) or a salt thereof to a mammal including human, thereby inhibiting β-secretase in the living human body;

(g) a method for inhibiting β-secretase, the method comprising the step of bringing a compound represented by the general formula (I) or a salt thereof in contact with β-secretase;

(h) a method for inhibiting Aβ aggregation, the method comprising the step of administering a compound represented by the general formula (I) or a salt thereof to a mammal including human, thereby inhibiting Aβ aggregation in the body of the mammal including human; and (i) a method for inhibiting Aβ aggregation, the method comprising the step of bringing a compound represented by the general formula (I) or a salt thereof in contact with Aβ.

The salt in the above methods may be a pharmacologically acceptable salt.

The present invention also includes, as one embodiment, use of the compound of the present invention or a salt thereof in the production of a prophylactic or therapeutic preparation for a disease in which tau, β-secretase or Aβ is involved. The disease in which tau, β-secretase or Aβ is involved may be the same as those described above, and is preferably Alzheimer's disease.

The present invention also includes, as another embodiment, the compound of the present invention or a salt thereof for use in the prevention or treatment of a disease in which tau, β-secretase or Aβ is involved. The disease in which tau, β-secretase or Aβ is involved may be the same as those described above, and is preferably Alzheimer's disease.

EXAMPLES

The present invention will be described in further detail with reference to Examples etc., but the present invention is not limited thereto. Various modifications of the present invention can be made by a person who has common knowledge in the art, without departing from the scope of the technical idea of the present invention.

In Examples, the compound of the general formula (I) is detected as a mixture of two tautomers represented by the general formulas (I) and (I') shown below, depending on the measurement conditions of $^1$H-NMR. The two tautomers are isomers of the same substance. Therefore, the synthetic compounds in Examples can be named based on either the general formula (I) or the general formula (I').

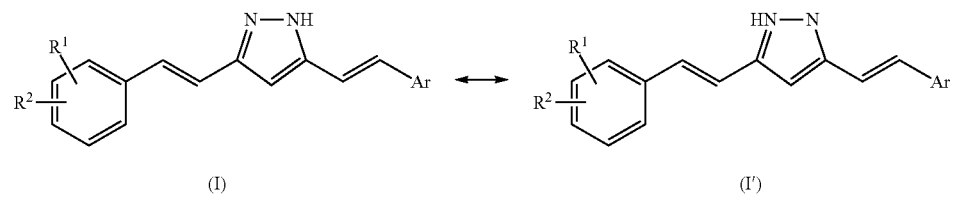

A compound represented by the above general formula (C) is an important intermediate in the present invention. The compound of the general formula (C) can exist in tautomeric forms including a keto form and an enol form, and these tautomeric forms are the same substance. Therefore, such an intermediate can be named based on any of the general formula (C), the general formula (C'), and the general formula (C").

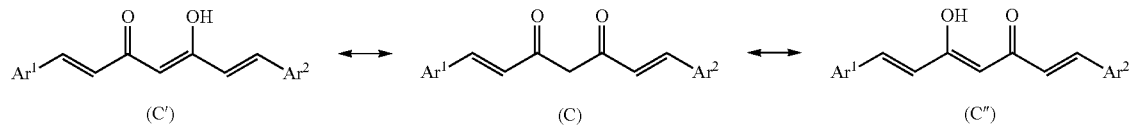

(C')  (C)  (C'')

The following abbreviations are also used herein.

TABLE 1

| Abbreviation | Reagent, solvent, etc. |
| --- | --- |
| AcOEt | Ethyl acetate |
| AcOH | Acetic acid |
| $CHCl_3$ | Chloroform |
| IBCF | Isobutyl chloroformate |
| $K_2CO_3$ | Potassium carbonate |
| LAH | Lithium aluminium hydride |
| $MgSO_4$ | Magnesium sulfate |
| $Na_2SO_4$ | Sodium sulfate |
| $NaHCO_3$ | Sodium hydrogen carbonate |
| NaOH | Sodium hydroxide |
| PTLC | Preparative thin-layer chromatography |
| THF | Tetrahydrofuran |

Example 1: Synthesis of 4-[2-[4-[(E)-2-[5-[(E)-2-(1H-indol-6-yl)vinyl]-1H-pyrazol-3-yl]vinyl]phenoxy]ethyl]morpholine Example 1-1: Synthesis of (1E,6E)-1-(1H-indol-6-yl)-7-[4-(2-morpholinoethoxy)phenyl]hepta-1,6-diene-3,5-dione To 2.5 g of (E)-6-(1H-indol-6-yl)hex-5-ene-2,4-dione were added 44 mL of AcOEt and 1.07 g of boron oxide, and the mixture was stirred at 70° C. for 40 minutes. To this, 2.27 g of 4-(2-morpholinoethoxy)benzaldehyde and 7.07 mL of tributyl borate were successively added, and the mixture was stirred at the same temperature for 40 minutes. Then, 0.11 mL of piperidine was added, and the mixture was stirred at 70° C. for 1.5 hours and was allowed to cool back to room temperature. To the reaction mixture, 22 mL of a 20% $K_2CO_3$ aqueous solution and 20 mL of THF were added and the mixture was stirred at room temperature for 10 minutes. The organic layer was separated, washed with saturated brine, dried over $MgSO_4$, and concentrated. The residue was purified by silica gel column chromatography ($CHCl_3$/acetone or $CHCl_3$/methanol system) to give 1.62 g of the title compound (33% yield).

Example 1-2: Synthesis of 4-[2-[4-[(E)-2-[5-[(E)-2-(1H-indol-6-yl)vinyl]-1H-pyrazol-3-yl]vinyl]phenoxy]ethyl]morpholine To 1.5 g of (1E,6E)-1-(1H-indol-6-yl)-7-[4-(2-morpholinoethoxy)phenyl]hepta-1,6-diene-3,5-dione were added 13.5 mL of AcOH and 1.31 mL of hydrazine monohydrate, and the mixture was stirred at 60° C. for 3 hours. The reaction mixture was allowed to cool back to room temperature and poured into a stirring mixture of 18.7 g of $K_2CO_3$, 95 mL of cold water, 30 mL of AcOEt and 20 mL of THF. The organic layer was separated, washed with saturated brine, dried over $MgSO_4$, and concentrated. The residue was purified by silica gel column chromatography ($CHCl_3$/acetone or $CHCl_3$/methanol system) to give 0.62 g of the title compound (42% yield).

Example 2: Synthesis of 4-[2-[4-[(E)-2-[5-[(E)-2-(1,3-benzodioxol-5-yl)vinyl]-1H-pyrazol-3-yl]vinyl]-3-methoxyphenoxy]ethyl]morpholine Example 2-1: Synthesis of (1E,6E)-1-(1,3-benzodioxol-5-yl)-7-[2-methoxy-4-(2-morpholinoethoxy)phenyl]hepta-1,6-diene-3,5-dione The title compound was obtained in the same manner as in Example 1-1.

Example 2-2: Synthesis of 4-[2-[4-[(E)-2-[5-[(E)-2-(1,3-benzodioxol-5-yl)vinyl]-1H-pyrazol-3-yl]vinyl]-3-methoxyphenoxy]ethyl]morpholine The title compound was obtained in the same manner as in Example 1-2.

Example 3: Synthesis of 4-[2-[4-[(E)-2-[5-[(E)-2-(1,3-benzodioxol-5-yl)vinyl]-1H-pyrazol-3-yl]vinyl]phenoxy]ethyl]morpholine Example 3-1: Synthesis of (1E,6E)-1-(1,3-benzodioxol-5-yl)-7-[4-(2-morpholinoethoxy)phenyl]hepta-1,6-diene-3,5-dione The title compound was obtained in the same manner as in Example 1-1.

Example 3-2: Synthesis of 4-[2-[4-[(E)-2-[5-[(E)-2-(1,3-benzodioxol-5-yl)vinyl]-1H-pyrazol-3-yl]vinyl]phenoxy]ethyl]morpholine The title compound was obtained in the same manner as in Example 1-2.

Example 4: Synthesis of 6-[(E)-2-[3-[(E)-2-[2-methoxy-4-[(4-methylpiperazin-1-yl)methyl]phenyl]vinyl]-1H-pyrazol-5-yl]vinyl]-1H-indole Example 4-1: Synthesis of 2-methoxy-4-[(4-methylpiperazin-1-yl)methyl]benzoic acid methyl ester To 100 mL of ethanol were added 10.0 g of 1-methylpiperazine and 20.2 g of triethylamine. To the mixture cooled with ice, 25 mL of a solution of 24.6 g of 4-(bromomethyl)-2-methoxy-benzoic acid methyl ester in ethanol was added dropwise. The mixture was stirred at room temperature for 18 hours. The reaction mixture was concentrated. To the residue, 75 mL of water and 250 mL of methylene chloride were added, and the organic layer was separated. The obtained organic layer was dried over $Na_2SO_4$ and concentrated. The residue was purified by amino-silica gel column chromatography (heptane/AcOEt system) to give 22.4 g of the title compound (85% yield).

Example 4-2: Synthesis of [2-methoxy-4-[(4-methylpiperazin-1-yl)methyl]phenyl]methanol To 200 mL of a suspension of 5.21 g of LAH in THF cooled with ice was added dropwise, under argon flow, 50 mL of a solution of 25.5 g of 2-methoxy-4-[(4-methylpiperazin-1-yl)methyl]benzoic acid methyl ester in THF. The mixture was stirred under ice cooling for 1 hour and further stirred at room temperature for 22 hours. To the reaction mixture cooled with ice, 25 mL of a 10% NaOH water was added dropwise. After 30-minute stirring, the mixture was filtered through Celite. The filtrate was washed with 150 mL of THF and then was concentrated. To the residue, 50 mL of saturated brine and 300 mL of dichloromethane were added, and the organic layer was separated. The organic layer was concentrated. The residue was purified by silica gel column chromatography (CHCl$_3$/methanol system) to give 22.4 g of the title compound (98% yield).

Example 4-3: Synthesis of 2-methoxy-4-[(4-methylpiperazin-1-yl)methyl]benzaldehyde To 220 mL of a solution of 22.2 g of [2-methoxy-4-[(4-methylpiperazin-1-yl)methyl]phenyl]methanol in CHCl$_3$ was added 61.8 g of manganese dioxide, and the mixture was stirred at 55° C. for 13 hours. The reaction mixture was allowed to stand to cool. After insoluble matter was filtered off, the mother liquor was concentrated to give 21.8 g of the title compound (99% yield).

Example 4-4: Synthesis of (1E,6E)-1-(1H-indol-6-yl)-7-[2-methoxy-4-[(4-methylpiperazin-1-yl)methyl]phenyl]hepta-1,6-diene-3,5-dione To 200 mL of a solution of 7.56 g of (E)-6-(1H-indol-6-yl)hex-5-ene-2,4-dione in AcOEt was added 3.24 g of boron oxide, and the mixture was stirred at 70° C. for 1 hour. To this, 15 mL of a solution of 8.68 g of 2-methoxy-4-[(4-methylpiperazin-1-yl)methyl]benzaldehyde in AcOEt and 18.3 mL of triisopropyl borate were successively added, and the mixture was stirred at the same temperature for 40 minutes. Then, 10 mL of a solution of 0.35 mL of piperidine in AcOEt was added. The mixture was stirred at 70° C. for 3 hours and was allowed to cool back to room temperature. To the reaction mixture, 100 mL of a 10% K$_2$CO$_3$ aqueous solution was added, and the mixture was stirred for 1 hour. The organic layer was separated and concentrated. The residue was purified by amino-silica gel column chromatography (heptane/AcOEt system) to give 7.14 g of the title compound (47% yield).

Example 4-5: Synthesis of 6-[(E)-2-[3-[(E)-2-[2-methoxy-4-[(4-methylpiperazin-1-yl)methyl]phenyl]vinyl]-1H-pyrazol-5-yl]vinyl]-1H-indole The title compound was obtained in the same manner as in Example 1-2.

Example 5: Synthesis of 3,5-bis[(E)-2-[4-(2-morpholinoethoxy)phenyl]vinyl]-1H-pyrazole Example 5-1: Synthesis of (1E,6E)-1,7-bis[4-(2-morpholinoethoxy)phenyl]hepta-1,6-diene-3,5-dione To 2.0 g of pentane-2,4-dione were added 10.0 mL of AcOEt and 0.70 g of boron oxide, and the mixture was stirred at 70° C. for 1 hour. To the reaction mixture, 30 mL of a solution of 9.4 g of 4-(2-morpholinoethoxy)benzaldehyde in AcOEt and 10.7 mL of tributyl borate were successively added, and the mixture was stirred at the same temperature for 1 hour. To this, 0.4 mL of 1-butylamine was added, and the mixture was stirred at 70° C. for 2.5 hours and was allowed to cool back to room temperature. To the reaction mixture, 50 mL of a 10% K$_2$CO$_3$ aqueous solution and 30 mL of THF were added, and the mixture was stirred at room temperature for 10 minutes. The organic layer was separated, washed with saturated brine, dried over MgSO$_4$, and concentrated. The residue was treated with 100 mL of diethyl ether to give 2.51 g of the title compound as a powder (24% yield).

Example 5-2: Synthesis of 3,5-bis[(E)-2-[4-(2-morpholinoethoxy)phenyl]vinyl]-1H-pyrazole The title compound was obtained in the same manner as in Example 1-2.

Example 6: Synthesis of N,N-dimethyl-2-[4-[(E)-2-[3-[(E)-2-[4-(2-morpholinoethoxy)phenyl]vinyl]-1H-pyrazol-5-yl]vinyl]phenoxy]acetamide Example 6-1: Synthesis of (E)-6-[4-(2-morpholinoethoxy)phenyl]hex-5-ene-2,4-dione To 30.0 g of (E)-3-[4-(2-morpholinoethoxy)phenyl]-2-propenoic acid was added 600 mL of THF under argon flow. To the mixture cooled with ice, 12.1 g of triethylamine and 15.5 g of IBCF were successively added dropwise. The mixture was stirred at room temperature for 2 hours to prepare an acid anhydride. In a separate container, 200 mL of THF and 16.3 g of acetylacetone were added to 15.5 g of magnesium chloride under argon flow. To the mixture cooled with ice, 17.5 mL of pyridine was added dropwise over 25 minutes. The mixture was stirred at room temperature for 2 hours. To the reaction mixture cooled with ice, the above-prepared acid anhydride cooled with ice was added dropwise over 45 minutes. The mixture was stirred at room temperature overnight. The reaction mixture was added to 2 L of a saturated aqueous ammonium chloride solution and 2 L of CHCl$_3$, and the organic layer was separated. The obtained organic layer was dried over Na$_2$SO$_4$ and concentrated.

The residue was dissolved in 100 mL of THF. While the mixture was stirred under ice cooling, 40 mL of a 28% ammonia water was added dropwise. The mixture was stirred at the same temperature for 1 hour. The reaction mixture was added to 1 L of CHCl$_3$ and 1 L of saturated brine, and the organic layer was separated. The obtained organic layer was dried over Na$_2$SO$_4$ and concentrated. The residue was purified by silica gel column chromatography (CHCl$_3$/methanol system) to give 26.5 g of the title compound (77% yield).

Example 6-2: Synthesis of N,N-dimethyl-2-[4-[(1E,6E)-7-[4-(2-morpholinoethoxy)phenyl]-3,5-dioxo-hepta-1,6-dienyl]phenoxy]acetamide The title compound was obtained in the same manner as in Example 4-4.

Example 6-3: Synthesis of N,N-dimethyl-2-[4-[(E)-2-[3-[(E)-2-[4-(2-morpholinoethoxy)phenyl]vinyl]-1H-pyrazol-5-yl]vinyl]phenoxy]acetamide To 2.70 g of N,N-dimethyl-2-[4-[(1E,6E)-7-[4-(2-morpholinoethoxy)phenyl]-3,5-dioxo-hepta-1,6-dienyl]phenoxy]acetamide were added 2.80 g of hydrazine dihydrochloride and 54 mL of methanol, and the mixture was stirred at 40° C. overnight. The reaction mixture was allowed to stand to cool, and poured into 200 mL of a saturated aqueous NaHCO$_3$ solution. To this, 600 mL of AcOEt was added, and the organic layer was separated. The obtained organic layer was washed with saturated brine, dried over Na$_2$SO$_4$, and concentrated. The residue was purified by silica gel column chromatography (CHCl$_3$/methanol system) to give 1.76 g of the title compound (66% yield).

Example 7: Synthesis of 4-[2-[4-[(E)-2-[5-[(E)-2-(3,4-dimethoxyphenyl)vinyl]-1H-pyrazol-3-yl]vinyl]phenoxy]ethyl]morpholine Example 7-1: Synthesis of (1E,6E)-1-(3,4-dimethoxyphenyl)-7-[4-(2-morpholinoethoxy)phenyl]hepta-1,6-diene-3,5-dione The title compound was obtained in the same manner as in Example 4-4.

Example 7-2: Synthesis of 4-[2-[4-[(E)-2-[5-[(E)-2-(3,4-dimethoxyphenyl)vinyl]-1H-pyrazol-3-yl]vinyl]phenoxy]ethyl]morpholine The title compound was obtained in the same manner as in Example 6-3.

Example 8: Synthesis of 4-[2-[4-[(E)-2-[5-[(E)-2-(3H-benzimidazol-5-yl)vinyl]-1H-pyrazol-3-yl]vinyl]phenoxy]ethyl]morpholine Example 8-1: Synthesis of (1E,6E)-1-(3H-benzimidazol-5-yl)-7-[4-(2-morpholinoethoxy)phenyl]hepta-1,6-diene-3,5-dione The title compound was obtained in the same manner as in Example 4-4.

Example 8-2: Synthesis of 4-[2-[4-[(E)-2-[5-[(E)-2-(3H-benzimidazol-5-yl)vinyl]-1H-pyrazol-3-yl]vinyl]phenoxy]ethyl]morpholine The title compound was obtained in the same manner as in Example 6-3.

Example 9: Synthesis of 2-[[3-methoxy-4-[(E)-2-[5-[(E)-2-(1H-pyrrol-2-yl)vinyl]-1H-pyrazol-3-yl]vinyl]phenoxy]methyl]pyridine Example 9-1: Synthesis of (1E,6E)-1-[2-methoxy-4-(2-pyridylmethoxy)phenyl]-7-(1H-pyrrol-2-yl)hepta-1,6-diene-3,5-dione The title compound was obtained in the same manner as in Example 1-1.

Example 9-2: Synthesis of 2-[[3-methoxy-4-[(E)-2-[5-[(E)-2-(1H-pyrrol-2-yl)vinyl]-1H-pyrazol-3-yl]vinyl]phenoxy]methyl]pyridine To 30 mg of (1E,6E)-1-[2-methoxy-4-(2-pyridylmethoxy)phenyl]-7-(1H-pyrrol-2-yl)hepta-1,6-diene-3,5-dione were added 1 mL of THF, 3 μL of AcOH and 4 μL of hydrazine monohydrate, and the mixture was stirred at 60° C. for 4 hours. To this, 500 μL of AcOH was added and the mixture was stirred at 80° C. for 1 hour. To this, 4 μL of hydrazine monohydrate was added and the mixture was stirred at 80° C. for 1 hour. The reaction mixture was allowed to cool back to room temperature, and a saturated aqueous NaHCO$_3$ solution was added. After extraction with AcOEt, the organic layer was separated. The obtained organic layer was washed with saturated brine, dried over MgSO$_4$, and concentrated. The residue was purified by PTLC (CHCl$_3$/methanol or AcOEt system) to give 8 mg of the title compound (27% yield).

Example 10: Synthesis of 3-benzyloxy-N,N-diethyl-4-[(E)-2-[5-[(E)-2-(1-methylindol-6-yl)vinyl]-1H-pyrazol-3-yl]vinyl]aniline Example 10-1: Synthesis of (E)-6-(1-methylindol-6-yl)hex-5-ene-2,4-dione The title compound was obtained in the same manner as in Example 6-1.

Example 10-2: Synthesis of (1E,6E)-1-[2-benzyloxy-4-(diethylamino)phenyl]-7-(1-methylindol-6-yl)hepta-1,6-diene-3,5-dione The title compound was obtained in the same manner as in Example 1-1.

Example 10-3: Synthesis of 3-benzyloxy-N,N-diethyl-4-[(E)-2-[5-[(E)-2-(1-methylindol-6-yl)vinyl]-1H-pyrazol-3-yl]vinyl]aniline The title compound was obtained in the same manner as in Example 9-2.

Example 11: Synthesis of N,N-diethyl-4-[(E)-2-[5-[(E)-2-(1-methylindol-6-yl)vinyl]-1H-pyrazol-3-yl]vinyl]-3-(2-morpholinoethoxy)aniline Example 11-1: Synthesis of (1E,6E)-1-[4-(diethylamino)-2-(2-morpholinoethoxy)phenyl]-7-(1-methylindol-6-yl)hepta-1,6-diene-3,5-dione The title compound was obtained in the same manner as in Example 1-1.

Example 11-2: Synthesis of N,N-diethyl-4-[(E)-2-[5-[(E)-2-(1-methylindol-6-yl)vinyl]-1H-pyrazol-3-yl]vinyl]-3-(2-morpholinoethoxy)aniline The title compound was obtained in the same manner as in Example 9-2.

Example 12: Synthesis of 2-[(E)-2-[5-[(E)-2-(1-methylindol-6-yl)vinyl]-1H-pyrazol-3-yl]vinyl]-5-(2-pyridylmethoxy)phenol Example 12-1: Synthesis of (1E,6E)-1-[2-hydroxy-4-(2-pyridylmethoxy)phenyl]-7-(1-methylindol-6-yl)hepta-1,6-diene-3,5-dione The title compound was obtained in the same manner as in Example 1-1.

Example 12-2: Synthesis of 2-[(E)-2-[5-[(E)-2-(1-methylindol-6-yl)vinyl]-1H-pyrazol-3-yl]vinyl]-5-(2-pyridylmethoxy)phenol The title compound was obtained in the same manner as in Example 9-2.

Example 13: Synthesis of 4-[2-[2-[(E)-2-[5-[(E)-2-(1H-indol-6-yl)vinyl]-1H-pyrazol-3-yl]vinyl]-5-(2-pyridylmethoxy)phenoxy]ethyl]morpholine Example 13-1: Synthesis of 2-(2-morpholinoethoxy)-4-(2-pyridylmethoxy)benzaldehyde To 1.0 g of 2-hydroxy-4-(2-pyridylmethoxy)benzaldehyde were successively added 30 mL of acetonitrile, 4.26 g of cesium carbonate and 0.85 g of 4-(2-chloroethyl)morpholine hydrochloride. The mixture was stirred at 90° C. for 2 hours. To the reaction mixture, 50 mL of water and 150 mL of AcOEt were added, and the organic layer was separated. The obtained organic layer was dried over $Na_2SO_4$ and concentrated to give 1.56 g of the title compound in quantitative yield.

Example 13-2: (1E,6E)-1-(1H-indol-6-yl)-7-[2-(2-morpholinoethoxy)-4-(2-pyridylmethoxy)phenyl]hepta-1,6-diene-3,5-dione The title compound was obtained in the same manner as in Example 1-1.

Example 13-3: Synthesis of 4-[2-[2-[(E)-2-[5-[(E)-2-(1H-indol-6-yl)vinyl]-1H-pyrazol-3-yl]vinyl]-5-(2-pyridylmethoxy)phenoxy]ethyl]morpholine The title compound was obtained in the same manner as in Example 9-2.

Example 14: Synthesis of 4-[2-[3-methoxy-4-[(E)-2-[5-[(E)-2-(1-methylindol-6-yl)vinyl]-1H-pyrazol-3-yl]vinyl]phenoxy]ethyl]morpholine Example 14-1: Synthesis of (1E,6E)-1-[2-methoxy-4-(2-morpholinoethoxy)phenyl]-7-(1-methylindol-6-yl)hepta-1,6-diene-3,5-dione The title compound was obtained in the same manner as in Example 1-1.

Example 14-2: Synthesis of 4-[2-[3-methoxy-4-[(E)-2-[5-[(E)-2-(1-methylindol-6-yl)vinyl]-1H-pyrazol-3-yl]vinyl]phenoxy]ethyl]morpholine The title compound was obtained in the same manner as in Example 1-2.

Example 15: Synthesis of 4-[2-[4-[(E)-2-[5-[(E)-2-(1-methylindol-6-yl)vinyl]-1H-pyrazol-3-yl]vinyl]phenoxy]ethyl]morpholine Example 15-1: Synthesis of (1E,6E)-1-(1-methylindol-6-yl)-7-[4-(2-morpholinoethoxy)phenyl]hepta-1,6-diene-3,5-dione The title compound was obtained in the same manner as in Example 1-1.

Example 15-2: Synthesis of 4-[2-[4-[(E)-2-[5-[(E)-2-(1-methylindol-6-yl)vinyl]-1H-pyrazol-3-yl]vinyl]phenoxy]ethyl]morpholine The title compound was obtained in the same manner as in Example 1-2.

Example 16: Synthesis of 6-[(E)-2-[3-[(E)-2-[2-fluoro-4-(2-pyridylmethoxy)phenyl]vinyl]-1H-pyrazol-5-yl]vinyl]-1-methylindole Example 16-1: Synthesis of (1E,6E)-1-[2-fluoro-4-(2-pyridylmethoxy)phenyl]-7-(1-methylindol-6-yl)hepta-1,6-diene-3,5-dione The title compound was obtained in the same manner as in Example 1-1.

Example 16-2: Synthesis of 6-[(E)-2-[3-[(E)-2-[2-fluoro-4-(2-pyridylmethoxy)phenyl]vinyl]-1H-pyrazol-5-yl]vinyl]-1-methylindole The title compound was obtained in the same manner as in Example 1-2.

Example 17: Synthesis of 1-methyl-6-[(E)-2-[3-[(E)-2-[4-(2-pyridylmethoxy)phenyl]vinyl]-1H-pyrazol-5-yl]vinyl]indole Example 17-1: Synthesis of (1E,6E)-1-(1-methylindol-6-yl)-7-[4-(2-pyridylmethoxy)phenyl]hepta-1,6-diene-3,5-dione The title compound was obtained in the same manner as in Example 1-1.

Example 17-2: Synthesis of 1-methyl-6-[(E)-2-[3-[(E)-2-[4-(2-pyridylmethoxy)phenyl]vinyl]-1H-pyrazol-5-yl]vinyl]indole The title compound was obtained in the same manner as in Example 1-2.

Example 18: Synthesis of 1-methyl-6-[(E)-2-[3-[(E)-2-[4-(4-methylpiperazin-1-yl)phenyl]vinyl]-1H-pyrazol-5-yl]vinyl]indole Example 18-1: Synthesis of (1E,6E)-1-(1-methylindol-6-yl)-7-[4-(4-methylpiperazin-1-yl)phenyl]hepta-1,6-diene-3,5-dione The title compound was obtained in the same manner as in Example 1-1.

Example 18-2: Synthesis of 1-methyl-6-[(E)-2-[3-[(E)-2-[4-(4-methylpiperazin-1-yl)phenyl]vinyl]-1H-pyrazol-5-yl]vinyl]indole The title compound was obtained in the same manner as in Example 1-2.

Example 19: Synthesis of 2-[[3-fluoro-4-[(E)-2-[5-[(E)-2-(1-methylpyrrol-2-yl)vinyl]-1H-pyrazol-3-yl]vinyl]phenoxy]methyl]pyridine Example 19-1: Synthesis of (E)-3-[2-fluoro-4-(2-pyridylmethoxy)phenyl]-2-propenoic acid To 1.8 g of malonic acid were added 18 mL of pyridine, 2.0 g of 2-fluoro-4-(2-pyridylmethoxy)benzaldehyde and 0.21 mL of piperidine. The mixture was stirred at 75° C. for 1.5 hours and further stirred at 95° C. for 1 hour. The reaction mixture was cooled with ice, water was added thereto, and 10% hydrochloric acid was added to adjust the pH to 4. The resulting precipitate was separated by filtration to give 2.0 g of the title compound (85% yield).

Example 19-2: Synthesis of (E)-6-[2-fluoro-4-(2-pyridylmethoxy)phenyl]hex-5-ene-2,4-dione The title compound was obtained in the same manner as in Example 6-1.

Example 19-3: Synthesis of (1E,6E)-1-[2-fluoro-4-(2-pyridylmethoxy)phenyl]-7-(1-methylpyrrol-2-yl)hepta-1,6-diene-3,5-dione The title compound was obtained in the same manner as in Example 1-1.

Example 19-4: Synthesis of 2-[[3-fluoro-4-[(E)-2-[5-[(E)-2-(1-methylpyrrol-2-yl)vinyl]-1H-pyrazol-3-yl]vinyl]phenoxy]methyl]pyridine The title compound was obtained in the same manner as in Example 1-2.

Example 20: Synthesis of 2-[[4-[(E)-2-[5-[(E)-2-(1-methylpyrrol-2-yl)vinyl]-1H-pyrazol-3-yl]vinyl]phenoxy]methyl]pyridine Example 20-1: Synthesis of (E)-6-[4-(2-pyridylmethoxy)phenyl]hex-5-ene-2,4-dione The title compound was obtained in the same manner as in Example 6-1.

Example 20-2: Synthesis of (1E,6E)-1-(1-methylpyrrol-2-yl)-7-[4-(2-pyridylmethoxy)phenyl]hepta-1,6-diene-3,5-dione The title compound was obtained in the same manner as in Example 1-1.

Example 20-3: Synthesis of 2-[[4-[(E)-2-[5-[(E)-2-(1-methylpyrrol-2-yl)vinyl]-1H-pyrazol-3-yl]vinyl]phenoxy]methyl]pyridine The title compound was obtained in the same manner as in Example 1-2.

Example 21: Synthesis of 4-[2-[3-methoxy-4-[(E)-2-[5-[(E)-2-(1-methylpyrrol-2-yl)vinyl]-1H-pyrazol-3-yl]vinyl]phenoxy]ethyl]morpholine Example 21-1: Synthesis of (1E,6E)-1-[2-methoxy-4-(2-morpholinoethoxy)phenyl]-7-(1-methylpyrrol-2-yl)hepta-1,6-diene-3,5-dione The title compound was obtained in the same manner as in Example 1-1.

Example 21-2: Synthesis of 4-[2-[3-methoxy-4-[(E)-2-[5-[(E)-2-(1-methylpyrrol-2-yl)vinyl]-1H-pyrazol-3-yl]vinyl]phenoxy]ethyl]morpholine The title compound was obtained in the same manner as in Example 1-2.

Example 22: Synthesis of 2-[[3-methoxy-4-[(E)-2-[5-[(E)-2-(1-methylpyrrol-2-yl)vinyl]-1H-pyrazol-3-yl]vinyl]phenoxy]methyl]pyridine Example 22-1: Synthesis of (1E,6E)-1-[2-methoxy-4-(2-pyridylmethoxy)phenyl]-7-(1-methylpyrrol-2-yl)hepta-1,6-diene-3,5-dione The title compound was obtained in the same manner as in Example 1-1.

Example 22-2: Synthesis of 2-[[3-methoxy-4-[(E)-2-[5-[(E)-2-(1-methylpyrrol-2-yl)vinyl]-1H-pyrazol-3-yl]vinyl]phenoxy]methyl]pyridine The title compound was obtained in the same manner as in Example 1-2.

Example 23: Synthesis of 2-[[4-[(E)-2-[5-[(E)-2-(1,5-dimethylpyrrol-2-yl)vinyl]-1H-pyrazol-3-yl]vinyl]-3-methoxyphenoxy]methyl]pyridine Example 23-1: Synthesis of (1E,6E)-1-(1,5-dimethylpyrrol-2-yl)-7-[2-methoxy-4-(2-pyridylmethoxy)phenyl]hepta-1,6-diene-3,5-dione The title compound was obtained in the same manner as in Example 1-1.

Example 23-2: Synthesis of 2-[[4-[(E)-2-[5-[(E)-2-(1,5-dimethylpyrrol-2-yl)vinyl]-1H-pyrazol-3-yl]vinyl]-3-methoxyphenoxy]methyl]pyridine The title compound was obtained in the same manner as in Example 1-2.

Example 24: Synthesis of 2-[[3-methoxy-4-[(E)-2-[5-[(E)-2-(1,3,5-trimethylpyrrol-2-yl)vinyl]-1H-pyrazol-3-yl]vinyl]phenoxy]methyl]pyridine Example 24-1: Synthesis of (1E,6E)-1-[2-methoxy-4-(2-pyridylmethoxy)phenyl]-7-(1,3,5-trimethylpyrrol-2-yl)hepta-1,6-diene-3,5-dione The title compound was obtained in the same manner as in Example 1-1.

Example 24-2: Synthesis of 2-[[3-methoxy-4-[(E)-2-[5-[(E)-2-(1,3,5-trimethylpyrrol-2-yl)vinyl]-1H-pyrazol-3-yl]vinyl]phenoxy]methyl]pyridine The title compound was obtained in the same manner as in Example 1-2.

Example 25: Synthesis of 2-[(E)-2-[3-[(E)-2-[2-methoxy-4-(2-pyridylmethoxy)phenyl]vinyl]-1H-pyrazol-5-yl]vinyl]-6-methylpyridine Example 25-1: Synthesis of (1E,6E)-1-[2-methoxy-4-(2-pyridylmethoxy)phenyl]-7-(6-methyl-2-pyridyl)hepta-1,6-diene-3,5-dione The title compound was obtained in the same manner as in Example 1-1.

Example 25-2: Synthesis of 2-[(E)-2-[3-[(E)-2-[2-methoxy-4-(2-pyridylmethoxy)phenyl]vinyl]-1H-pyrazol-5-yl]vinyl]-6-methylpyridine The title compound was obtained in the same manner as in Example 1-2.

Example 26: Synthesis of 3-[(E)-2-[3-[(E)-2-[2-methoxy-4-(2-pyridylmethoxy)phenyl]vinyl]-1H-pyrazol-5-yl]vinyl]-2-methylpyridine

Example 26-1: Synthesis of (1E,6E)-1-[2-methoxy-4-(2-pyridylmethoxy)phenyl]-7-(2-methyl-3-pyridyl)hepta-1,6-diene-3,5-dione The title compound was obtained in the same manner as in Example 1-1.

Example 26-2: Synthesis of 3-[(E)-2-[3-[(E)-2-[2-methoxy-4-(2-pyridylmethoxy)phenyl]vinyl]-1H-pyrazol-5-yl]vinyl]-2-methylpyridine The title compound was obtained in the same manner as in Example 1-2.

Example 27: Synthesis of 1-methyl-4-[4-[(E)-2-[5-[(E)-2-(1-methylpyrrol-2-yl)vinyl]-1H-pyrazol-3-yl]vinyl]phenyl]piperazine

Example 27-1: Synthesis of (E)-6-(1-methylpyrrol-2-yl)hex-5-ene-2,4-dione

The title compound was obtained in the same manner as in Example 6-1.

Example 27-2: Synthesis of (1E,6E)-1-[4-(4-methylpiperazin-1-yl)phenyl]-7-(1-methylpyrrol-2-yl)hepta-1,6-diene-3,5-dione The title compound was obtained in the same manner as in Example 1-1.

Example 27-3: Synthesis of 1-methyl-4-[4-[(E)-2-[5-[(E)-2-(1-methylpyrrol-2-yl)vinyl]-1H-pyrazol-3-yl]vinyl]phenyl]piperazine The title compound was obtained in the same manner as in Example 1-2.

Example 28: Synthesis of 1-methyl-4-[4-[(E)-2-[5-[(E)-2-(1-methylpyrrol-2-yl)vinyl]-1H-pyrazol-3-yl]vinyl]phenyl]-1,4-diazepane

Example 28-1: Synthesis of (1E,6E)-1-[4-(4-methyl-1,4-diazepan-1-yl)phenyl]-7-(1-methylpyrrol-2-yl)hepta-1,6-diene-3,5-dione The title compound was obtained in the same manner as in Example 1-1.

Example 28-2: Synthesis of 1-methyl-4-[4-[(E)-2-[5-[(E)-2-(1-methylpyrrol-2-yl)vinyl]-1H-pyrazol-3-yl]vinyl]phenyl]-1,4-diazepane The title compound was obtained in the same manner as in Example 1-2.

Example 29: Synthesis of 3-[(E)-2-(4-isopropoxy-2-methoxyphenyl)vinyl]-5-[(E)-2-(1-methylpyrrol-2-yl)vinyl]-1H-pyrazole

Example 29-1: Synthesis of (1E,6E)-1-(4-isopropoxy-2-methoxyphenyl)-7-(1-methylpyrrol-2-yl)hepta-1,6-diene-3,5-dione The title compound was obtained in the same manner as in Example 1-1.

Example 29-2: Synthesis of 3-[(E)-2-(4-isopropoxy-2-methoxyphenyl)vinyl]-5-[(E)-2-(1-methylpyrrol-2-yl)vinyl]-1H-pyrazole The title compound was obtained in the same manner as in Example 1-2.

Example 30: Synthesis of 1-methyl-4-[2-[4-[(E)-2-[5-[(E)-2-(1-methylpyrrol-2-yl)vinyl]-1H-pyrazol-3-yl]vinyl]phenyl]ethyl]piperazine

Example 30-1: Synthesis of 4-[2-(4-methylpiperazin-1-yl)ethyl]benzaldehyde

To 87 mL of a solution of 8.7 g of 1-[2-(4-bromophenyl)ethyl]-4-methylpiperazine in THF cooled to −70° C. was added dropwise 21.1 mL of a solution of n-butyllithium (1.6 mol/L) in hexane, and the mixture was stirred at the same temperature for 30 minutes. While the reaction mixture was stirred at the same temperature, 3.6 mL of N,N-dimethylformamide was added dropwise. The mixture was stirred at the same temperature for 30 minutes. The cooling bath was removed, and the mixture was allowed to warm to −10° C., poured into a mixture of 12 mL of 1 N hydrochloric acid and 100 mL of cold water, and subjected to extraction with CHCl$_3$. The obtained extract was dried over MgSO$_4$ and concentrated to give 7.04 g of the title compound (98%).

Example 30-2: Synthesis of (1E,6E)-1-[4-[2-(4-methylpiperazin-1-yl)ethyl]phenyl]-7-(1-methylpyrrol-2-yl)hepta-1,6-diene-3,5-dione The title compound was obtained in the same manner as in Example 1-1.

Example 30-3: Synthesis of 1-methyl-4-[2-[4-[(E)-2-[5-[(E)-2-(1-methylpyrrol-2-yl)vinyl]-1H-pyrazol-3-yl]vinyl]phenyl]ethyl]piperazine The title compound was obtained in the same manner as in Example 1-2.

Example 31: Synthesis of 2-[2-[3-methoxy-4-[(E)-2-[5-[(E)-2-(1-methylpyrrol-2-yl)vinyl]-1H-pyrazol-3-yl]vinyl]phenoxy]ethyl]pyridine

Example 31-1: Synthesis of 2-methoxy-4-[2-(2-pyridyl)ethoxy]benzaldehyde

To a stirring ice-cooled mixture of 5.0 g of 4-hydroxy-2-methoxybenzaldehyde, 4.5 g of 2-(2-pyridyl)ethanol and 10.3 g of triphenylphosphine was added dropwise 15.8 g of a 40% solution of diethyl azodicarboxylate in toluene. The mixture was stirred at room temperature for 5 hours. The reaction mixture was concentrated, purified by silica gel column chromatography (hexane/acetone system) and further purified by silica gel column chromatography (hexane/ AcOEt system) to give 5.84 g of the title compound (69% yield).

Example 31-2: Synthesis of (1E,6E)-1-[2-methoxy-4-[2-(2-pyridyl)ethoxy]phenyl]-7-(1-methylpyrrol-2-yl)hepta-1,6-diene-3,5-dione The title compound was obtained in the same manner as in Example 1-1.

Example 31-3: Synthesis of 2-[2-[3-methoxy-4-[(E)-2-[5-[(E)-2-(1-methylpyrrol-2-yl)vinyl]-1H-pyrazol-3-yl]vinyl]phenoxy]ethyl]pyridine The title compound was obtained in the same manner as in Example 1-2.

Example 32: Synthesis of 2-[[3-methyl-4-[(E)-2-[5-[(E)-2-(1-methylpyrrol-2-yl)vinyl]-1H-pyrazol-3-yl]vinyl]phenoxy]methyl]pyridine Example 32-1: Synthesis of 2-methyl-4-(2-pyridylmethoxy)benzoic acid methyl ester To 0.85 g of 4-hydroxy-2-methyl benzoic acid methyl ester were added 12 mL of acetonitrile, 2.12 g of $K_2CO_3$ and 0.84 g of 2-(chloromethyl)pyridine hydrochloride, and the mixture was stirred at 90° C. for 4 hours. The reaction mixture was allowed to cool back to room temperature and neutralized by the addition of 5% hydrochloric acid. To this, 150 mL of AcOEt was added, and the organic layer was separated. The obtained organic layer was washed with saturated brine, dried over $MgSO_4$, and concentrated. The residue was purified by silica gel column chromatography (hexane/AcOEt system) to give 1.18 g of the title compound (89% yield).

Example 32-2: Synthesis of [2-methyl-4-(2-pyridylmethoxy)phenyl]methanol

To 1.0 g of 2-methyl-4-(2-pyridylmethoxy)benzoic acid methyl ester was added 8 mL of toluene under argon atmosphere. To the mixture cooled to −78° C., 8.7 mL of a solution of diisobutylaluminium hydride (1.0 mol/L) in toluene was added dropwise. The mixture was stirred at the same temperature for 6 hours and further stirred at −35° C. for 1 hour. To the reaction mixture, a saturated aqueous Rochelle salt solution was added, and the mixture was stirred at room temperature for 30 minutes. To this, 150 mL of diethyl ether was added, and the organic layer was separated. The obtained organic layer was dried over $Na_2SO_4$ and concentrated to give 0.83 g of the title compound (93% yield).

Example 32-3: Synthesis of 2-methyl-4-(2-pyridylmethoxy)benzaldehyde

To 0.72 g of [2-methyl-4-(2-pyridylmethoxy)phenyl]methanol were added 30 mL of $CHCl_3$ and 7.2 g of manganese dioxide, and the mixture was stirred at room temperature for 2 hours. Insoluble matter was filtered off from the reaction mixture, and the mother liquor was concentrated to give 0.70 g of the title compound (99% yield).

Example 32-4: Synthesis of (1E,6E)-1-[2-methyl-4-(2-pyridylmethoxy)phenyl]-7-(1-methylpyrrol-2-yl)hepta-1,6-diene-3,5-dione The title compound was obtained in the same manner as in Example 1-1.

Example 32-5: Synthesis of 2-[[3-methyl-4-[(E)-2-[5-[(E)-2-(1-methylpyrrol-2-yl)vinyl]-1H-pyrazol-3-yl]vinyl]phenoxy]methyl]pyridine The title compound was obtained in the same manner as in Example 1-2.

Example 33: Synthesis of 2-[2-[3-[(E)-2-[5-[(E)-2-(1-methylpyrrol-2-yl)vinyl]-1H-pyrazol-3-yl]vinyl]phenoxy]ethyl]pyridine Example 33-1: Synthesis of (1E,6E)-1-(1-methylpyrrol-2-yl)-7-[3-[2-(2-pyridyl)ethoxy]phenyl]hepta-1,6-diene-3,5-dione The title compound was obtained in the same manner as in Example 1-1.

Example 33-2: Synthesis of 2-[2-[3-[(E)-2-[5-[(E)-2-(1-methylpyrrol-2-yl)vinyl]-1H-pyrazol-3-yl]vinyl]phenoxy]ethyl]pyridine The title compound was obtained in the same manner as in Example 1-2.

Example 34: Synthesis of 2-[[3,5-dimethoxy-4-[(E)-2-[5-[(E)-2-(1-methylpyrrol-2-yl)vinyl]-1H-pyrazol-3-yl]vinyl]phenoxy]methyl]pyridine Example 34-1: Synthesis of 2,6-dimethoxy-4-(2-pyridylmethoxy)benzaldehyde The title compound was obtained in the same manner as in Example 32-1.

Example 34-2: Synthesis of (1E,6E)-1-[2,6-dimethoxy-4-(2-pyridylmethoxy)phenyl]-7-(1-methylpyrrol-2-yl)hepta-1,6-diene-3,5-dione The title compound was obtained in the same manner as in Example 1-1.

Example 34-3: Synthesis of 2-[[3,5-dimethoxy-4-[(E)-2-[5-[(E)-2-(1-methylpyrrol-2-yl)vinyl]-1H-pyrazol-3-yl]vinyl]phenoxy]methyl]pyridine The title compound was obtained in the same manner as in Example 1-2.

Example 35: Synthesis of 2-[[3-methoxy-4-[(E)-2-[5-[(E)-2-(1-methylimidazol-2-yl)vinyl]-1H-pyrazol-3-yl]vinyl]phenoxy]methyl]pyridine Example 35-1: Synthesis of (1E,6E)-1-[2-methoxy-4-(2-pyridylmethoxy)phenyl]-7-(1-methylimidazol-2-yl)hepta-1,6-diene-3,5-dione The title compound was obtained in the same manner as in Example 1-1.

Example 35-2: Synthesis of 2-[[3-methoxy-4-[(E)-2-[5-[(E)-2-(1-methylimidazol-2-yl)vinyl]-1H-pyrazol-3-yl]vinyl]phenoxy]methyl]pyridine The title compound was obtained in the same manner as in Example 1-2.

Example 36: Synthesis of 2-[[3-methoxy-4-[(E)-2-[5-[(E)-2-(3-methylimidazol-4-yl)vinyl]-1H-pyrazol-3-yl]vinyl]phenoxy]methyl]pyridine Example 36-1: Synthesis of (1E,6E)-1-[2-methoxy-4-(2-pyridylmethoxy)phenyl]-7-(3-methylimidazol-4-yl)hepta-1,6-diene-3,5-dione The title compound was obtained in the same manner as in Example 1-1.

Example 36-2: Synthesis of 2-[[3-methoxy-4-[(E)-2-[5-[(E)-2-(3-methylimidazol-4-yl)vinyl]-1H-pyrazol-3-yl]vinyl]phenoxy]methyl]pyridine The title compound was obtained in the same manner as in Example 1-2.

Example 37: Synthesis of 2-[(E)-2-[3-[(E)-2-[2-methoxy-4-(2-pyridylmethoxy)phenyl]vinyl]-1H-pyrazol-5-yl]vinyl]pyridine Example 37-1: Synthesis of (1E,6E)-1-[2-methoxy-4-(2-pyridylmethoxy)phenyl]-7-(2-pyridyl)hepta-1,6-diene-3,5-dione The title compound was obtained in the same manner as in Example 1-1.

Example 37-2: Synthesis of 2-[(E)-2-[3-[(E)-2-[2-methoxy-4-(2-pyridylmethoxy)phenyl]vinyl]-1H-pyrazol-5-yl]vinyl]pyridine The title compound was obtained in the same manner as in Example 1-2.

Example 38: Synthesis of 7-[(E)-2-[3-[(E)-2-[2-methoxy-4-(2-pyridylmethoxy)phenyl]vinyl]-1H-pyrazol-5-yl]vinyl]quinoline Example 38-1: Synthesis of (1E,6E)-1-[2-methoxy-4-(2-pyridylmethoxy)phenyl]-7-(7-quinolyl)hepta-1,6-diene-3,5-dione The title compound was obtained in the same manner as in Example 1-1.

Example 38-2: Synthesis of 7-[(E)-2-[3-[(E)-2-[2-methoxy-4-(2-pyridylmethoxy)phenyl]vinyl]-1H-pyrazol-5-yl]vinyl]quinoline The title compound was obtained in the same manner as in Example 1-2.

Example 39: Synthesis of 2-[[4-[(E)-2-[5-[(E)-2-(2-furyl)vinyl]-1H-pyrazol-3-yl]vinyl]-3-methoxyphenoxy]methyl]pyridine Example 39-1: Synthesis of (1E,6E)-1-(2-furyl)-7-[2-methoxy-4-(2-pyridylmethoxy)phenyl]hepta-1,6-diene-3,5-dione The title compound was obtained in the same manner as in Example 1-1.

Example 39-2: Synthesis of 2-[[4-[(E)-2-[5-[(E)-2-(2-furyl)vinyl]-1H-pyrazol-3-yl]vinyl]-3-methoxyphenoxy]methyl]pyridine The title compound was obtained in the same manner as in Example 1-2.

Example 40: Synthesis of 2-[[3-methoxy-4-[(E)-2-[5-[(E)-2-(5-methyl-2-furyl)vinyl]-1H-pyrazol-3-yl]vinyl]phenoxy]methyl]pyridine Example 40-1: Synthesis of (1E,6E)-1-[2-methoxy-4-(2-pyridylmethoxy)phenyl]-7-(5-methyl-2-furyl)hepta-1,6-diene-3,5-dione The title compound was obtained in the same manner as in Example 1-1.

Example 40-2: Synthesis of 2-[[3-methoxy-4-[(E)-2-[5-[(E)-2-(5-methyl-2-furyl)vinyl]-1H-pyrazol-3-yl]vinyl]phenoxy]methyl]pyridine The title compound was obtained in the same manner as in Example 1-2.

Example 41: Synthesis of 2-[[4-[(E)-2-[5-[(E)-2-(4,5-dimethyl-2-furyl)vinyl]-1H-pyrazol-3-yl]vinyl]-3-methoxyphenoxy]methyl]pyridine Example 41-1: Synthesis of (1E,6E)-1-(4,5-dimethyl-2-furyl)-7-[2-methoxy-4-(2-pyridylmethoxy)phenyl]hepta-1,6-diene-3,5-dione The title compound was obtained in the same manner as in Example 1-1.

Example 41-2: Synthesis of 2-[[4-[(E)-2-[5-[(E)-2-(4,5-dimethyl-2-furyl)vinyl]-1H-pyrazol-3-yl]vinyl]-3-methoxyphenoxy]methyl]pyridine The title compound was obtained in the same manner as in Example 1-2.

Example 42: Synthesis of 2-[[3-methoxy-4-[(E)-2-[5-[(E)-2-(2-methylpyrazol-3-yl)vinyl]-1H-pyrazol-3-yl]vinyl]phenoxy]methyl]pyridine Example 42-1: Synthesis of (1E,6E)-1-[2-methoxy-4-(2-pyridylmethoxy)phenyl]-7-(2-methylpyrazol-3-yl)hepta-1,6-diene-3,5-dione The title compound was obtained in the same manner as in Example 1-1.

Example 42-2: Synthesis of 2-[[3-methoxy-4-[(E)-2-[5-[(E)-2-(2-methylpyrazol-3-yl)vinyl]-1H-pyrazol-3-yl]vinyl]phenoxy]methyl]pyridine The title compound was obtained in the same manner as in Example 1-2.

Example 43: Synthesis of 1-methyl-6-[(E)-2-[3-[(E)-2-[4-(4-methyl-1,4-diazepan-1-yl)phenyl]vinyl]-1H-pyrazol-5-yl]vinyl]indole Example 43-1: Synthesis of (1E,6E)-1-[4-(4-methyl-1,4-diazepan-1-yl)phenyl]-7-(1-methylindol-6-yl)hepta-1,6-diene-3,5-dione The title compound was obtained in the same manner as in Example 1-1.

Example 43-2: Synthesis of 1-methyl-6-[(E)-2-[3-[(E)-2-[4-(4-methyl-1,4-diazepan-1-yl)phenyl]vinyl]-1H-pyrazol-5-yl]vinyl]indole The title compound was obtained in the same manner as in Example 1-2.

Example 44: Synthesis of 6-[(E)-2-[3-[(E)-2-[2-methoxy-4-[2-(2-pyridyl)ethoxy]phenyl]vinyl]-1H-pyrazol-5-yl]vinyl]-1-methylindole Example 44-1: Synthesis of (1E,6E)-1-[2-methoxy-4-[2-(2-pyridyl)ethoxy]phenyl]-7-(1-methylindol-6-yl)hepta-1,6-diene-3,5-dione The title compound was obtained in the same manner as in Example 1-1.

Example 44-2: Synthesis of 6-[(E)-2-[3-[(E)-2-[2-methoxy-4-[2-(2-pyridyl)ethoxy]phenyl]vinyl]-1H-pyrazol-5-yl]vinyl]-1-methylindole The title compound was obtained in the same manner as in Example 1-2.

Example 45: Synthesis of 6-[(E)-2-[3-[(E)-2-[2,6-dimethoxy-4-(2-pyridylmethoxy)phenyl]vinyl]-1H-pyrazol-5-yl]vinyl]-1-methylindole Example 45-1: Synthesis of (1E,6E)-1-[2,6-dimethoxy-4-(2-pyridylmethoxy)phenyl]-7-(1-methylindol-6-yl)hepta-1,6-diene-3,5-dione The title compound was obtained in the same manner as in Example 1-1.

Example 45-2: Synthesis of 6-[(E)-2-[3-[(E)-2-[2,6-dimethoxy-4-(2-pyridylmethoxy)phenyl]vinyl]-1H-pyrazol-5-yl]vinyl]-1-methylindole The title compound was obtained in the same manner as in Example 1-2.

Example 46: Synthesis of 6-[(E)-2-[3-[(E)-2-[3-fluoro-4-(2-pyridylmethoxy)phenyl]vinyl]-1H-pyrazol-5-yl]vinyl]-1-methylindole Example 46-1: Synthesis of (1E,6E)-1-[3-fluoro-4-(2-pyridylmethoxy)phenyl]-7-(1-methylindol-6-yl)hepta-1,6-diene-3,5-dione The title compound was obtained in the same manner as in Example 1-1.

Example 46-2: Synthesis of 6-[(E)-2-[3-[(E)-2-[3-fluoro-4-(2-pyridylmethoxy)phenyl]vinyl]-1H-pyrazol-5-yl]vinyl]-1-methylindole The title compound was obtained in the same manner as in Example 1-2.

Example 47: Synthesis of 4-[[4-[(E)-2-[5-[(E)-2-(1H-indol-6-yl)vinyl]-1H-pyrazol-3-yl]vinyl]phenyl]methyl]morpholine Example 47-1: Synthesis of (1E,6E)-1-(1H-indol-6-yl)-7-[4-(morpholinomethyl)phenyl]hepta-1,6-diene-3,5-dione The title compound was obtained in the same manner as in Example 1-1.

Example 47-2: Synthesis of 4-[[4-[(E)-2-[5-[(E)-2-(1H-indol-6-yl)vinyl]-1H-pyrazol-3-yl]vinyl]phenyl]methyl]morpholine The title compound was obtained in the same manner as in Example 1-2.

Example 48: Synthesis of 4-[2-[4-[(E)-2-[5-[(E)-2-(1H-indol-6-yl)vinyl]-1H-pyrazol-3-yl]vinyl]phenyl]ethyl]morpholine Example 48-1: Synthesis of (1E,6E)-1-(1H-indol-6-yl)-7-[4-(2-morpholinoethyl)phenyl]hepta-1,6-diene-3,5-dione The title compound was obtained in the same manner as in Example 1-1.

Example 48-2: Synthesis of 4-[2-[4-[(E)-2-[5-[(E)-2-(1H-indol-6-yl)vinyl]-1H-pyrazol-3-yl]vinyl]phenyl]ethyl]morpholine The title compound was obtained in the same manner as in Example 1-2.

Example 49: Synthesis of 4-[3-[4-[(E)-2-[5-[(E)-2-(1H-indol-6-yl)vinyl]-1H-pyrazol-3-yl]vinyl]phenyl]propyl]morpholine Example 49-1: Synthesis of (1E,6E)-1-(1H-indol-6-yl)-7-[4-(3-morpholinopropyl)phenyl]hepta-1,6-diene-3,5-dione The title compound was obtained in the same manner as in Example 1-1.

Example 49-2: Synthesis of 4-[3-[4-[(E)-2-[5-[(E)-2-(1H-indol-6-yl)vinyl]-1H-pyrazol-3-yl]vinyl]phenyl]propyl]morpholine The title compound was obtained in the same manner as in Example 1-2.

Example 50: Synthesis of 6-[(E)-2-[3-[(E)-2-[4-[(4-methylpiperazin-1-yl)methyl]phenyl]vinyl]-1H-pyrazol-5-yl]vinyl]-1H-indole

Example 50-1: Synthesis of (1E,6E)-1-(1H-indol-6-yl)-7-[4-[(4-methylpiperazin-1-yl)methyl]phenyl]hepta-1,6-diene-3,5-dione The title compound was obtained in the same manner as in Example 1-1.

Example 50-2: Synthesis of 6-[(E)-2-[3-[(E)-2-[4-[(4-methylpiperazin-1-yl)methyl]phenyl]vinyl]-1H-pyrazol-5-yl]vinyl]-1H-indole The title compound was obtained in the same manner as in Example 1-2.

Example 51: Synthesis of 6-[(E)-2-[3-[(E)-2-[4-[2-(4-methylpiperazin-1-yl)ethyl]phenyl]vinyl]-1H-pyrazol-5-yl]vinyl]-1H-indole

Example 51-1: Synthesis of (1E,6E)-1-(1H-indol-6-yl)-7-[4-[2-(4-methylpiperazin-1-yl)ethyl]phenyl]hepta-1,6-diene-3,5-dione The title compound was obtained in the same manner as in Example 1-1.

Example 51-2: Synthesis of 6-[(E)-2-[3-[(E)-2-[4-[2-(4-methylpiperazin-1-yl)ethyl]phenyl]vinyl]-1H-pyrazol-5-yl]vinyl]-1H-indole The title compound was obtained in the same manner as in Example 1-2.

Example 52: Synthesis of 4-[2-[2-[(E)-2-[5-[(E)-2-(1H-indol-6-yl)vinyl]-1H-pyrazol-3-yl]vinyl]phenoxy]ethyl]morpholine

Example 52-1: Synthesis of (1E,6E)-1-(1H-indol-6-yl)-7-[2-(2-morpholinoethoxy)phenyl]hepta-1,6-diene-3,5-dione The title compound was obtained in the same manner as in Example 1-1.

Example 52-2: Synthesis of 4-[2-[2-[(E)-2-[5-[(E)-2-(1H-indol-6-yl)vinyl]-1H-pyrazol-3-yl]vinyl]phenoxy]ethyl]morpholine The title compound was obtained in the same manner as in Example 1-2.

Example 53: Synthesis of 4-[2-[3-[(E)-2-[5-[(E)-2-(1H-indol-6-yl)vinyl]-1H-pyrazol-3-yl]vinyl]phenoxy]ethyl]morpholine

Example 53-1: Synthesis of (1E,6E)-1-(1H-indol-6-yl)-7-[3-(2-morpholinoethoxy)phenyl]hepta-1,6-diene-3,5-dione The title compound was obtained in the same manner as in Example 1-1.

Example 53-2: Synthesis of 4-[2-[3-[(E)-2-[5-[(E)-2-(1H-indol-6-yl)vinyl]-1H-pyrazol-3-yl]vinyl]phenoxy]ethyl]morpholine The title compound was obtained in the same manner as in Example 1-2.

Example 54: Synthesis of 6-[(E)-2-[3-[(E)-2-[2-methoxy-4-[2-(2-pyridyl)ethoxy]phenyl]vinyl]-1H-pyrazol-5-yl]vinyl]-1H-indole

Example 54-1: Synthesis of (1E,6E)-1-(1H-indol-6-yl)-7-[2-methoxy-4-[2-(2-pyridyl)ethoxy]phenyl]hepta-1,6-diene-3,5-dione The title compound was obtained in the same manner as in Example 1-1.

Example 54-2: Synthesis of 6-[(E)-2-[3-[(E)-2-[2-methoxy-4-[2-(2-pyridyl)ethoxy]phenyl]vinyl]-1H-pyrazol-5-yl]vinyl]-1H-indole The title compound was obtained in the same manner as in Example 1-2.

Example 55: Synthesis of 4-[2-[4-[(E)-2-[5-[(E)-2-(2,3-dihydro-1,4-benzodioxin-6-yl)vinyl]-1H-pyrazol-3-yl]vinyl]-3-methoxyphenoxy]ethyl]morpholine

Example 55-1: Synthesis of (E)-6-(2,3-dihydro-1,4-benzodioxin-6-yl)hex-5-ene-2,4-dione The title compound was obtained in the same manner as in Example 6-1.

Example 55-2: Synthesis of (1E,6E)-1-(2,3-dihydro-1,4-benzodioxin-6-yl)-7-[2-methoxy-4-(2-morpholinoethoxy)phenyl]hepta-1,6-diene-3,5-dione The title compound was obtained in the same manner as in Example 1-1.

Example 55-3: Synthesis of 4-[2-[4-[(E)-2-[5-[(E)-2-(2,3-dihydro-1,4-benzodioxin-6-yl)vinyl]-1H-pyrazol-3-yl]vinyl]-3-methoxyphenoxy]ethyl]morpholine The title compound was obtained in the same manner as in Example 1-2.

Example 56: Synthesis of 4-[2-[3-methoxy-4-[(E)-2-[3-[(E)-2-[2-methoxy-4-(2-morpholinoethoxy)phenyl]vinyl]-1H-pyrazol-5-yl]vinyl]phenoxy]ethyl]morpholine Example 56-1: Synthesis of (1E,6E)-1,7-bis[2-methoxy-4-(2-morpholinoethoxy)phenyl]hepta-1,6-diene-3,5-dione The title compound was obtained in the same manner as in Example 5-1.

Example 56-2: Synthesis of 4-[2-[3-methoxy-4-[(E)-2-[3-[(E)-2-[2-methoxy-4-(2-morpholinoethoxy)phenyl]vinyl]-1H-pyrazol-5-yl]vinyl]phenoxy]ethyl]morpholine The title compound was obtained in the same manner as in Example 1-2.

Example 57: Synthesis of 1-methyl-2-[(E)-2-[3-[(E)-2-[4-(2-pyridylmethoxy)phenyl]vinyl]-1H-pyrazol-5-yl]vinyl]indole Example 57-1: Synthesis of (1E,6E)-1-(1-methylindol-2-yl)-7-[4-(2-pyridylmethoxy)phenyl]hepta-1,6-diene-3,5-dione The title compound was obtained in the same manner as in Example 1-1.

Example 57-2: Synthesis of 1-methyl-2-[(E)-2-[3-[(E)-2-[4-(2-pyridylmethoxy)phenyl]vinyl]-1H-pyrazol-5-yl]vinyl]indole The title compound was obtained in the same manner as in Example 1-2.

Example 58: Synthesis of 5-[(E)-2-[3-[(E)-2-[2-methoxy-4-(2-pyridylmethoxy)phenyl]vinyl]-1H-pyrazol-5-yl]vinyl]-1-methylindole Example 58-1: Synthesis of (1E,6E)-1-[2-methoxy-4-(2-pyridylmethoxy)phenyl]-7-(1-methylindol-5-yl)hepta-1,6-diene-3,5-dione The title compound was obtained in the same manner as in Example 1-1.

Example 58-2: Synthesis of 5-[(E)-2-[3-[(E)-2-[2-methoxy-4-(2-pyridylmethoxy)phenyl]vinyl]-1H-pyrazol-5-yl]vinyl]-1-methylindole The title compound was obtained in the same manner as in Example 1-2.

Example 59: Synthesis of 1-methyl-6-[(E)-2-[3-[(E)-2-[2-methyl-4-(2-pyridylmethoxy)phenyl]vinyl]-1H-pyrazol-5-yl]vinyl]indole Example 59-1: Synthesis of (1E,6E)-1-(1-methylindol-6-yl)-7-[2-methyl-4-(2-pyridylmethoxy)phenyl]hepta-1,6-diene-3,5-dione The title compound was obtained in the same manner as in Example 1-1.

Example 59-2: Synthesis of 1-methyl-6-[(E)-2-[3-[(E)-2-[2-methyl-4-(2-pyridylmethoxy)phenyl]vinyl]-1H-pyrazol-5-yl]vinyl]indole The title compound was obtained in the same manner as in Example 1-2.

The structural formulas and analytical data of the compounds obtained in the above Examples are shown in the tables below.

Ex.: example; St.: chemical structure; Dat.: analytical data

TABLE 2

| Ex. | St. Dat. |
|---|---|
| 1-1 | 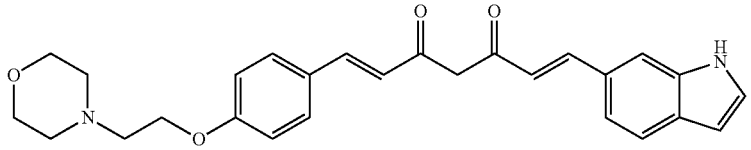 [SMILES: O=C(/C=C/c1ccc(OCCN2CCOCC2)cc1)CC(=O)/C=C/c1ccc2cc[nH]c2c1]<br>$^1$H NMR (δ, CDCl$_3$): 2.56-2.61 (m, 4H), 2.82 (t, 2H, J = 5.7 Hz), 3.72-3.76 (m, 4H), 4.15 (t, 2H, J = 5.7 Hz), 5.81 (s, 1H), 6.51 (d, 1H, J = 16.0 Hz), 6.56-6.58 (m, 1H), 6.64 (d, 1H, J = 16.0 Hz), 6.92 (d, 2H, J = 8.8 Hz), 7.28-7.30 (m, 1H), 7.40 (dd, 1H, J = 1.3 Hz, 8.2 Hz), 7.50 (d, 2H, J = 8.8 Hz), 7.56 (s, 1H), 7.62 (d, 1H, J = 16.0 Hz), 7.63 (d, 1H, J = 8.2 Hz), 7.79 (d, 1H, J = 16.0 Hz), 8.30 (s, 1H), 16.07 (brs, 1H)<br>MS (EI) m/z 444 (M$^+$). |
| 1-2 | 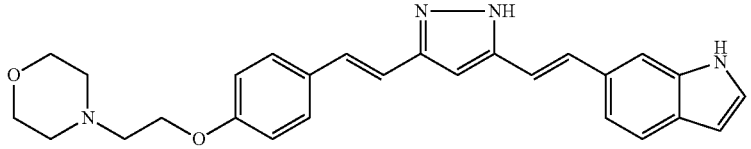 [SMILES: C(=C\c1cc(/C=C/c2ccc3cc[nH]c3c2)[nH]n1)/c1ccc(OCCN2CCOCC2)cc1]<br>$^1$H NMR (δ, CDCl$_3$): 2.55-2.60 (m, 4H), 2.80 (t, 2H, J = 5.7 Hz), 3.72-3.75 (m, 4H), 4.11 (t, 2H, J = 5.7 Hz), 6.52-6.54 (m, 1H), 6.60 (s, 1H), 6.87 (d, 2H, J = 8.7 Hz), 6.92 (d, 1H, J = 16.4 Hz), 7.01-7.06 (m, 2H), 7.18-7.20 (m, 1H), 7.19 (d, 1H, J = 16.4 Hz), 7.31 (dd, 1H, J = 1.4 Hz, 8.3 Hz), 7.40 (d, 2H, J = 8.7 Hz), 7.43-7.45 (m, 1H), 7.60 (d, 1H, J = 8.3 Hz), 8.13 (s, 1H), 9.32-11.42 (br, 1H)<br>MS (EI) m/z 440 (M$^+$). |

TABLE 2-continued
| St. Ex. Dat. | |
|---|---|
| 2-1 | 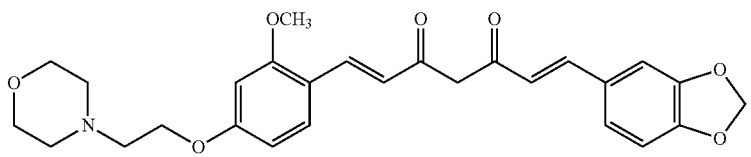 [SMILES: COc1cc(OCCN2CCOCC2)ccc1/C=C/C(=O)CC(=O)/C=C/c1ccc2c(c1)OCO2] |
MS (EI) m/z 479 (M+)
| 2-2 | 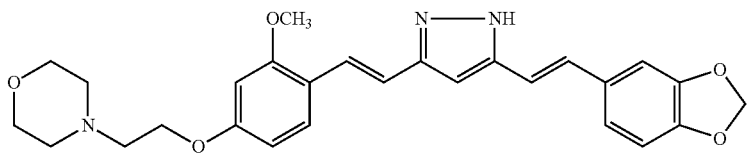 [SMILES: COc1cc(OCCN2CCOCC2)ccc1/C=C/c1cc(/C=C/c2ccc3c(c2)OCO3)[nH]n1] |
|---|---|
$^1$H NMR (δ, CDCl$_3$): 2.61-2.74 (m, 4H), 2.84-2.93 (m, 2H), 3.76-3.83 (m, 4H), 3.87 (s, 3H), 4.16-4.22 (m, 2H), 5.97 (s, 2H), 6.48-6.52 (m, 2H), 6.58 (s, 1H), 6.79 (d, 1H J = 7.8 Hz), 6.88 (d, 1H, J = 16.5 Hz), 6.91-6.97 (m, 2H), 7.00 (d, 1H, J = 16.5 Hz), 7.03 (d, 1H, J = 1.4 Hz), 7.29 (d, 1H, J = 16.5 Hz), 7.43 (d, 1H, J = 8.2 Hz)
MS (EI) m/z 475 (M+).
TABLE 3
| 3-1 | 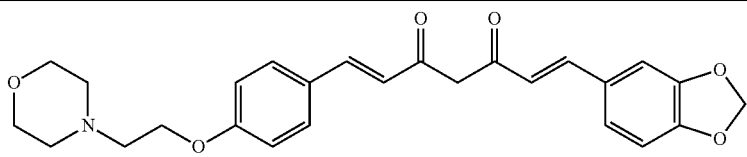 |
|---|---|
MS (EI) m/z 449 (M+)
| 3-2 | 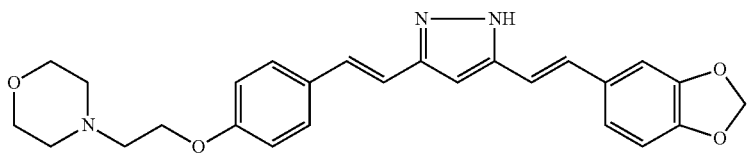 [SMILES: C(=C\c1cc(/C=C/c2ccc3c(c2)OCO3)[nH]n1)/c1ccc(OCCN2CCOCC2)cc1] |
|---|---|
$^1$H NMR (δ, CDCl$_3$): 2.56-2.60 (m, 4H), 2.81 (t, 2H, J = 5.7 Hz), 3.74 (m, 4H), 4.14 (t, 2H, J = 5.7 Hz), 5.98 (s, 2H), 6.57 (s, 1H), 6.79 (d, 1H, J = 7.8 Hz), 6.84-6.94 (m, 5H), 6.97-7.04 (m, 3H), 7.40-7.43 (m, 2H), 9.48-11.04 (br, 1H)
MS (EI) m/z 445 (M+).
TABLE 4
| 4-1 | 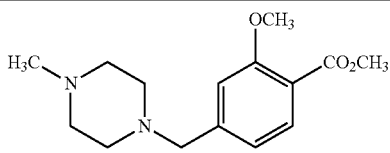 |
|---|---|
$^1$H NMR (δ, CDCl$_3$): 2.29 (s, 3H), 2.47 (brs, 8H), 3.52 (s, 2H), 3.88 (s, 3H), 3.91 (s, 3H), 6.94 (d, 1H, J = 7.9 Hz), 7.00 (s, 1H), 7.74 (d, 1H, J = 7.9 Hz)
| 4-2 | 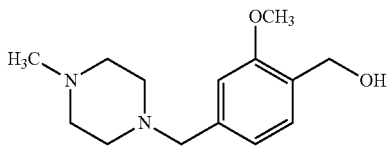 [SMILES: COc1cc(CN2CCN(C)CC2)ccc1CO] |
|---|---|
$^1$H NMR (δ, CDCl$_3$): 2.28 (s, 3H), 2.47 (brs, 8H), 3.49 (s, 2H), 3.87 (s, 3H), 4.66 (s, 2H), 6.86-6.92 (m, 2H), 7.20 (d, 1H, J = 7.7 Hz)

TABLE 4-continued 4-3

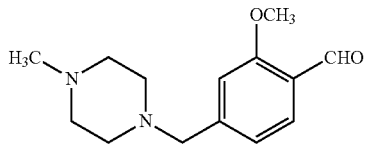 [SMILES: COc1cc(CN2CCN(C)CC2)ccc1C=O]

¹H NMR (δ, CDCl₃): 2.30 (s, 3H), 2.48 (brs, 8H), 3.53 (s, 2H), 3.94 (s, 3H), 6.97-7.02 (m, 2H), 7.77 (d, 1H, J = 7.7 Hz), 10.42 (s, 1H)

4-4

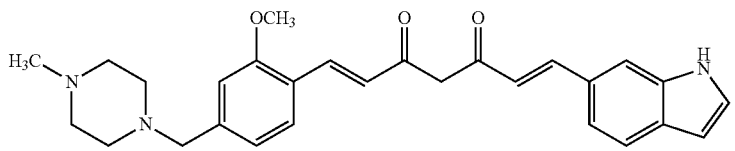 [SMILES: COc1cc(CN2CCN(C)CC2)ccc1/C=C/C(=O)CC(=O)/C=C/c1ccc2cc[nH]c2c1]

¹H NMR (δ, DMSO-d₆): 2.16 (s, 3H), 2.37 (brs, 8H), 3.48 (s, 2H), 3.89 (s, 3H), 6.14 (s, 1H), 6.47-6.51 (m, 1H), 6.84-6.99 (m, 3H), 7.02 (s, 1H), 7.43 (d, 1H, J = 8.3 Hz), 7.48-7.51 (m, 1H), 7.60 (d, 1H, J = 8.3 Hz), 7.66-7.74 (m, 2H), 7.79 (d, 1H, J = 15.8 Hz), 7.85 (d, 1H, J = 15.9 Hz), 11.41 (brs, 1H)
MS (ESI) m/z 459 (M⁺2H)⁺, 915 (2M + H)⁺.

4-5

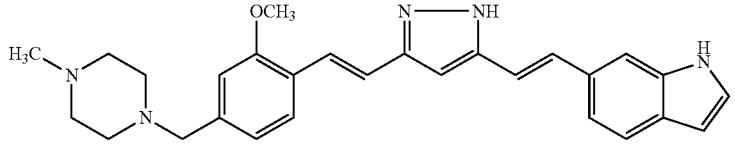 [SMILES: COc1cc(CN2CCN(C)CC2)ccc1/C=C/c1cc(/C=C/c2ccc3cc[nH]c3c2)[nH]n1]

¹H NMR (δ, CDCl₃): 2.31 (s, 3H), 2.50 (brs, 8H), 3.51 (s, 2H), 3.91 (s, 3H), 6.54-6.56 (m, 1H), 6.67 (s, 1H), 6.91-6.94 (m, 2H), 7.05 (d, 1H, J = 16.6 Hz), 7.07 (d, 1H, J = 16.6 Hz), 7.18-7.28 (m, 2H), 7.34 (dd, 1H, J = 1.5 Hz, 8.5 Hz), 7.38 (d, 1H, J = 16.6 Hz), 7.47-7.50 (m, 2H), 7.62 (d, 1H, J = 8.0 Hz), 8.21 (brs, 1H)

TABLE 5

5-1

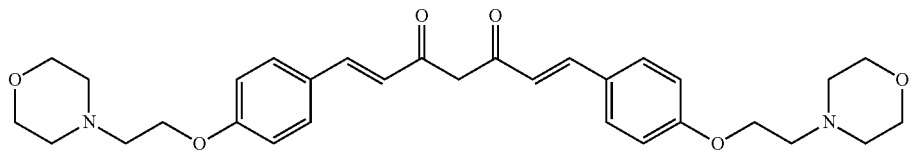 [SMILES: O=C(/C=C/c1ccc(OCCN2CCOCC2)cc1)CC(=O)/C=C/c1ccc(OCCN2CCOCC2)cc1]

¹H NMR (δ, CDCl₃): 2.56-2.61 (m, 8H), 2.81 (t, 4H, J = 5.7 Hz), 3.72-3.76 (m, 8H), 4.15 (t, 4H, J = 5.7 Hz), 5.77 (s, 1H), 6.49 (d, 2H, J = 16.0 Hz), 6.92 (d, 4H, J = 8.9 Hz), 7.50 (d, 4H, J = 8.9 Hz), 7.61 (d, 2H, J = 16.0 Hz), 16.00 (brs, 1H)
MS (EI) m/z 534 (M⁺).

5-2

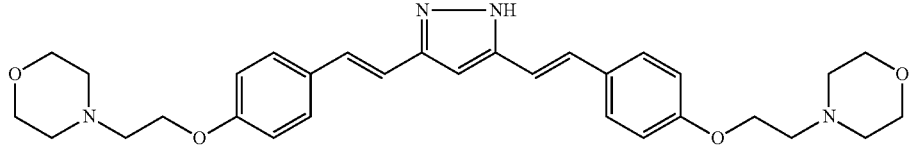 [SMILES: C(=C\c1cc(/C=C/c2ccc(OCCN3CCOCC3)cc2)[nH]n1)/c1ccc(OCCN2CCOCC2)cc1]

¹H NMR (δ, CDCl₃): 2.56-2.61 (m, 8H), 2.81 (t, 4H, J = 5.7 Hz), 3.72-3.76 (m, 8H), 4.13 (t, 4H, J = 5.7 Hz), 6.57 (s, 1H), 6.89 (d, 2H, J = 16.4 Hz), 6.89 (d, 4H, J = 8.8 Hz), 7.02 (d, 2H, J = 16.4 Hz), 7.41 (d, 4H, J = 8.8 Hz)
MS (EI) m/z 530 (M⁺).

6-1

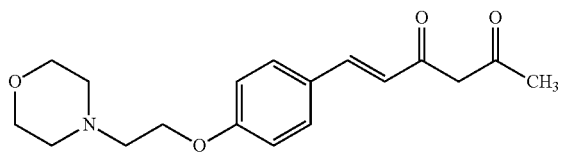 [SMILES: CC(=O)CC(=O)/C=C/c1ccc(OCCN2CCOCC2)cc1]

¹H NMR (δ, CDCl₃): 2.16 (s, 3H), 2.56-2.60 (m, 4H), 2.81 (t, 2H, J = 5.7 Hz), 3.72-3.76 (m, 4H), 4.14 (t, 2H, J = 5.7 Hz), 5.62 (s, 1H), 6.34 (d, 1H, J = 15.7 Hz), 6.89-6.93 (m, 2H), 7.45-7.49 (m, 2H), 7.55 (d, 1H, J = 15.8 Hz)
MS (ESI) m/z 318(M + H)⁺.

TABLE 5-continued
6-2
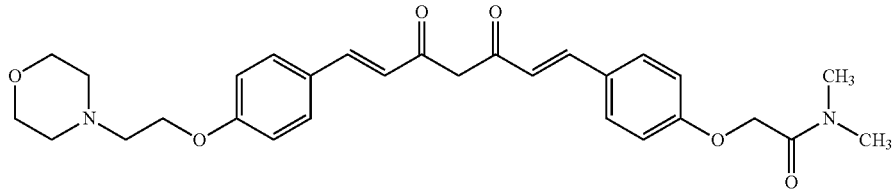 [SMILES: CN(C)C(=O)COc1ccc(/C=C/C(=O)CC(=O)/C=C/c2ccc(OCCN3CCOCC3)cc2)cc1]
$^1$H NMR (δ, CDCl$_3$): 2.57-2.61 (m, 4H), 2.82 (t, 2H, J = 5.7 Hz), 2.99 (s, 3H), 3,10 (s, 3H), 3.72-3.77 (m, 4H), 4.15 (t, 2H, J = 5.7 Hz), 4.74 (s, 2H), 5.79 (s, 1H), 6.50 (d, 2H, J = 15.7 Hz), 6.90-6.99 (m, 4H), 7.48-7.54 (m, 4H), 7.61 (d, 1H, J = 15.8 Hz), 7.62 (d, 1H, J = 15.8 Hz)
MS (ESI) m/z 508 (M + 2H)$^+$.
6-3
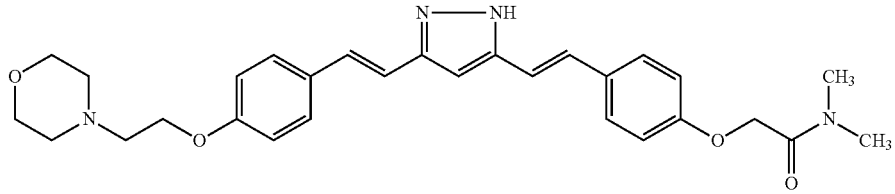 [SMILES: CN(C)C(=O)COc1ccc(/C=C/c2cc(/C=C/c3ccc(OCCN4CCOCC4)cc3)n[nH]2)cc1]
$^1$H NMR (δ, DMSO-d$_6$): 2.45-2.52 (m, 4H), 2.69 (t, 2H, J = 5.8 Hz), 2.85 (s, 3H), 3.00 (s, 3H), 3.56-3.60 (m, 4H), 4.10 (t, 2H, J = 5.7 Hz), 4.83 (s, 2H), 6.67 (s, 1H), 6.87-7.17 (m, 8H), 7.43-7.52 (m, 4H), 12.89 (s, 1H)
TABLE 6
7-1
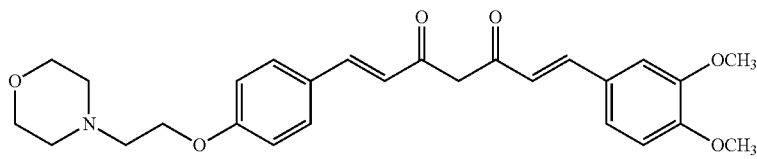 [SMILES: COc1ccc(/C=C/C(=O)CC(=O)/C=C/c2ccc(OCCN3CCOCC3)cc2)cc1OC]
$^1$H NMR (δ, CDCl$_3$): 2.56-2.62 (m, 4H), 2.82 (t, 2H, J = 5.7 Hz), 3.72-3.77 (m, 4H), 3.927 (s, 3H), 3.940 (s, 3H), 4.15 (t, 2H, J = 5.6 Hz), 5.80 (s, 1H), 6.50 (d, 2H, J = 15.8 Hz), 6.86-6.95 (m, 3H), 7.07-7.10 (m, 1H), 7.15 (dd, 1H, J = 1.9, 8.3 Hz), 7.48-7.53 (m, 2H), 7.61 (d, 1H, J = 15.8 Hz), 7.62 (d, 1H, J = 15.9 Hz)
MS (ESI) m/z 466 (M + H)$^+$.
7-2
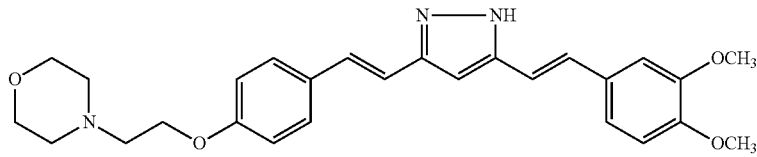 [SMILES: COc1ccc(/C=C/c2cc(/C=C/c3ccc(OCCN4CCOCC4)cc3)n[nH]2)cc1OC]
$^1$H NMR (δ, CDCl$_3$): 2.57-2.61 (m, 4H), 2.81 (t, 2H, J = 5.8 Hz), 3.72-3.77 (m, 4H), 3.876 (s, 3H), 3.884 (s, 3H), 4.11 (t, 2H, J = 5.7 Hz), 6.60 (s, 1H), 6.78-7.08 (m, 9H), 7.35-7.40 (m, 2H)
8-1
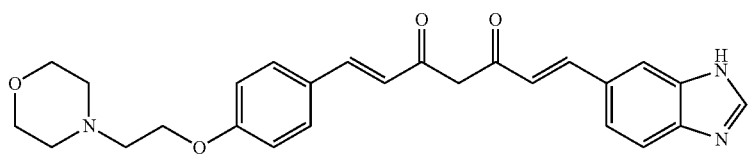 [SMILES: O=C(/C=C/c1ccc(OCCN2CCOCC2)cc1)CC(=O)/C=C/c1ccc2nc[nH]c2c1]
MS (ESI) m/z 446 (M + H)$^+$.

TABLE 6-continued
8-2 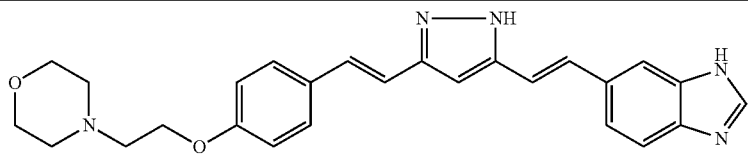
$^1$H NMR (δ, DMSO-$d_6$): 2.45-2.53 (m, 4H), 2.69 (t, 2H, J = 5.6 Hz), 3.56-3.61 (m, 4H), 4.08-4.13 (m, 2H), 6.72 (s, 1H), 6.90-7.35 (m, 6H), 7.42-7.85 (m, 5H), 8.19-8.26 (m, 1H), 12.49 (brs, 1H), 12.92 (brs, 1H)
TABLE 7
9-1 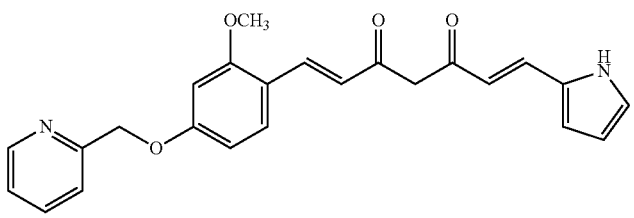 [SMILES: COc1cc(OCc2ccccn2)ccc1/C=C/C(=O)CC(=O)/C=C/c1ccc[nH]1]
MS (EI) m/z 402 (M$^+$).
9-2 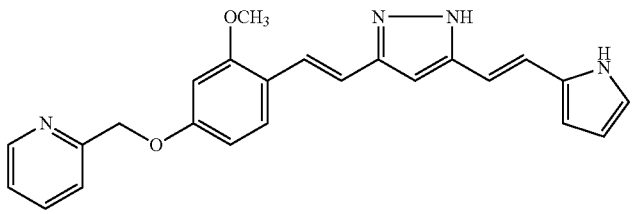 [SMILES: COc1cc(OCc2ccccn2)ccc1/C=C/c1cc(/C=C/c2ccc[nH]2)[nH]n1]
$^1$H NMR (δ, acetone-$d_6$): 3.90 (s, 3H), 5.23 (s, 2H), 6.10-6.13 (m, 1H), 6.26-6.28 (m, 1H), 6.56 (s, 1H), 6.65 (dd, 1H, J = 2.6 Hz, 8.4 Hz), 6.74 (d, 1H, J = 2.6 Hz), 6.77 (d, 1H, J = 16.8 Hz), 6.82-6.84 (m, 1H), 7.03 (d, 1H, J = 16.8 Hz), 7.06 (d, 1H, J = 16.8 Hz), 7.29-7.33 (m, 1H), 7.35 (d, 1H, J = 16.8 Hz), 7.51 (d, 1H, J = 8.4 Hz), 7.56 (br d, 1H, J = 7.7), 7.82 (dt, 1H, J = 1.8 Hz, 7.7 Hz), 8.57-8.60 (m, 1H), 10.33 (brs, 1H)
MS (EI) m/z 398 (M$^+$).
10-1 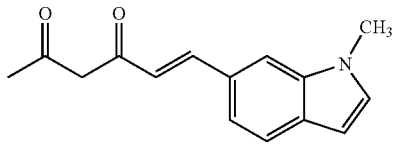 [SMILES: CC(=O)CC(=O)/C=C/c1ccc2ccn(C)c2c1]
MS (EI) m/z 241 (M$^+$).
10-2 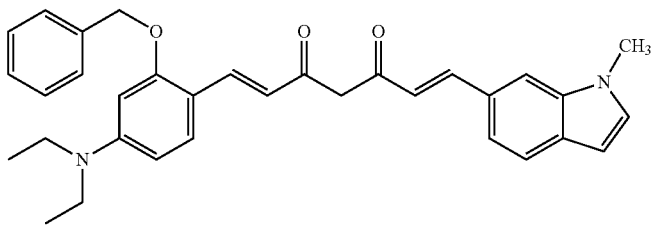 [SMILES: CCN(CC)c1ccc(/C=C/C(=O)CC(=O)/C=C/c2ccc3ccn(C)c3c2)c(OCc2ccccc2)c1]
MS (EI) m/z 506 (M$^+$).

TABLE 7-continued
10-3
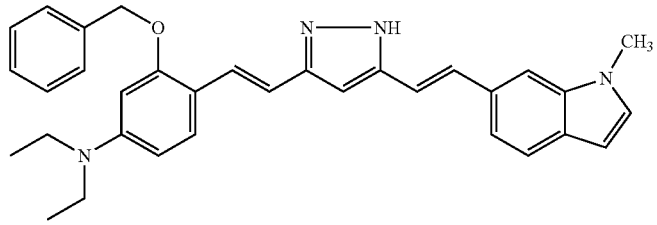 [SMILES: CCN(CC)c1ccc(/C=C/c2cc(/C=C/c3ccc4ccn(C)c4c3)[nH]n2)c(OCc2ccccc2)c1]
¹H NMR (δ, CDCl₃): 1.13 (t, 6H, J = 7.2 Hz), 3.33 (q, 4H, J = 7.2 Hz), 3.80 (s, 3H), 5.16 (s, 2H), 6.21 (d, 1H, J = 2.0 Hz), 6.31 (dd, 1H, J = 2.0 Hz, 8.7 Hz), 6.46 (d, 1H, J = 3.1 Hz), 6.55 (s, 1H), 6.88 (d, 1H, J = 16.4 Hz), 7.05 (d, 1H, J = 3.1 Hz), 7.09 (d, 1H, J = 16.4 Hz), 7.21-7.49 (m, 10H), 7.58 (1H, d, J = 8.2 Hz)
MS (EI) m/z 502 (M⁺).
TABLE 8
11-1
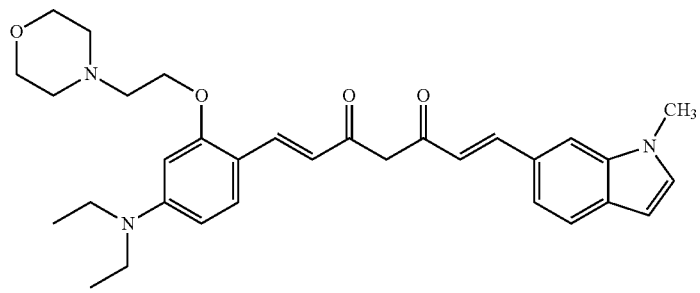 [SMILES: CCN(CC)c1ccc(/C=C/C(=O)CC(=O)/C=C/c2ccc3ccn(C)c3c2)c(OCCN2CCOCC2)c1]
MS (EI) m/z 529 (M+).
11-2
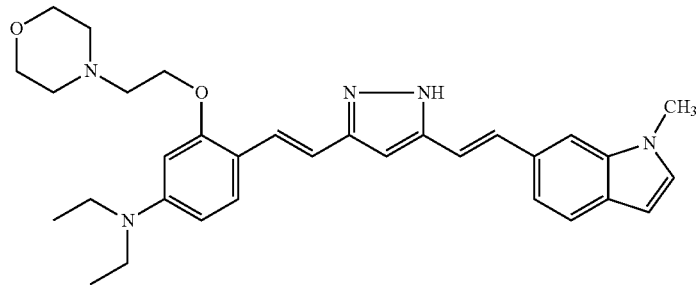 [SMILES: CCN(CC)c1ccc(/C=C/c2cc(/C=C/c3ccc4ccn(C)c4c3)[nH]n2)c(OCCN2CCOCC2)c1]
¹H NMR (δ, CDCl₃): 1.19 (t, 6H, J = 7.2 Hz), 2.66-2.70 (m, 4H), 2.93 (t, 2H, J = 5.9 Hz), 3.38 (q, 4H, J = 7.2 Hz), 3.75-3.81 (m, 7H), 4.20 (t, 2H, J = 5.9 Hz), 6.19 (d, 1H, J = 2.5 Hz), 6.32 (dd, 1H, J = 2.5 Hz, 8.7 Hz), 6.46 (d, 1H, J = 3.1 Hz), 6.55 (s, 1H), 6.88 (d, 1H, J = 16.4 Hz), 7.05 (d, 1H, J = 3.1 Hz), 7.10 (d, 1H, J = 16.4 Hz), 7.24 (d, 1H, J = 16.4 Hz), 7.30 (d, 1H, J = 16.4 Hz), 7.33 (dd, 1H, J = 1.5 Hz, 8.2 Hz), 7.39 (d, 1H, J = 8.7 Hz), 7.43 (brs, 1H), 7.58 (d, 1H, J = 8.2 Hz)
MS (EI) m/z 525 (M⁺).
12-1
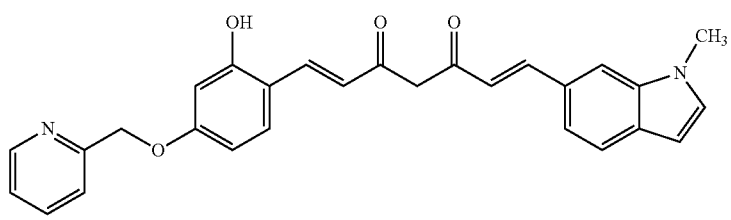 [SMILES: Cn1ccc2ccc(/C=C/C(=O)CC(=O)/C=C/c3ccc(OCc4ccccn4)cc3O)cc21]
MS (EI) m/z 452 (M⁺).

TABLE 8-continued
12-2 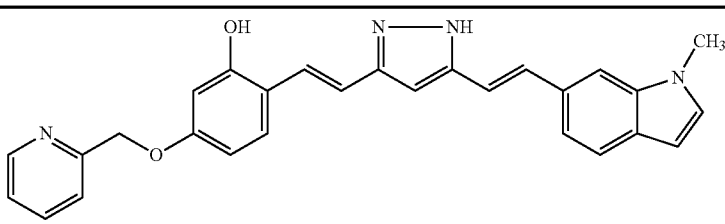
$^1$H NMR (δ, acetone-d$_6$): 3.87 (s, 3H), 5.17 (s, 2H), 6.41 (d, 1H, J = 3.1 Hz), 6.57-6.61 (m, 2H), 6.69 (s, 1H), 7.09 (d, 1H, J = 16.9 Hz), 7.15 (d, 1H, J = 16.4 Hz), 7.23 (d, 1H, J = 3.1 Hz), 7.29-7.33 (m, 2H), 7.34 (d, 1H, J = 16.4 Hz), 7.41 (d, 1H, J = 16.9 Hz), 7.48 (d, 1H, J = 8.2 Hz), 7.52 (br d, 1H, J = 7.7 Hz), 7.54 (d, 1H, J = 8.7 Hz), 7.56 (brs, 1H), 7.81 (dt, 1H, J = 2.1 Hz, 7.7 Hz), 8.56-8.59 (m, 1H), 8.13-9.43 (br, 1H), 11.20-12.53 (br, 1H)
MS (EI) m/z 448 (M$^+$).
TABLE 9
13-1 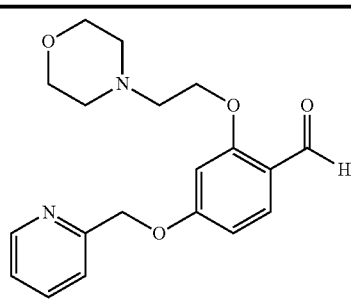
$^1$H NMR (δ, CDCl$_3$): 2.56-2.61 (m, 4H), 2.85 (t, 2H, J = 5.6 Hz), 3.71-3.74 (m, 4H), 4.18 (t, 2H, J = 5.6 Hz), 5.26 (s, 2H), 6.57-6.59 (m, 1H), 6.62-6.65 (m, 1H), 7.24-7.28 (m, 1H), 7.47-7.50 (m, 1H), 7.72-7.76 (m, 1H), 7.81 (d, 1H, J = 8.7 Hz), 8.61-8.63 (m, 1H), 10.31 (s, 1H)
13-2 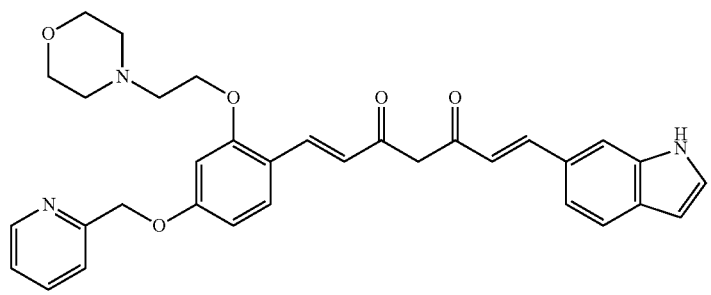 [SMILES: O=C(/C=C/c1ccc2cc[nH]c2c1)CC(=O)/C=C/c1ccc(OCc2ccccn2)cc1OCCN1CCOCC1]
MS (EI) m/z 551 (M$^+$)
13-3 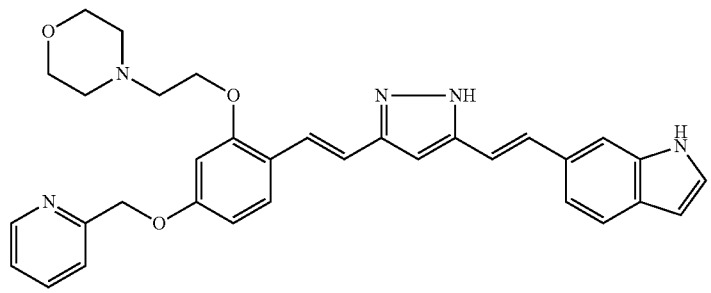 [SMILES: C(=C\c1cc(/C=C/c2ccc(OCc3ccccn3)cc2OCCN2CCOCC2)n[nH]1)/c1ccc2cc[nH]c2c1]
$^1$H NMR (δ, DMSO-d$_6$): 2.49-2.56 (m, 4H), 2.77-2.82 (m, 2H), 3.59-3.63 (m, 4H), 4.17 (t, 2H, J = 5.7 Hz), 5.22 (s, 2H), 6.40-6.44 (m, 1H), 6.61-6.69 (m, 2H), 6.75-6.79 (m, 1H), 6.98-7.10 (m, 2H), 7.20-7.31 (m, 3H), 7.34-7.40 (m, 2H), 7.46-7.57 (m, 4H), 7.84-7.88 (m, 1H), 8.58-8.61 (m, 1H), 11.18 (brs, 1H), 12.87 (brs, 1H)
MS (EI) m/z 547 (M$^+$).

TABLE 10

| Ex. | St. Dat. |
|---|---|
| 14-1 | 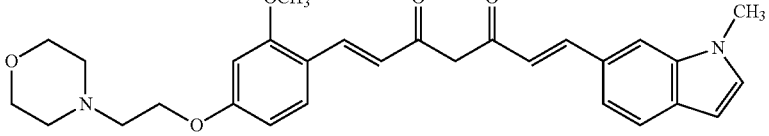<br>1H NMR (δ, CDCl₃): 2.56-2.60 (m, 4H), 2.82 (t, 2H, J = 5.8 Hz), 3.72-3.76 (m, 4H), 3.83 (s, 3H), 3.88 (s, 3H), 4.15 (t, 2H, J = 5.8 Hz), 5.83 (s, 1H), 6.48-6.53 (m, 3H), 6.64 (d, 1H, J = 16.0 Hz), 6.66 (d, 1H, J = 16.0 Hz), 7.12 (d, 1H, J = 3.2 Hz), 7.38 (dd, 1H, J = 1.3, 8.3 Hz), 7.47-7.49 (m, 2H), 7.60 (d, 1H, J = 8.3 Hz), 7.81 (d, 1H, J = 16.0 Hz), 7.90 (d, 1H, J = 16.0 Hz)<br>MS (EI) m/z 488 (M⁺). |
| 14-2 | 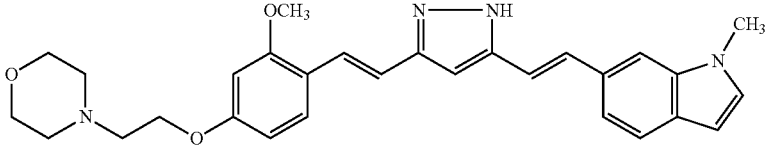 [SMILES: COc1cc(OCCN2CCOCC2)ccc1/C=C/c1cc(/C=C/c2ccc3ccn(C)c3c2)[nH]n1]<br>1H NMR (δ, CDCl₃): 2.59-2.63 (m, 4H), 2.83 (t, 2H, J = 5.7 Hz), 3.75-3.78 (m, 4H), 3.79 (s, 3H), 3.86 (s, 3H), 4.14 (t, 2H, J = 5.7 Hz), 6.45-6.50 (m, 3H), 6.64 (s, 1H), 6.99 (d, 1H, J = 16.6 Hz), 7.06 (d, 1H, J = 3.1 Hz), 7.09 (d, 1H, J = 16.5 Hz), 7.24 (d, 1H, J = 16.6 Hz), 7.30-7.35 (m, 2H), 7.40-7.42 (m, 1H), 7.45 (d, 1H, J = 9.2 Hz), 7.58 (d, 1H, J = 8.2 Hz),<br>MS (EI) m/z 484 (M⁺). |
| 15-1 | 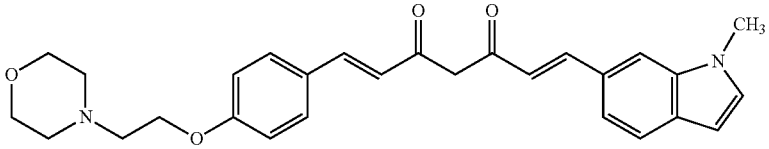 [SMILES: Cn1ccc2ccc(/C=C/C(=O)CC(=O)/C=C/c3ccc(OCCN4CCOCC4)cc3)cc21]<br>MS (EI) m/z 458 (M⁺). |
| 15-2 | 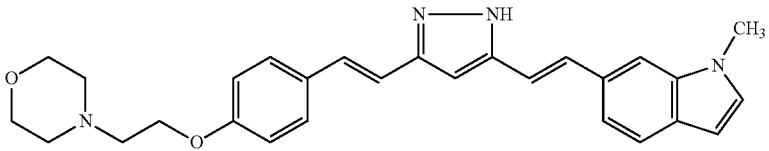 [SMILES: Cn1ccc2ccc(/C=C/c3cc(/C=C/c4ccc(OCCN5CCOCC5)cc4)n[nH]3)cc21]<br>1H NMR (δ, CDCl₃): 2.57-2.61 (m, 4H), 2.82 (t, 2H, J = 5.7 Hz), 3.73-3.76 (m, 4H), 3.80 (s, 3H), 4.14 (t, 2H, J = 5.7 Hz), 6.46-6.47 (m, 1H), 6.61 (s, 1H), 6.88-6.97 (m, 3H), 7.02-7.08 (m, 3H), 7.23 (d, 1H, J = 16.5 Hz), 7.31 (dd, 1H, J = 1.4, 8.3 Hz), 7.40-7.44 (m, 2H), 7.59 (d, 1H, J = 8.3 Hz), 7.77 (d, 1H, J = 8.7 Hz)<br>MS (EI) m/z 454 (M⁺). |

TABLE 11

| 16-1 | 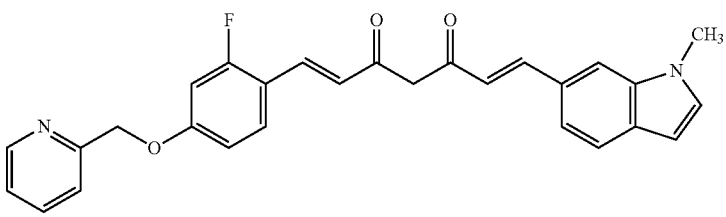 [SMILES: Cn1ccc2ccc(/C=C/C(=O)CC(=O)/C=C/c3ccc(OCc4ccccn4)cc3F)cc21]<br>MS (EI) m/z 454 (M⁺). |
|---|---|

TABLE 11-continued 16-2 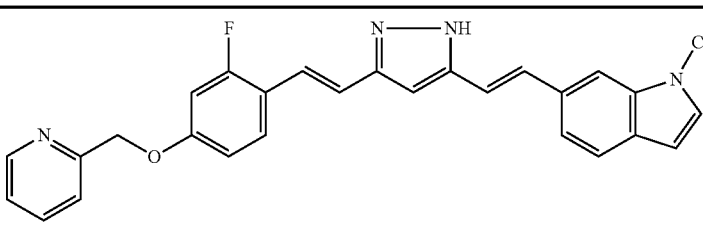

1H NMR (δ, CDCl$_3$): 3.80 (s, 3H), 5.21 (s, 2H), 6.47 (dd, 1H, J = 0.7 Hz, 3.2 Hz), 6.65 (s, 1H), 6.73 (dd, 1H, J = 2.5 Hz, 12.3 Hz), 6.79 (dd, 1H, J = 2.5 Hz, 8.7 Hz), 7.02 (d, 1H, J = 16.7 Hz), 7.05 (d, 1H, J = 16.9 Hz), 7.06 (d, 1H, J = 3.0 Hz), 7.16 (d, 1H, J = 16.7 Hz), 7.21-7.26 (m, 2H), 7.32 (dd, 1H, J = 1.35 Hz, 8.3 Hz), 7.40 (s, 1H), 7.45-7.51 (m, 2H), 7.59 (d, 1H, J = 8.3 Hz), 7.70-7.75 (m, 1H), 8.62 (d, 1H, J = 4.3 Hz)
MS (EI) m/z 450 (M$^+$).

17-1 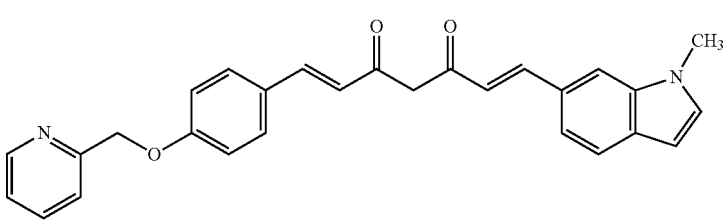 [SMILES: Cn1ccc2ccc(/C=C/C(=O)CC(=O)/C=C/c3ccc(OCc4ccccn4)cc3)cc21]

1H NMR (δ, CDCl$_3$): 3.84 (s, 3H), 5.25 (s, 2H), 5.82 (s, 1H), 6.49-6.53 (m, 2H), 6.67 (d, 1H, J = 15.7 Hz), 7.00-7.02 (m, 2H), 7.13 (d, 1H, J = 3.0 Hz), 7.23-7.27 (m, 1H), 7.39 (dd, 1H, J = 1.2, 8.4 Hz), 7.48-7.53 (m, 4H), 7.60-7.64 (m, 2H), 7.71-7.75 (m, 1H), 7.83 (d, 1H, J = 15.7 Hz), 8.60-8.63 (m, 1H), 16.11 (brs, 1H).
MS (EI) m/z 436 (M$^+$).

17-2 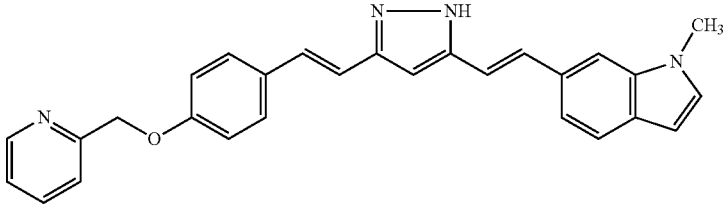 [SMILES: Cn1ccc2ccc(/C=C/c3cc(/C=C/c4ccc(OCc5ccccn5)cc4)n[nH]3)cc21]

1H NMR (δ, CDCl$_3$): 3.77 (s, 3H), 5.22 (s, 2H), 6.46 (d, 1H, J = 3.0 Hz), 6.62 (s, 1H), 6.91-6.97 (m, 3H), 7.04-7.10 (m, 3H), 7.22-7.27 (m, 2H), 7.31 (dd, 1H, J = 1.0, 8.3 Hz), 7.40-7.43 (m, 3H), 7.51-7.53 (m, 1H), 7.58 (d, 1H, J = 8.3 Hz), 7.70-7.74 (m, 1H), 8.60-8.62 (m, 1H),
MS (EI) m/z 432 (M$^+$).

TABLE 12

18-1 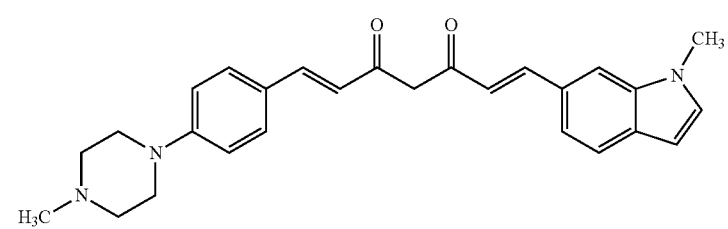 [SMILES: CN1CCN(c2ccc(/C=C/C(=O)CC(=O)/C=C/c3ccc4ccn(C)c4c3)cc2)CC1]

1H NMR (δ, CDCl$_3$): 2.35 (s, 3H), 2.56 (t, 4H, J = 4.9 Hz), 3.32 (t, 4H, J = 4.9 Hz), 3.83 (s, 3H), 5.81 (s, 1H), 6.44-6.51 (m, 2H), 6.65 (d, 1H, J = 15.7 Hz), 6.89 (d, 2H, J = 8.6 Hz), 7.12 (d, 1H, J = 2.9 Hz), 7.38 (d, 1H, J = 8.3 Hz), 7.44-7.50 (m, 3H), 7.58-7.64 (m, 2H), 7.81 (d, 1H, J = 15.7 Hz), 16.15 (brs, 1H)
MS (EI) m/z 427 (M$^+$).

TABLE 12-continued
18-2
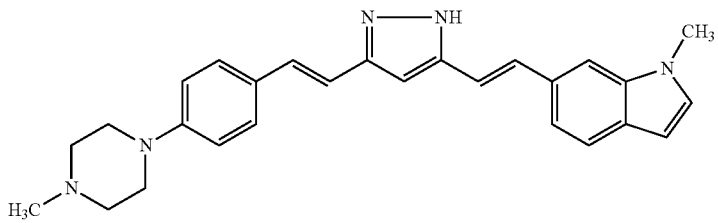 [SMILES: CN1CCN(c2ccc(/C=C/c3cc(/C=C/c4ccc5ccn(C)c5c4)[nH]n3)cc2)CC1]
1H NMR (δ, CDCl₃): 2.38 (s, 3H), 2.57-2.64 (m, 4H), 3.24-3.31 (m, 4H), 3.80 (s, 3H), 6.45-6.48 (m, 1H), 6.60-6.62 (m, 1H), 6.87-6.92 (m, 3H), 6.99-7.10 (m, 3H), 7.20-7.27 (m, 1H), 7.32 (d, 1H, J = 8.5 Hz), 7.39-7.43 (m, 3H), 7.57-7.61 (m, 1H)
MS (EI) m/z 423 (M⁺).
TABLE 13
19-1
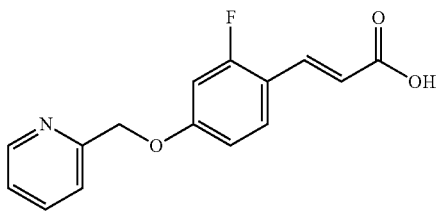 [SMILES: O=C(O)/C=C/c1ccc(OCc2ccccn2)cc1F]
1H NMR (δ, DMSO-d₆): 5.25 (s, 2H), 6.46 (d, 1H, J = 16.1 Hz), 6.92-6.96 (m, 1H), 7.02-7.07 (m, 1H), 7.35-7.39 (m, 1H), 7.52-7.54 (m, 1H), 7.59 (d, 1H, J = 16.1 Hz), 7.76-7.80 (m, 1H), 7.83-7.88 (m, 1H), 8.58-8.60 (m, 1H), 12.41 (brs, 1H)
MS (EI) m/z 273 (M⁺).
19-2
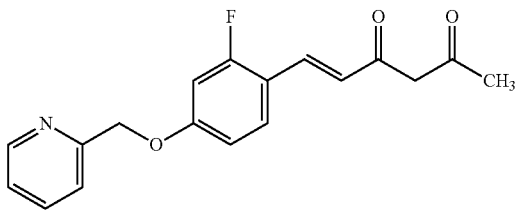 [SMILES: CC(=O)CC(=O)/C=C/c1ccc(OCc2ccccn2)cc1F]
1H NMR (δ, CDCl₃): 2.16 (s, 3H), 5.23 (s, 2H), 5.63-5.64 (m, 1H), 6.44-6.48 (m, 1H), 6.72-6.76 (m, 1H), 6.79-6.82 (m, 1H), 7.25-7.29 (m, 1H), 7.42-7.47 (m, 1H), 7.48-7.50 (m, 1H), 7.63 (d, 1H, J = 16.1 Hz), 7.72-7.77 (m, 1H), 8.60-8.63 (m, 1H)
MS (EI) m/z 313 (M⁺).
19-3
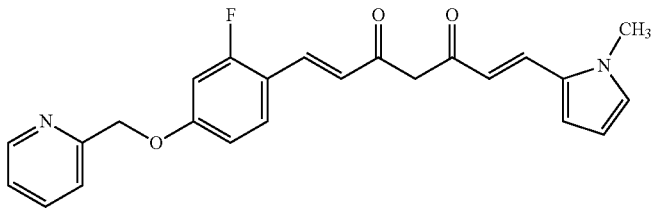 [SMILES: Cn1cccc1/C=C/C(=O)CC(=O)/C=C/c1ccc(OCc2ccccn2)cc1F]
1H NMR (δ, CDCl₃): 3.74 (s, 3H), 5.23 (s, 2H), 5.72 (s, 1H), 6.19-6.22 (m, 1H), 6.37 (d, 1H, J = 15.4 Hz), 6.59 (d, 1H, J = 16.1 Hz), 6.71-6.77 (m, 2H), 6.77-6.79 (m, 1H), 6.81 (dd, 1H, J = 2.5 Hz, 8.8 Hz), 7.24-7.28 (m, 1H), 7.45-7.51 (m, 2H), 7.61 (d, 1H, J = 15.4 Hz), 7.67 (d, 1H, J = 16.1 Hz), 7.72-7.76 (m, 1H), 8.61-8.63 (m, 1H), 16.10 (brs, 1H)
MS (EI) m/z 404 (M⁺).

TABLE 13-continued 19-4

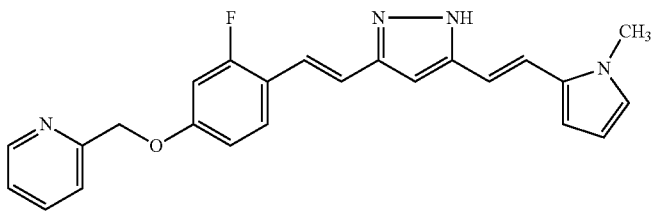 [SMILES: Cn1cccc1/C=C/c1cc(/C=C/c2ccc(OCc3ccccn3)cc2F)n[nH]1]

1H NMR (δ, CDCl₃): 3.70 (s, 3H), 5.21 (s, 2H), 6.14-6.16 (m, 1H), 6.50 (dd, 1H, J = 1.4 Hz, 3.8 Hz), 6.58 (s, 1H), 6.65 (t, 1H, J = 2.1 Hz), 6.71-6.81 (m, 3H), 6.94-7.02 (m, 2H), 7.14 (d, 1H, J = 16.7 Hz), 7.24-7.27 (m, 1H), 7.47 (t, 1H, J = 8.7 Hz), 7.50 (d, 1H, J = 8.0 Hz), 7.71-7.75 (m, 1H), 8.62 (d, 1H, J = 4.9 Hz)
MS (EI) m/z 400 (M⁺).

TABLE 14

20-1

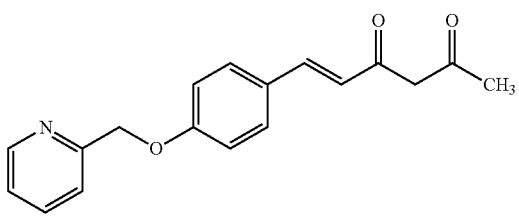 [SMILES: CC(=O)CC(=O)/C=C/c1ccc(OCc2ccccn2)cc1]

1H NMR (δ, CDCl₃): 2.15 (s, 3H), 5.24 (s, 2H), 5.61 (s, 1H), 6.34 (d, 1H, J = 16.0 Hz), 6.99 (d, 2H, J = 8.7 Hz), 7.23 (dd, 1H, J = 5.0 Hz, 7.6 Hz), 7.47 (d, 2H, J = 8.7 Hz), 7.48-7.51 (m, 1H), 7.55 (d, 1H, J = 16.0 Hz), 7.69-7.73 (m, 1H), 8.60-8.62 (m, 1H), 15.43 (brs, 1H)

20-2

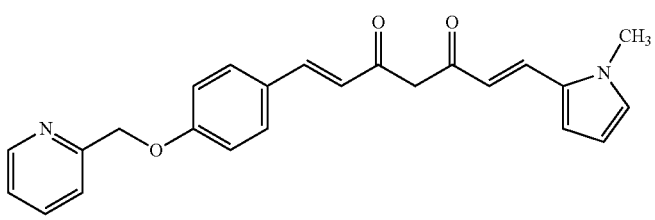 [SMILES: Cn1cccc1/C=C/C(=O)CC(=O)/C=C/c1ccc(OCc2ccccn2)cc1]

1H NMR (δ, CDCl₃): 3.74 (s, 3H), 5.25 (s, 2H), 5.71 (s, 1H), 6.19-6.21 (m, 1H), 6.37 (d, 1H, J = 15.4 Hz), 6.48 (d, 1H, J = 15.8 Hz), 6.71-6.73 (m, 1H), 6.77-6.78 (m, 1H), 7.00 (d, 2H, J = 8.8 Hz), 7.23-7.27 (m, 1H), 7.48-7.52 (m, 1H), 7.50 (d, 2H, J = 8.8 Hz), 7.59 (d, 1H, J = 15.8 Hz), 7.60 (d, 1H, J = 15.4 Hz), 7.71-7.75 (m, 1H), 8.61 (d, 1H, J = 4.2 Hz)
MS (EI) m/z 386 (M⁺).

20-3

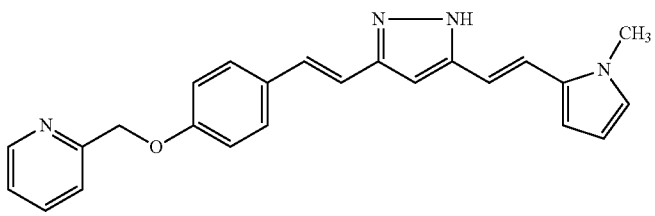 [SMILES: Cn1cccc1/C=C/c1cc(/C=C/c2ccc(OCc3ccccn3)cc2)n[nH]1]

1H NMR (δ, CDCl₃): 3.69 (s, 3H), 5.23 (s, 2H), 6.15 (t, 1H, J = 3.2 Hz), 6.49 (dd, 1H, J = 1.5 Hz, 3.7 Hz), 6.54 (s, 1H), 6.64-6.66 (m, 1H), 6.76 (d, 1H, J = 16.2 Hz), 6.90 (d, 1H, J = 16.5 Hz), 6.96 (d, 1H, J = 16.2 Hz), 6.98 (d, 2H, J = 8.8 Hz), 7.02 (d, 1H, J = 16.5 Hz), 7.22-7.26 (m, 1H), 7.42 (d, 2H, J = 8.8 Hz), 7.52 (d, 1H, J = 7.9 Hz), 7.70-7.74 (m, 1H), 8.60-8.62 (m, 1H)
MS (EI) m/z 382 (M⁺).

TABLE 15
21-1
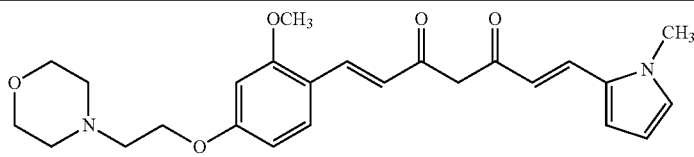
MS (EI) m/z 438 (M⁺).
21-2
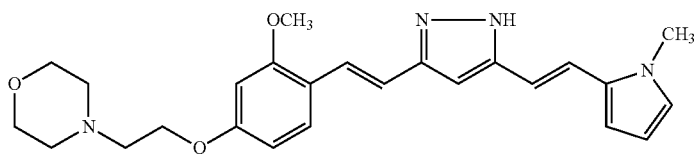 [SMILES: COc1cc(OCCN2CCOCC2)ccc1/C=C/c1cc(/C=C/c2cccn2C)[nH]n1]
1H NMR (δ, CDCl₃): 2.57-2.60 (m, 4H), 2.81 (t, 2H J = 5.7 Hz), 3.69 (s, 3H), 3.73-3.76 (m, 4H), 3.86 (s, 3H), 4.13 (t, 2H, J = 5.7 Hz), 6.13-6.15 (m, 1H), 6.47-6.51 (m, 3H), 6.54 (s, 1H), 6.63-6.64 (m, 1H), 6.77 (d, 1H, J = 16.0 Hz), 6.95 (d, 1H, J = 16.5 Hz), 6.96 (d, 1H, J = 16.0 Hz), 7.29 (d, 1H, J = 16.5 Hz), 7.43 (d, 1H, J = 8.3 Hz)
MS (EI) m/z 434 (M⁺).
22-1
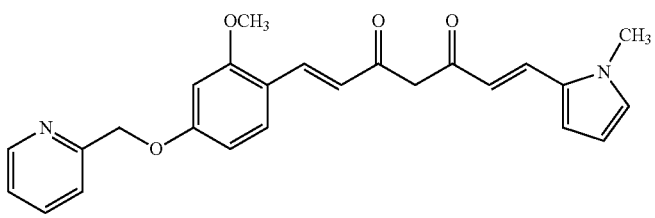 [SMILES: COc1cc(OCc2ccccn2)ccc1/C=C/C(=O)CC(=O)/C=C/c1cccn1C]
MS (EI) m/z 416 (M⁺).
22-2
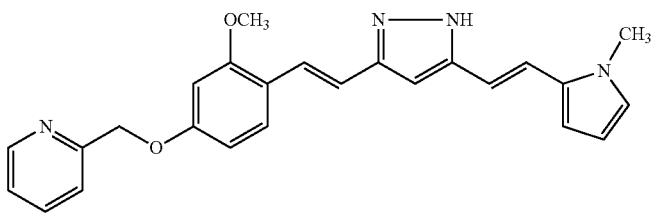 [SMILES: COc1cc(OCc2ccccn2)ccc1/C=C/c1cc(/C=C/c2cccn2C)[nH]n1]
1H NMR (δ, CDCl₃): 3.68 (s, 3H), 3.84 (s, 3H), 5.23 (s, 2H), 6.13-6.15 (m, 1H), 6.47 (dd, 1H, J = 1.4, 3.4 Hz), 6.54 (s, 1H), 6.55-6.59 (m, 2H), 6.62-6.63 (m, 1H), 6.77 (d, 1H, J = 16.0 Hz), 6.95 (d, 1H, J = 16.5 Hz), 6.96 (d, 1H, J = 16.0 Hz), 7.22-7.25 (m, 1H), 7.29 (d, 1H, J = 16.5 Hz), 7.42 (d, 1H, J = 8.7 Hz), 7.51-7.53 (m, 1H), 7.70-7.74 (m, 1H), 8.60-8.62 (m, 1H)
MS (EI) m/z 412 (M⁺).
TABLE 16
23-1
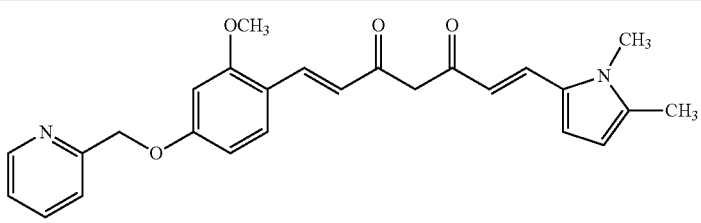 [SMILES: COc1cc(OCc2ccccn2)ccc1/C=C/C(=O)CC(=O)/C=C/c1ccc(C)n1C]
1H NMR (δ, CDCl₃): 2.28 (s, 3H), 3.59 (s, 3H), 3.86 (s, 3H), 5.25 (s, 2H), 5.69 (s, 1H), 5.99 (d, 1H, J = 3.9 Hz), 6.32 (d, 1H, J = 15.5 Hz), 6.56-6.61 (m, 3H), 6.66 (d, 1H, J = 3.9 Hz), 7.24-7.28 (m, 1H), 7.46 (d, 1H, J = 9.3 Hz), 7.50-7.53 (m, 1H), 7.60 (d, 1H, J = 15.5 Hz), 7.71-7.76 (m, 1H), 7.85 (d, 1H, J = 16.2 Hz), 8.60-8.63 (m, 1H)
MS (EI) m/z 430 (M⁺).

TABLE 16-continued
23-2
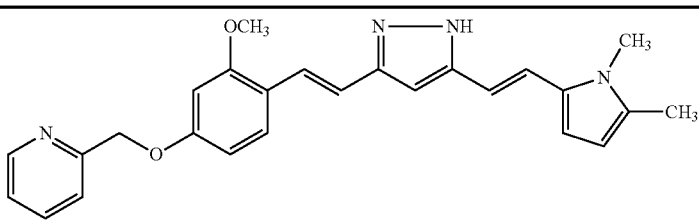
1H NMR (δ, CDCl₃): 2.25 (s, 3H), 3.56 (s, 3H), 3.85 (s, 3H), 5.23 (s, 2H), 5.90-5.95 (m, 1H), 6.40-6.45 (m, 1H), 6.52-6.61 (m, 3H), 6.71 (d, 1H, J = 16.5 Hz), 6.97 (d, 1H, J = 17.0 Hz), 7.03 (d, 1H, J = 16.5 Hz), 7.21-7.35 (m, 2H), 7.42 (d, 1H, J = 8.5 Hz), 7.50-7.54 (m, 1H), 7.69-7.76 (m, 1H), 8.68-8.64 (m, 1H)
MS (EI) m/z 426 (M⁺).
24-1
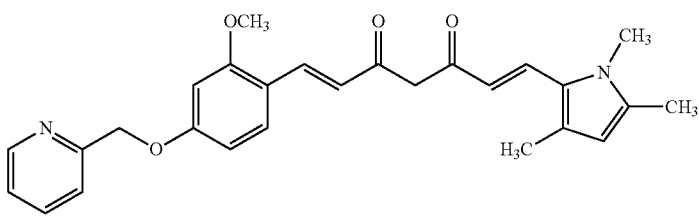 [SMILES: COc1cc(OCc2ccccn2)ccc1/C=C/C(=O)CC(=O)/C=C/c1c(C)cc(C)n1C]
1H NMR (δ, CDCl₃): 2.24 (s, 3H), 2.27 (s, 3H), 3.58 (s, 3H), 3.86 (s, 3H), 5.24 (s, 2H), 5.70 (s, 1H), 5.86 (s, 1H), 6.18 (d, 1H, J = 15.5 Hz), 6.56-6.60 (m, 3H), 7.23-7.27 (m, 1H), 7.46 (d, 1H, J = 9.2 Hz), 7.49-7.53 (m, 1H), 7.69-7.75 (m, 2H), 7.84 (d, 1H, J = 16.1 Hz), 8.60-8.63 (m, 1H)
MS (EI) m/z 444 (M⁺).
24-2
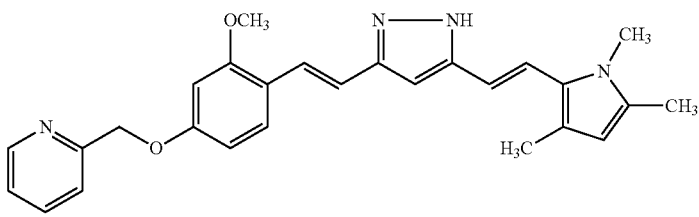 [SMILES: COc1cc(OCc2ccccn2)ccc1/C=C/c1cc(/C=C/c2c(C)cc(C)n2C)[nH]n1]
1H NMR (δ, CDCl₃): 2.22 (s, 3H), 2.23 (s, 3H), 3.54 (s, 3H), 3.86 (s, 3H), 5.24 (s, 2H), 5.80 (s, 1H), 6.52-6.60 (m, 4H), 6.97 (d, 1H, J = 16.7 Hz), 7.01 (d, 1H, J = 16.7 Hz), 7.23-7.27 (m, 1H), 7.30 (d, 1H, J = 16.7 Hz), 7.44 (d, 1H, J = 8.3 Hz), 7.51-7.54 (m, 1H), 7.71-7.75 (m, 1H), 8.61-8.63 (m, 1H)
MS (EI) m/z 440 (M⁺).
TABLE 17
25-1
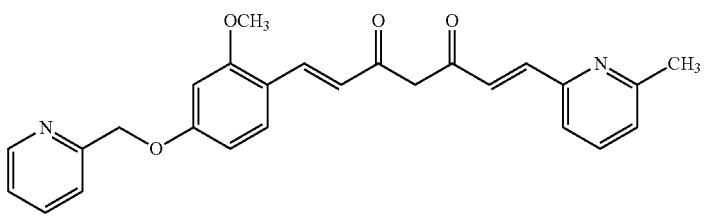 [SMILES: COc1cc(OCc2ccccn2)ccc1/C=C/C(=O)CC(=O)/C=C/c1cccc(C)n1]
1H NMR (δ, CDCl₃): 2.60 (s, 3H), 3.88 (s, 3H), 5.25 (s, 2H), 5.92 (s, 1H), 6.58-6.61 (m, 2H), 6.66 (d, 1H, J = 16.0 Hz), 7.09-7.12 (m, 1H), 7.17 (d, 1H, J = 15.5 Hz), 7.20-7.23 (m, 1H), 7.24-7.27 (m, 1H), 7.48-7.53 (m, 2H), 7.56-7.61 (m, 2H), 7.71-7.76 (m, 1H), 7.93 (d, 1H, J = 16.0 Hz), 8.61-8.63 (m, 1H), 15.85 (brs, 1H)
MS (EI) m/z 428 (M⁺).

TABLE 17-continued 25-2

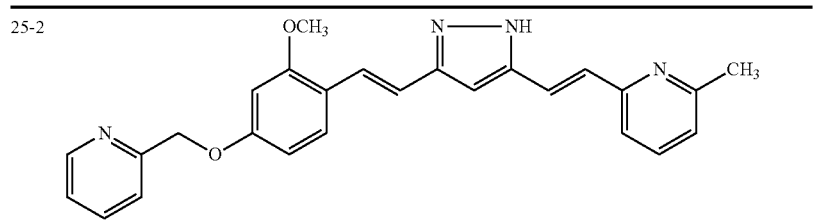

1H NMR (δ, CDCl₃): 2.59 (s, 3H), 3.86 (s, 3H), 5.24 (s, 2H), 6.56-6.60 (m, 2H), 6.68 (s, 1H), 6.97 (d, 1H, J = 16.6 Hz), 7.02-7.04 (m, 1H), 7.16 (d, 1H, J = 16.2 Hz), 7.23-7.27 (m, 2H), 7.30 (d, 1H, J = 16.6 Hz), 7.44 (d, 1H, J = 8.3 Hz), 7.51-7.58 (m, 3H), 7.71-7.75 (m, 1H), 8.61-8.63 (m, 1H)
MS (EI) m/z 424 (M⁺).

26-1

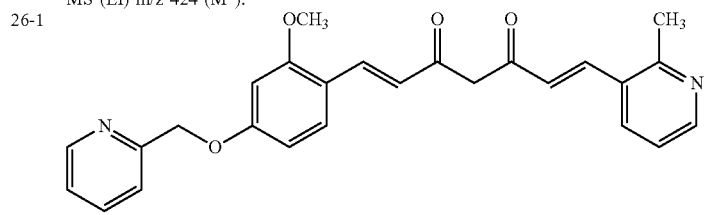

MS (EI) m/z 428 (M⁺).

26-2

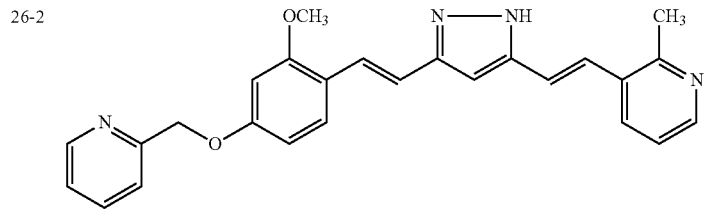

1H NMR (δ, CDCl₃): 2.67 (s, 3H), 3.86 (s, 3H), 5.24 (s, 2H), 6.56-6.61 (m, 2H), 6.65 (s, 1H), 6.95 (d, 1H, J = 16.4 Hz), 7.00 (d, 1H, J = 16.4 Hz), 7.15 (dd, 1H, J = 4.7, 7.9 Hz), 7.23-7.28 (m, 2H), 7.31 (d, 1H, J = 16.4 Hz), 7.43 (d, 1H, J = 8.6 Hz), 7.53 (d, 1H, J = 7.9 Hz), 7.74 (dt, 1H, J = 1.9, 7.6 Hz), 7.83 (dd, 1H, J = 1.6, 7.9 Hz), 8.40 (dd, 1H, J = 1.6, 4.7 Hz), 8.61-8.63 (m, 1H)
MS (EI) m/z 424 (M⁺).

TABLE 18

27-1

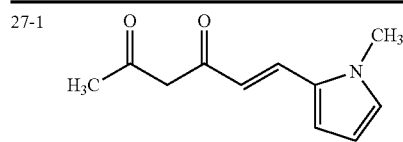

1H NMR (δ, CDCl3): 2.12 (s, 3H), 3.71 (s, 3H), 5.55 (s, 1H), 6.17-6.19 (m, 1H), 6.20 (d, 1H, J = 15.3 Hz), 6.65-6.66 (m, 1H), 6.74-6.75 (m, 1H), 7.52 (d, 1H, J = 15.3 Hz), 15.63 (brs, 1H)

27-2

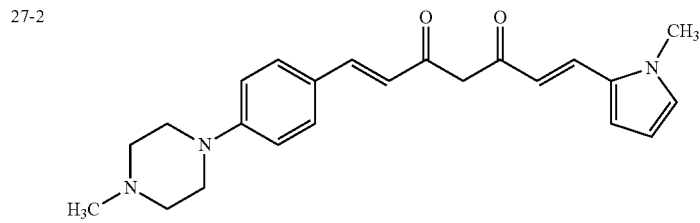

1H NMR (δ, CDCl₃): 2.85 (s, 3H), 3.06 (t, 4H, J = 5.0 Hz), 3.82 (t, 4H, J = 5.0 Hz), 4.22 (s, 3H), 6.19 (s, 1H), 6.68-6.70 (m, 1H), 6.85 (d, 1H, J = 15.4 Hz), 6.94 (d, 1H, J = 16.0 Hz), 7.19 (dd, 1H, J = 1.3 Hz, 3.9 Hz), 7.24-7.26 (m, 1H), 7.38 (d, 2H, J = 8.9 Hz), 7.95 (d, 2H, J = 8.9 Hz), 8.07 (d, 1H, J = 16.0 Hz), 8.08 (d, 1H, J = 15.4 Hz), 16.68 (brs, 1H)
MS (EI) m/z 377 (M⁺).

TABLE 18-continued 27-3

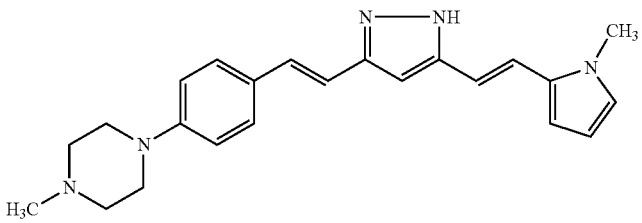 [SMILES: CN1CCN(c2ccc(/C=C/c3cc(/C=C/c4cccn4C)[nH]n3)cc2)CC1]

1H NMR (δ, CDCl₃): 2.38 (s, 3H), 2.58-2.64 (m, 4H), 3.28 (t, 4H, J = 4.8 Hz), 3.69 (s, 3H), 6.15 (dd, 1H, J = 2.8 Hz, 3.6 Hz), 6.48 (dd, 1H, J = 1.5 Hz, 3.6 Hz), 6.52 (s, 1H), 6.63-6.65 (m, 1H), 6.76 (d, 1H, J = 16.2 Hz), 6.86 (d, 1H, J = 16.4 Hz), 6.90 (d, 2H, J = 8.8 Hz), 6.95 (d, 1H, J = 16.2 Hz), 6.99 (d, 1H, J = 16.4 Hz), 7.39 (d, 2H, J = 8.8 Hz)
MS (EI) m/z 373 (M⁺).

TABLE 19

28-1

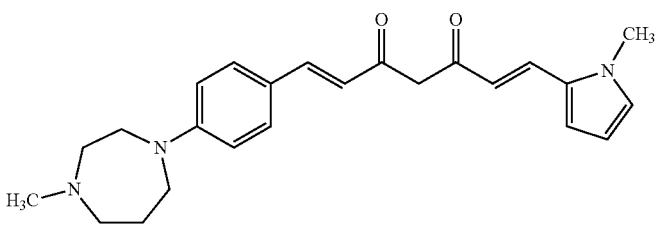 [SMILES: CN1CCCN(c2ccc(/C=C/C(=O)CC(=O)/C=C/c3cccn3C)cc2)CC1]

1H NMR (δ, CDCl₃): 2.02 (quint, 2H, J = 5.9 Hz), 2.38 (s, 3H), 2.54-2.58 (m, 2H), 2.69-2.73 (m, 2H), 3.52-3.56 (m, 2H), 3.60-3.64 (m, 2H), 3.73 (s, 3H), 5.68 (s, 1H), 6.18-6.21 (m, 1H), 6.36 (d, 1H, J = 15.5 Hz), 6.40 (d, 1H, J = 15.7 Hz), 6.66-6.70 (m, 3H), 6.75-6.77 (m, 1H), 7.42-7.45 (m, 2H), 7.57 (d, 1H, J = 15.5 Hz), 7.59 (d, 1H, J = 15.6 Hz)
MS (EI) m/z 391 (M⁺).

28-2

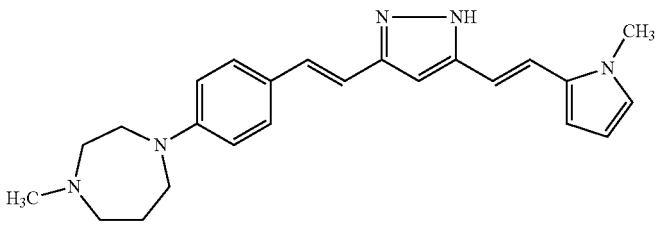 [SMILES: CN1CCCN(c2ccc(/C=C/c3cc(/C=C/c4cccn4C)[nH]n3)cc2)CC1]

1H NMR (δ, CDCl₃): 2.00-2.06 (m, 2H), 2.39 (s, 3H), 2.55-2.60 (m, 2H), 2.70-2.74 (m, 2H), 3.50-3.54 (m, 2H), 3.59-3.62 (m, 2H), 3.69 (s, 3H), 6.14-6.16 (m, 1H), 6.47-6.53 (m, 2H), 6.63-6.69 (m, 3H), 6.78 (d, 1H, J = 16.1 Hz), 6.79 (d, 1H, J = 16.4 Hz), 6.96 (d, 1H, J = 16.1 Hz), 6.98 (d, 1H, J = 16.4 Hz), 7.34-7.38 (m, 2H)
MS (EI) m/z 387 (M⁺).

29-1

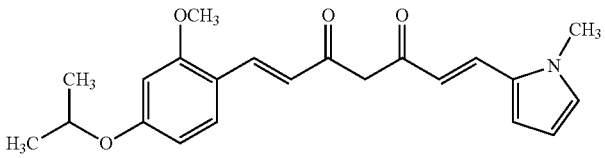 [SMILES: COc1cc(OC(C)C)ccc1/C=C/C(=O)CC(=O)/C=C/c1cccn1C]

1H NMR (δ, CDCl₃): 1.36 (d, 6H, J = 5.8 Hz), 3.73 (s, 3H), 3.86 (s, 3H), 4.57-4.63 (m, 1H), 5.71 (s, 1H), 6.18-6.20 (m, 1H), 6.36 (d, 1H, J = 15.4 Hz), 6.44 (d, 1H, J = 2.4 Hz), 6.49 (dd, 1H, J = 2.4 Hz, 8.5 Hz), 6.59 (d, 1H, J = 15.9 Hz), 6.68-6.70 (m, 1H), 6.74-6.76 (m, 1H), 7.45 (d, 1H, J = 8.5 Hz), 7.58 (d, 1H, J = 15.4 Hz), 7.87 (d, 1H, J = 15.9 Hz)
MS (EI) m/z 367 (M⁺).

TABLE 19-continued
29-2
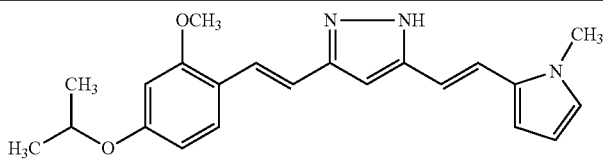
1H NMR (δ, CDCl$_3$): 1.35 (d, 6H, J = 6.1 Hz), 3.69 (s, 3H), 3.85 (s, 3H), 4.53-4.61 (m, 1H), 6.13-6.15 (m, 1H), 6.45 (d, 1H, J = 2.3 Hz), 6.46-6.49 (m, 2H), 6.54 (s, 1H), 6.62-6.64 (m, 1H), 6.77 (d, 1H, J = 16.2 Hz), 6.95 (d, 1H, J = 16.7 Hz), 7.01 (d, 1H, J = 16.2 Hz), 7.30 (d, 1H, J = 16.7 Hz), 7.41 (d, 1H, J = 8.5 Hz)
MS (EI) m/z 363 (M$^+$).
TABLE 20
30-1
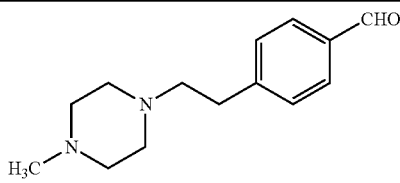
1H NMR (δ, CDCl$_3$): 2.30 (s, 3H), 2.40-2.66 (m, 10H), 2.86-2.90 (m, 2H), 7.37 (d, 2H, J = 8.0 Hz), 7.80 (d, 2H, J = 8.0 Hz), 9.98 (s, 1H)
30-2
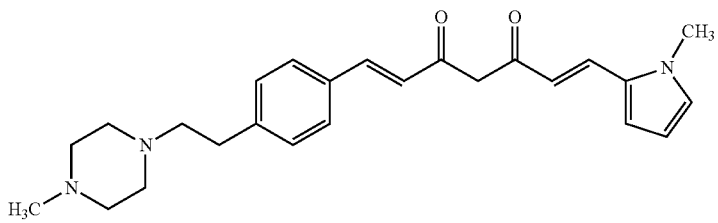 [SMILES: CN1CCN(CCc2ccc(/C=C/C(=O)CC(=O)/C=C/c3cccn3C)cc2)CC1]
MS (EI) m/z 405 (M$^+$).
30-3
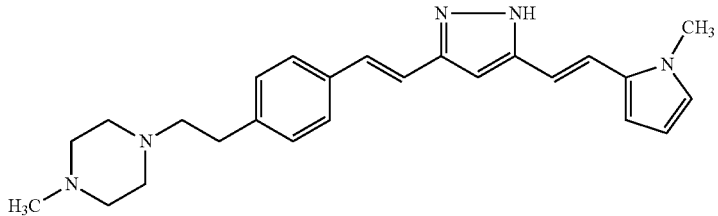 [SMILES: CN1CCN(CCc2ccc(/C=C/c3cc(/C=C/c4cccn4C)[nH]n3)cc2)CC1]
1H NMR (δ, CDCl$_3$): 2.30 (s, 3H), 2.43-2.66 (m, 10H), 2.79-2.83 (m, 2H), 3.70 (s, 3H), 6.14-6.16 (m, 1H), 6.49 (dd, 1H, J = 1.4 Hz, 3.7 Hz), 6.55 (s, 1H), 6.64-6.65 (m, 1H), 6.75 (d, 1H, J = 16.3 Hz), 6.95 (d, 1H, J = 16.5 Hz), 6.98 (d, 1H, J = 16.3 Hz), 7.05 (d, 1H, J = 16.5 Hz), 7.20 (d, 2H, J = 8.1 Hz), 7.40 (d, 2H, J = 8.1 Hz)
MS (EI) m/z 401 (M$^+$).
TABLE 21
31-1
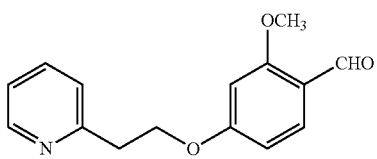 [SMILES: COc1cc(OCCc2ccccn2)ccc1C=O]
MS (EI) m/z 257 (M$^+$).

TABLE 21-continued 31-2

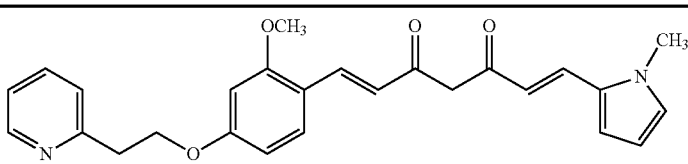

1H NMR (δ, CDCl₃): 3.28 (t, 2H, J = 6.6 Hz), 3.73 (s, 3H), 3.86 (s, 3H 4.42 (t, 2H, J = 6.6 Hz), 5.71 (s, 1H), 6.17-6.21 (m, 1H), 6.36 (d, 1H, J = 15.4 Hz), 6.45 (d, 1H, J = 2.0 Hz), 6.53 (dd, 1H, J = 2.0 Hz, 8.6 Hz), 6.59 (d, 1H, J = 16.0 Hz), 6.90 (d, 1H, J = 3.68 Hz), 6.75 (s, 1H), 7.13-7.18 (m, 1H), 7.24-7.28 (m, 1H), 7.45 (d, 1H, J = 8.6 Hz), 7.58 (d, 1H, J = 15.4 Hz), 7.60-7.66 (m, 1H), 7.87 (d, 1H, J = 16.0 Hz), 8.57 (d, 1H, J = 4.7 Hz), 16.18 (brs, 1H)
MS (EI) m/z 430 (M⁺).

31-3

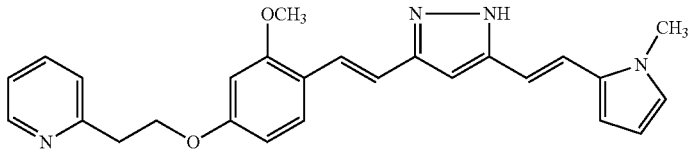 [SMILES: COc1cc(OCCc2ccccn2)ccc1/C=C/c1cc(/C=C/c2cccn2C)[nH]n1]

1H NMR (δ, CDCl₃): 3.28 (t, 2H, J = 6.7 Hz), 3.70 (s, 3H), 3.84 (s, 3H), 4.40 (t, 2H, J = 6.7 Hz), 6.15 (t, 1H, J = 3.3 Hz), 6.45 (d, 1H, J = 2.2 Hz), 6.48-6.52 (m, 2H), 6.55 (s, 1H), 6.63-6.65 (m, 1H), 6.77 (d, 1H, J = 16.5 Hz), 6.94 (d, 1H, J = 16.9 Hz), 6.99 (d, 1H, J = 16.5 Hz), 7.17 (dd, 1H, J = 5.1 Hz, 7.45 Hz), 7.25-7.32 (m, 2H), 7.41 (d, 1H, J = 8.6 Hz), 7.62-7.66 (m, 1H), 8.56-8.58 (m, 1H)
MS (EI) m/z 426 (M⁺).

TABLE 22

32-1

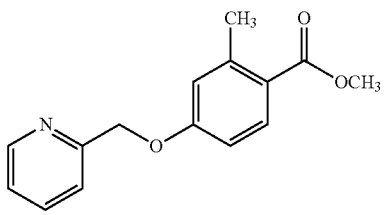 [SMILES: COC(=O)c1ccc(OCc2ccccn2)cc1C]

1H NMR (δ, CDCl₃): 2.59 (s, 3H), 3.85 (s, 3H), 5.24 (s, 2H), 6.82 (dd, 1H, J = 2.5 Hz, 8.8 Hz), 6.85 (d, 1H, J = 2.5 Hz), 7.22-7.26 (m, 1H), 7.48-7.51 (m, 1H), 7.70-7.74 (m, 1H), 7.93 (d, 1H, J = 8.7 Hz), 8.60-8.62 (m, 1H)
MS (EI) m/z 257 (M⁺).

32-2

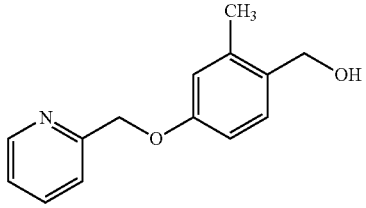 [SMILES: Cc1cc(OCc2ccccn2)ccc1CO]

1H NMR (δ, CDCl₃): 2.36 (s, 3H), 4.64 (s, 2H), 5.19 (s, 2H), 6.78 (dd, 1H, J = 2.7 Hz, 8.4 Hz), 6.85 (d, 1H, J = 2.6 Hz), 7.21-7.25 (m, 2H), 7.50-7.53 (m, 1H), 7.69-7.73 (m, 1H), 8.58-8.61 (m, 1H)
MS (EI) m/z 229 (M⁺).

TABLE 22-continued 32-3

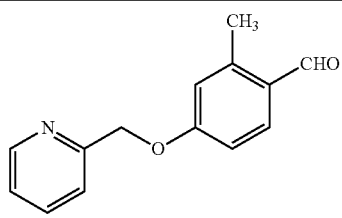

1H NMR (δ, CDCl$_3$): 2.65 (s, 3H), 5.27 (s, 2H), 6.86 (d, 1H, J = 2.4 Hz), 6.93 (dd, 1H, J = 2.6 Hz, 8.5 Hz), 7.24-7.27 (m, 1H), 7.48-7.50 (m, 1H), 7.71-7.77 (m, 2H), 8.61-8.63 (m, 1H), 10.12 (s, 1H)
MS (EI) m/z 227 (M$^+$).

32-4

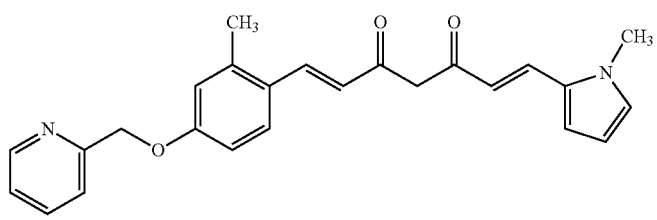 [SMILES: Cc1cc(OCc2ccccn2)ccc1/C=C/C(=O)CC(=O)/C=C/c1cccn1C]

1H NMR (δ, CDCl$_3$): 2.44 (s, 3H), 3.74 (s, 3H), 5.23 (s, 2H), 5.70 (s, 1H), 6.19-6.21 (m, 1H), 6.37 (d, 1H, J = 15.5 Hz), 6.43 (d, 1H, J = 15.5 Hz), 6.71-6.73 (m, 1H), 6.77-6.78 (m, 1H), 6.83-6.86 (m, 2H), 7.22-7.27 (m, 1H), 7.49-7.52 (m, 1H), 7.55-7.58 (m, 1H), 7.60 (d, 1H, J = 15.5 Hz), 7.70-7.74 (m, 1H), 7.86 (d, 1H, J = 15.6 Hz), 8.60-8.62 (m, 1H)
MS (EI) m/z 400 (M$^+$).

30

TABLE 23

32-5

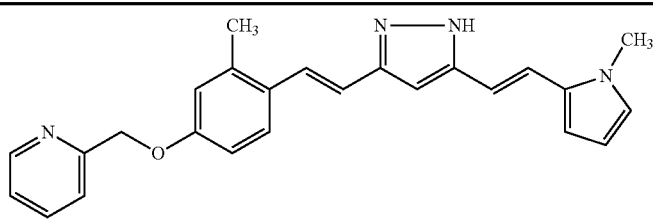

1H NMR (δ, CDCl$_3$): 2.40 (s, 3H), 3.70 (s, 3H), 5.22 (s, 2H), 6.15-6.16 (m, 1H), 6.49 (dd, 1H, J = 1.6 Hz, 3.8 Hz), 6.55 (s, 1H), 6.64-6.66 (m, 1H), 6.77 (d, 1H, J = 16.3 Hz), 6.80-6.85 (m, 3H), 6.96 (d, 1H, J = 16.3 Hz), 7.21-7.25 (m, 2H), 7.49-7.53 (m, 2H), 7.70-7.74 (m, 1H), 8.60-8.62 (m, 1H)
MS (EI) m/z 396 (M$^+$).

TABLE 24

33-1

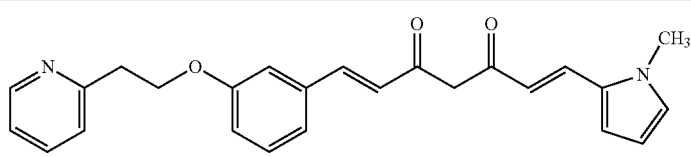 [SMILES: Cn1cccc1/C=C/C(=O)CC(=O)/C=C/c1cccc(OCCc2ccccn2)c1]

1H NMR (δ, CDCl$_3$): 3.30 (t, 2H, J = 6.6 Hz), 3.74 (s, 3H), 4.42 (t, 2H, J = 6.6 Hz), 5.73 (s, 1H), 6.20-6.22 (m, 1H), 6.38 (d, 1H, J = 15.3 Hz), 6.56 (d, 1H, J = 15.9 Hz), 6.72-6.74 (m, 1H), 6.78-6.79 (m, 1H), 6.90-6.93 (m, 1H), 7.06-7.08 (m, 1H), 7.11-7.13 (m, 1H), 7.16-7.20 (m, 1H), 7.25-7.31 (m, 2H), 7.56 (d, 1H, J = 15.8 Hz), 7.62 (d, 1H, J = 15.6 Hz), 7.63-7.67 (m, 1H), 8.56-8.59 (m, 1H), 16.07 (brs, 1H),
MS (EI) m/z 400 (M$^+$).

TABLE 24-continued 33-2

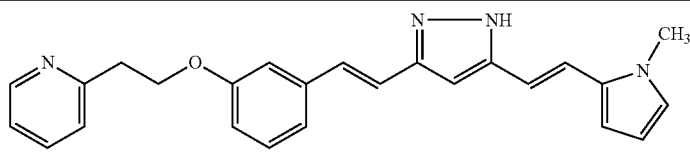

1H NMR (δ, CDCl$_3$): 3.31 (t, 2H, J = 6.6 Hz), 3.70 (s, 3H), 4.40 (t, 2H, J = 6.6 Hz), 6.14-6.17 (m, 1H), 6.49-6.52 (m, 1H), 6.57 (s, 1H), 6.64-6.67 (m, 1H), 6.73-6.78 (m, 1H), 6.81-6.85 (m, 1H), 6.98 (d, 1H, J = 16.2 Hz), 7.01-7.08 (m, 4H), 7.17-7.21 (m, 1H), 7.22-7.28 (m, 1H), 7.30-7.34 (m, 1H), 7.64-7.69 (m, 1H), 8.56-8.59 (m, 1H)
MS (EI) m/z 396 (M$^+$).

TABLE 25

34-1

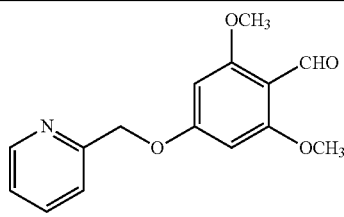

1H NMR (δ, CDCl$_3$): 3.85 (s, 6H), 50028 (s, 2H), 6.20 (s, 2H), 7.25-7.28 (m, 1H), 7.51 (d, 1H, J = 7.8 Hz), 7.73-7.77 (m, 1H), 8.60-8.62 (m, 1H), 10.35 (s, 1H)
MS (EI) m/z 273 (M$^+$).

34-2

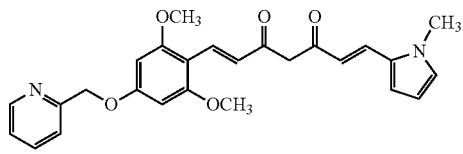 [SMILES: COc1cc(OCc2ccccn2)cc(OC)c1/C=C/C(=O)CC(=O)/C=C/c1cccn1C]

1H NMR (δ, CDCl$_3$): 3.72 (s, 3H), 3.85 (s, 6H), 5.25 (s, 2H), 5.71 (s, 1H), 6.17-6.19 (m, 1H), 6.23 (s, 2H), 6.36 (d, 1H, J = 15.4 Hz), 6.66-6.68 (m, 1H), 6.73-6.75 (m, 1H), 6.97 (d, 1H, J = 16.0 Hz), 7.23-7.26 (m, 1H), 7.51 (d, 1H, J = 7.7 Hz), 7.56 (d, 1H, J = 15.4 Hz), 7.71-7.75 (m, 1H), 8.03 (d, 1H, J = 16.0 Hz), 8.61 (d, 1H, J = 4.5 Hz), 16.26 (brs, 1H)
MS (EI) m/z 446 (M$^+$).

34-3

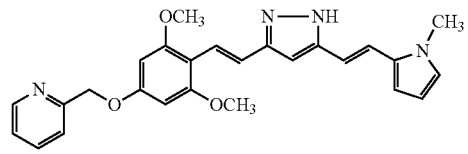 [SMILES: COc1cc(OCc2ccccn2)cc(OC)c1/C=C/c1cc(/C=C/c2cccn2C)[nH]n1]

1H NMR (δ, CDCl$_3$): 3.69 (s, 3H), 3.84 (s, 6H), 5.24 (s, 2H), 6.13-6.15 (m, 1H), 6.26 (s, 2H), 6.47 (dd, 1H, J = 1.6 Hz, 3.7 Hz), 6.54 (s, 1H), 6.61-6.63 (m, 1H), 6.80 (d, 1H, J = 16.2 Hz), 6.97 (d, 1H, J = 16.2 Hz), 7.22-7.26 (m, 1H), 7.34 (s, 2H), 7.53 (d, 1H, J = 7.9 Hz), 7.71-7.75 (m, 1H), 8.61 (d, 1H, J = 5.0 Hz)
MS (EI) m/z 442 (M$^+$).

TABLE 26

35-1

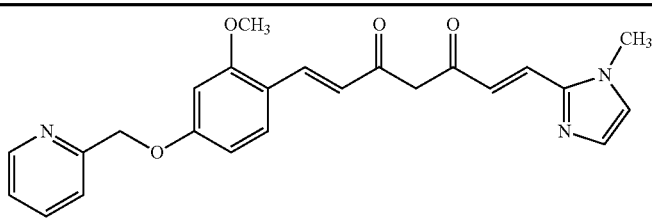

1H NMR (δ, CDCl$_3$): 3.76 (s, 3H), 3.87 (s, 3H), 5.25 (s, 2H), 5.81 (s, 1H), 6.58-6.61 (m, 2H), 6.64 (d, 1H, J = 16.0 Hz), 6.95-6.96 (m, 1H), 7.04 (d, 1H, J = 15.1 Hz), 7.16-7.17 (m, 1H), 7.22-7.26 (m, 1H), 7.44 (d, 1H, J = 15.1 Hz), 7.47-7.52 (m, 2H), 7.70-7.74 (m, 1H), 7.93 (d, 1H, J = 16.0 Hz), 8.60-8.62 (m, 1H), 15.93 (brs, 1H)
MS (EI) m/z 417 (M$^+$).

35-2

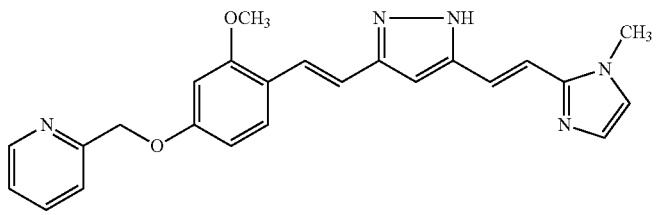

1H NMR (δ, CDCl$_3$): 3.71 (s, 3H), 3.85 (s, 3H), 5.23 (s, 2H), 6.56-6.60 (m, 3H), 6.86-6.88 (m, 1H), 6.96 (d, 1H, J = 16.8 Hz), 6.97 (d, 1H, J = 16.1 Hz), 7.09-7.11 (m, 1H), 7.22-7.25 (m, 1H), 7.29 (d, 1H, J = 16.8 Hz), 7.42 (d, 1H, J = 8.3 Hz), 7.46 (d, 1H, J = 16.1 Hz), 7.51-7.53 (m, 1H), 7.70-7.74 (m, 1H), 8.59-8.62 (m, 1H)
MS (EI) m/z 413 (M$^+$).

TABLE 26-continued
36-1
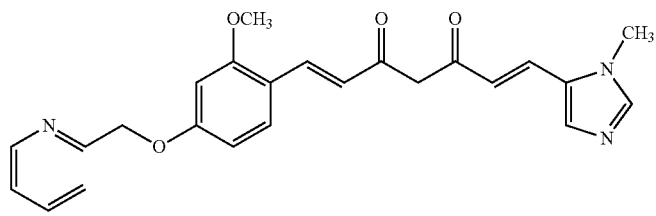 [SMILES: C=C/C=C\N=C\COc1ccc(/C=C/C(=O)CC(=O)/C=C/c2cncn2C)c(OC)c1]
MS (EI) m/z 417 (M+).
36-2
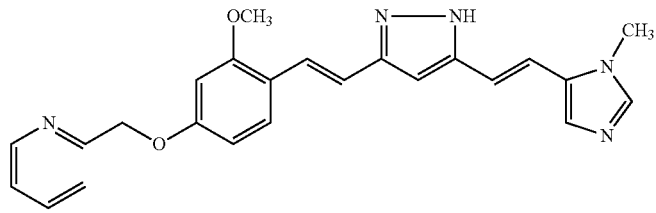 [SMILES: C=C/C=C\N=C\COc1ccc(/C=C/c2cc(/C=C/c3cncn3C)[nH]n2)c(OC)c1]
1H NMR (δ, CDCl$_3$): 3.70 (s, 3H), 3.86 (s, 3H), 5.24 (s, 2H), 6.56-6.60 (m, 3H), 6.89-6.90 (m, 2H), 6.93 (d, 1H, J = 16.5 Hz), 7.23-7.31 (m, 3H), 7.42 (d, 1H, J = 8.2 Hz), 7.43-7.44 (m, 1H), 7.51-7.54 (m, 1H), 7.71-7.75 (m, 1H), 8.61-8.63 (m, 1H)
MS (EI) m/z 413 (M+).
TABLE 27
37-1
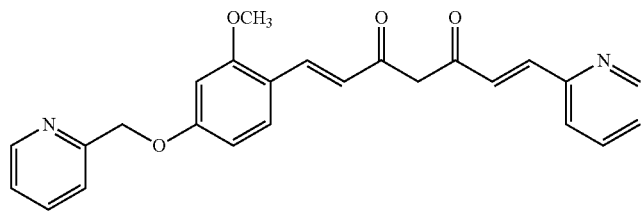 [SMILES: C=C/C=C(/C=C/C(=O)CC(=O)/C=C/c1ccc(OCc2ccccn2)cc1OC)N=C]
MS (EI) m/z 414 (M+).
37-2
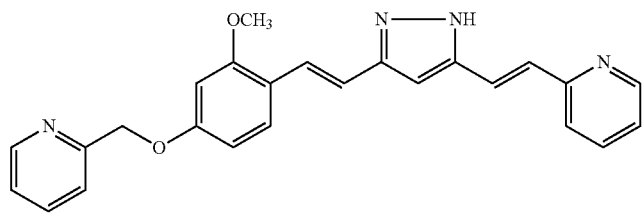 [SMILES: COc1cc(OCc2ccccn2)ccc1/C=C/c1cc(/C=C/c2ccccn2)[nH]n1]
1H NMR (δ, CDCl$_3$): 3.85 (s, 3H), 5.24 (s, 2H), 6.56-6.59 (m, 2H), 6.66 (s, 1H), 6.97 (d, 1H, J = 16.5 Hz), 7.13-7.18 (m, 2H), 7.22-7.25 (m, 1H), 7.30 (d, 1H, J = 16.5 Hz), 7.37-7.40 (m, 1H), 7.43 (d, 1H, J = 8.3 Hz), 7.51-7.53 (m, 1H), 7.56 (d, 1H, J = 16.1 Hz), 7.63-7.67 (m, 1H), 7.70-7.74 (m, 1H), 8.59-8.62 (m, 2H)
MS (EI) m/z 410 (M+).
38-1
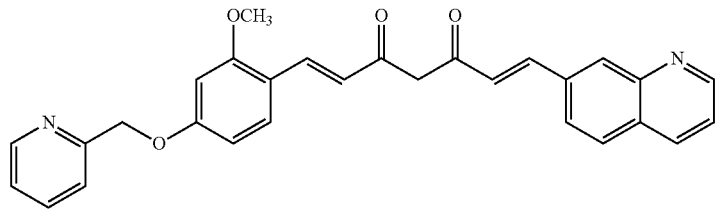 [SMILES: COc1cc(OCc2ccccn2)ccc1/C=C/C(=O)CC(=O)/C=C/c1ccc2cccnc2c1]
MS (EI) m/z 464 (M+).

TABLE 27-continued 38-2 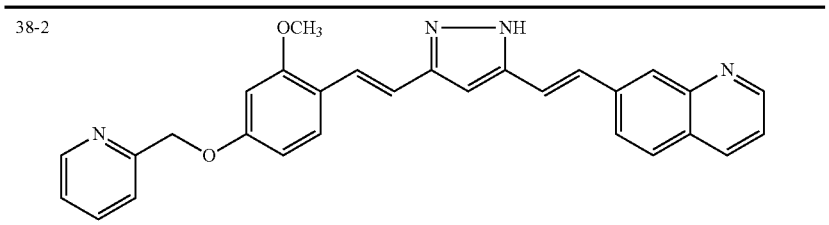

1H NMR (δ, Acetone-d₆): 3.92 (s, 3H), 5.24 (s, 2H), 6.67 (dd, 1H, J = 2.6, 8.4 Hz), 6.76 (d, 1H, J = 2.6 Hz), 6.80 (s, 1H), 7.09 (d, 1H, J = 16.7 Hz), 7.30-7.33 (m, 1H), 7.37-7.49 (m, 4H), 7.54 (d, 1H, J = 9.0 Hz), 7.66-7.68 (d, 1H, J = 8.4 Hz), 7.80-7.84 (m, 1H), 7.90-7.95 (m, 2H), 8.09-8.11 (m, 1H), 8.26-8.29 (m, 1H), 8.58-8.60 (m, 1H), 8.89 (dd, 1H, J = 1.9, 3.9 Hz)
MS (EI) m/z 460 (M⁺).

TABLE 28

39-1 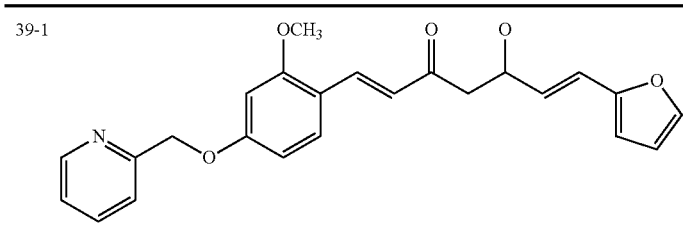

1H NMR (δ, CDCl₃): 3.87 (s, 3H), 5.25 (s, 2H), 5.78 (s, 1H), 6.46-6.48 (m, 1H), 6.51 (d, 1H, J = 15.4 Hz), 6.57-6.61 (m, 3H), 6.62 (d, 1H, J = 15.4 Hz), 7.22-7.26 (m, 1H), 7.39 (d, 1H, J = 15.4 Hz), 7.45-7.49 (m, 2H), 7.50 (d, 1H, J = 7.7 Hz), 7.70-7.74 (m, 1H), 7.90 (d, 1H, J = 15.4 Hz), 8.61 (d, 1H, J = 4.5 Hz)
MS (EI) m/z 403 (M⁺).

39-2 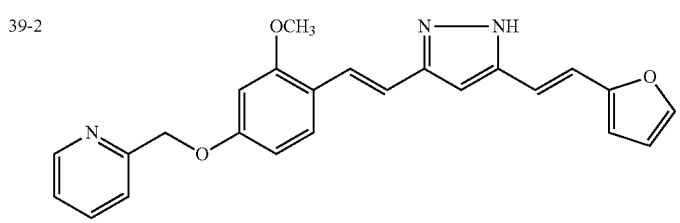

1H NMR (δ, CDCl₃): 3.85 (s, 3H), 5.24 (s, 2H), 6.37-6.39 (m, 1H), 6.41-6.42 (m, 1H), 6.55-6.59 (m, 3H), 6.93-6.98 (m, 3H), 7.23-7.26 (m, 1H), 7.32 (d, 1H, J = 16.6 Hz), 7.39 (d, 1H, J = 1.6 Hz), 7.42 (d, 1H, J = 8.4 Hz), 7.53 (d, 1H, J = 7.9 Hz), 7.71-7.75 (m, 1H), 8.60-8.62 (m, 1H)
MS (EI) m/z 399 (M⁺).

40-1 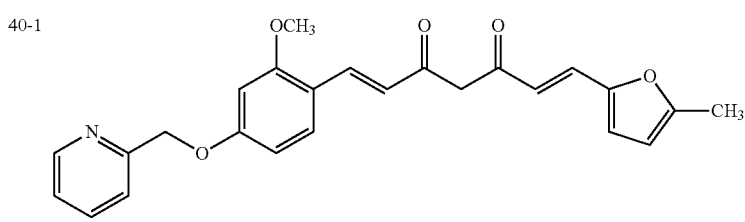

1H NMR (δ, CDCl₃): 2.36 (s, 3H), 3.86 (s, 3H), 5.24 (s, 2H), 5.75 (s, 1H), 6.07-6.09 (m, 1H), 6.43 (d, 1H, J = 15.4 Hz), 6.49-6.50 (m, 1H), 6.57-6.62 (m, 3H), 7.22-7.26 (m, 1H), 7.33 (d, 1H, J = 15.4 Hz), 7.45-7.48 (m, 1H), 7.50 (d, 1H, J = 7.7 Hz), 7.70-7.74 (m, 1H), 7.88 (d, 1H, J = 16.0 Hz), 8.60-8.62 (m, 1H), 16.02 (brs, 1H)
MS (EI) m/z 417 (M⁺).

TABLE 28-continued

40-2

1H NMR (δ, CDCl₃): 2.33 (s, 3H), 3.85 (s, 3H), 5.23 (s, 2H), 5.99-6.01 (m, 1H), 6.24 (d, 1H, J = 3.15 Hz), 6.53 (s, 1H), 6.56-6.59 (m, 2H), 6.79 (d, 1H, J = 16.2 Hz), 6.87 (d, 1H, J = 16.2 Hz), 6.95 (d, 1H, J = 16.6 Hz), 7.21-7.25 (m, 1H), 7.28 (d, 1H, J = 16.6 Hz), 7.43 (d, 1H, J = 8.3 Hz), 7.52 (d, 1H, J = 7.9 Hz), 7.70-7.74 (m, 1H), 8.60-8.62 (m, 1H)
MS (EI) m/z 413 (M⁺).

TABLE 29

41-1

1H NMR (δ, CDCl₃): 1.95 (s, 3H), 2.27 (s, 3H), 3.86 (s, 3H), 5.25 (s, 2H), 5.74 (s, 1H), 6.38-6.42 (m, 2H), 6.57-6.62 (m, 3H), 7.23-7.31 (m, 2H), 7.47 (d, 1H, J = 9.3 Hz), 7.49-7.53 (m, 1H), 7.71-7.75 (m, 1H), 7.88 (d, 1H, J = 16.3 Hz), 8.59-8.63 (m, 1H)
MS (EI) m/z 431 (M⁺).

41-2

1H NMR (δ, CDCl₃): 1.94 (s, 3H), 2.24 (s, 3H), 3.85 (s, 3H), 5.23 (s, 2H), 6.16 (s, 1H), 6.53-6.59 (m, 3H), 6.78 (d, 1H, J = 16.4 Hz), 6.83 (d, 1H, J = 16.4 Hz), 6.96 (d, 1H, J = 16.8 Hz), 7.22-7.26 (m, 1H), 7.30 (d, 1H, J = 16.8 Hz), 7.43 (d, 1H, J = 8.5 Hz), 7.51-7.53 (m, 1H), 7.70-7.74 (m, 1H), 8.60-8.62 (m, 1H)
MS (EI) m/z 427 (M⁺).

42-1

MS (EI) m/z 417 (M⁺).

42-2

1H NMR (δ, CDCl₃): 3.85 (s, 3H), 3.95 (s, 3H), 5.24 (s, 2H), 6.47 (d, 1H, J = 2.0 Hz), 6.57 (dd, 1H, J = 2.4, 8.6 Hz), 6.59 (d, 1H, J = 2.4 Hz), 6.60 (s, 1H), 6.93 (d, 1H, J = 16.7 Hz), 6.97 (d, 1H, J = 16.3 Hz), 7.03 (d, 1H, J = 16.3 Hz), 7.23-7.27 (m, 1H), 7.31

TABLE 29-continued
(d, 1H, J = 16.7 Hz), 7.41 (d, 1H, J = 8.3 Hz), 7.44 (d, 1H, J = 2.0 Hz), 7.51-7.54 (m, 1H), 7.71-7.75 (m, 1H), 8.61-8.63 (m, 1H)
MS (EI) m/z 413 (M⁺).
TABLE 30
43-1
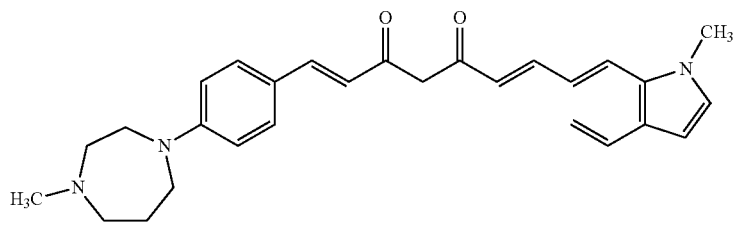 [SMILES: C=Cc1ccn(C)c1/C=C/C=C/C(=O)CC(=O)/C=C/c1ccc(N2CCCN(C)CC2)cc1]
1H NMR (δ, CDCl₃): 2.00-2.06 (m, 2H), 2.39 (s, 3H), 2.55-2.59 (m, 2H), 2.71-2.74 (m, 2H), 3.53-3.56 (m, 2H), 3.61-3.64 (m, 2H), 3.83 (s, 3H), 5.79 (s, 1H), 6.43 (d, 1H, J = 15.5 Hz), 6.48-6.50 (m, 1H), 6.65 (d, 1H, J = 15.8 Hz), 6.67-6.70 (m, 2H), 7.12 (d, 1H, J = 3.1 Hz), 7.37-7.40 (m, 1H), 7.43-7.49 (m, 3H), 7.59-7.64 (m, 2H), 7.80 (d, 1H, J = 15.7 Hz)
MS (EI) m/z 441 (M⁺).
43-2
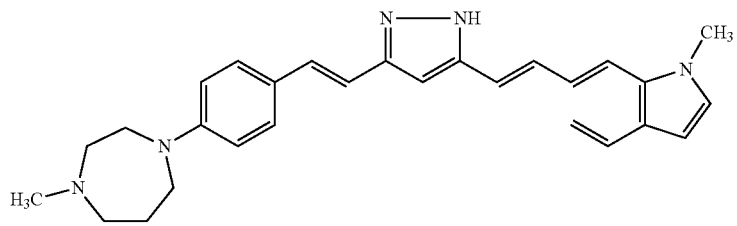 [SMILES: C=Cc1ccn(C)c1/C=C/C=C/c1cc(/C=C/c2ccc(N3CCCN(C)CC3)cc2)n[nH]1]
1H NMR (δ, CDCl₃): 2.01-2.07 (m, 2H), 2.39 (s, 3H), 2.56-2.61 (m, 2H), 2.71-2.75 (m, 2H), 3.51-3.54 (m, 2H), 3.60-3.63 (m, 2H), 3.81 (s, 3H), 6.46-6.48 (m, 1H), 6.59 (s, 1H), 6.66-6.69 (m, 2H), 6.82 (d, 1H, J = 16.5 Hz), 7.00 (d, 1H, J = 16.4 Hz), 7.05-7.10 (m, 2H), 7.23 (d, 1H, J = 16.4 Hz), 7.31-7.34 (m, 1H), 7.36-7.39 (m, 2H), 7.41-7.43 (m, 1H), 7.59 (d, 1H, J = 8.1 Hz)
MS (EI) m/z 437 (M⁺).
44-1
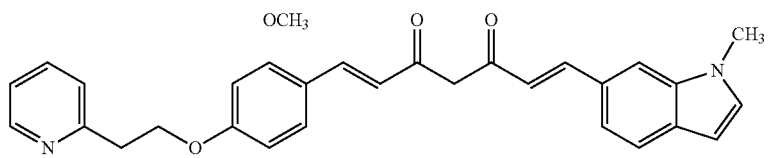
MS (EI) m/z 480 (M⁺).
44-2
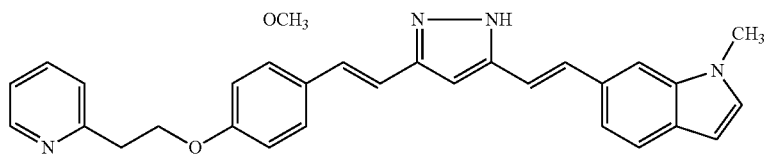
1H-NMR (CDCl₃): δ 3.28 (t, 2H, J = 6.7 Hz), 3.79 (s, 3H), 3.84 (s, 3H), 4.40 (t, 2H, J = 6.7 Hz), 6.45-6.47 (m, 2H), 6.51 (dd, 1H, J = 2.3 Hz, 8.3 Hz), 6.62 (s, 1H), 6.96 (d, 1H, J = 16.5 Hz), 7.05 (d, 1H, J = 3.0 Hz), 7.08 (d, 1H, J = 16.5 Hz), 7.14-7.18 (m, 1H), 7.23 (d, 1H, J = 16.5 Hz), 7.26-7.29 (m, 1H), 7.29-7.33 (m, 2H), 7.40 (brs, 1H), 7.42 (d, 1H, J = 8.6 Hz), 7.58 (d, 1H, J = 8.3 Hz), 7.61-7.65 (m, 1H), 8.56-8.58 (m, 1H)
MS (EI) m/z 476 (M⁺).

TABLE 31
45-1
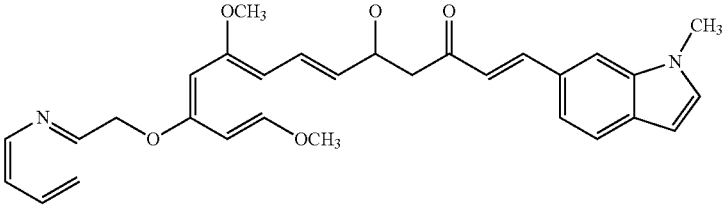 [SMILES: C=C/C=C\N=C\COC(/C=C/OC)=C/C(=C/C=C/C(O)CC(=O)/C=C/c1ccc2ccn(C)c2c1)OC]
1H NMR (δ, CDCl₃): 3.82 (s, 3H), 3.86 (s, 6H), 5.25 (s, 2H), 5.82 (s, 1H), 6.24 (s, 2H), 6.48 (d, 1H, J = 3.2 Hz), 6.66 (d, 1H, J = 15.4 Hz), 7.01 (d, 1H, J = 16.0 Hz), 7.11 (d, 1H, J = 3.2 Hz), 7.23-7.26 (m, 1H), 7.37 (d, 1H, J = 1.3 Hz, 8.4 Hz), 7.47 (s, 1H), 7.52 (d, 1H, J = 7.7 Hz), 7.60 (d, 1H, J = 8.4 Hz), 7.71-7.75 (m, 1H), 7.79 (d, 1H, J = 15.4 Hz), 8.07 (d, 1H, J = 16.0 Hz), 8.60-8.62 (m, 1H), 16.23 (brs, 1H)
MS (EI) m/z 496 (M⁺).
45-2
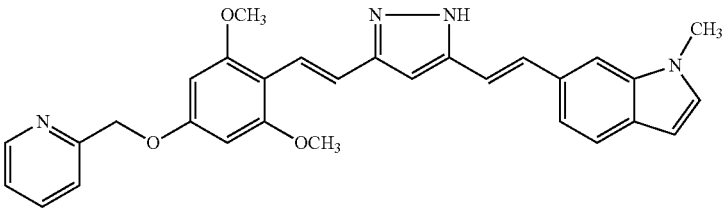 [SMILES: COc1cc(OCc2ccccn2)cc(OC)c1/C=C/c1cc(/C=C/c2ccc3ccn(C)c3c2)[nH]n1]
1H NMR (δ, CDCl₃): 3.79 (s, 3H), 3.85 (s, 6H), 5.24 (s, 2H), 6.26 (s, 2H), 6.45 (d, 1H, J = 3.2 Hz), 6.63 (s, 1H), 7.04 (d, 1H, J = 2.75 Hz), 7.11 (d, 1H, J = 16.1 Hz), 7.22-7.27 (m, 2H), 7.31 (dd, 1H, J = 1.4 Hz, 8.3 Hz), 7.37 (s, 2H), 7.41 (s, 1H), 7.53 (d, 1H, J = 7.75 Hz), 7.57 (d, 1H, J = 8.3 Hz), 7.71-7.75 (m, 1H), 8.60-8.62 (m, 1H)
MS (EI) m/z 492 (M⁺).
46-1
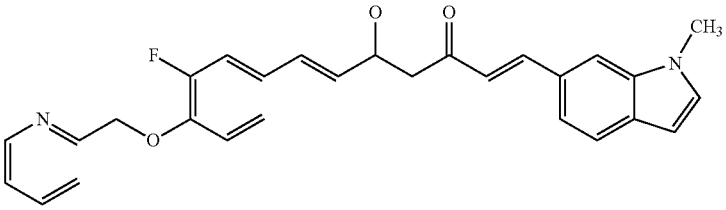 [SMILES: C=C/C=C\N=C\CO/C(C=C)=C(F)/C=C/C=C/C(O)CC(=O)/C=C/c1ccc2ccn(C)c2c1]
MS (EI) m/z 454 (M⁺).
46-2
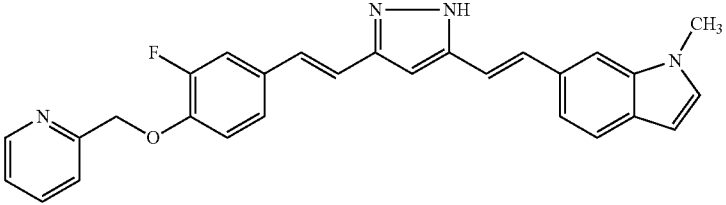 [SMILES: Cn1ccc2ccc(/C=C/c3cc(/C=C/c4ccc(OCc5ccccn5)c(F)c4)n[nH]3)cc21]
MS (EI) m/z 450 (M⁺).
TABLE 32
47-1
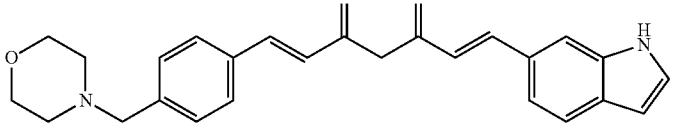
1H NMR (δ, CDCl₃): 2.44-2.48 (m, 4H), 3.52 (s, 2H), 3.70-3.74 (m, 4H), 5.84 (s, 1H), 6.57-6.59 (m, 1H), 6.62 (d, 1H, J = 15.9 Hz), 6.66 (d, 1H, J = 15.8 Hz), 7.29-7.31 (m, 1H), 7.35-7.38 (m, 2H), 7.39-7.42 (m, 1H), 7.50-7.53 (m, 2H), 7.57-7.58 (m, 1H), 7.63-7.67 (m, 2H), 7.81 (d, 1H, J = 15.7 Hz), 8.31 (brs, 1H), 16.03 (brs, 1H)
MS (EI) m/z 414 (M⁺).

TABLE 32-continued

47-2

1H NMR (δ, CDCl₃): 2.44-2.48 (m, 4H), 3.51 (s, 2H), 3.70-3.74 (m, 4H), 6.54-6.55 (m, 1H), 6.63 (s, 1H), 7.03 (d, 1H, J = 16.3 Hz), 7.04 (d, 1H, J = 16.5 Hz), 7.09 (d, 1H, J = 16.5 Hz), 7.20 (d, 1H, J = 16.2 Hz), 7.21-7.23 (m, 1H), 7.30-7.34 (m, 3H), 7.44-7.47 (m, 3H), 7.61 (d, 1H, J = 8.3 Hz), 8.16 (brs, 1H)
MS (EI) m/z 410 (M⁺).

48-1

1H NMR (δ, CDCl₃): 2.49-2.56 (m, 4H), 2.59-2.64 (m, 2H), 2.81-2.86 (m, 2H), 3.72-3.76 (m, 4H), 5.83 (s, 1H), 6.56-6.58 (m, 1H), 6.59 (d, 1H, J = 16.0 Hz), 6.65 (d, 1H, J = 16.0 Hz), 7.24 (d, 2H, J = 8.2 Hz), 7.28-7.30 (m, 1H), 7.39-7.41 (m, 1H), 7.48 (d, 2H, J = 8.2 Hz), 7.57 (s, 1H), 7.61-7.65 (m, 2H), 7.80 (d, 1H, J = 16.0 Hz), 8.30 (brs, 1H), 16.00 (brs, 1H)
MS (EI) m/z 428 (M⁺).

48-2

1H NMR (δ, DMSO-d₆): 2.41-2.44 (m, 4H), 2.49-2.55 (m, 2H), 2.74 (t, 2H, J = 7.7 Hz), 3.56-3.60 (m, 4H), 6.42 (brs, 1H), 6.73 (s, 1H), 6.96-7.39 (m, 8H), 7.43-7.56 (m, 4H), 11.04-11.17 (m, 1H), 12.88 (s, 1H)
MS (EI) m/z 424 (M⁺).

TABLE 33

49-1

1H NMR (δ, CDCl₃): 1.81-1.88 (m, 2H), 2.35-2.51 (m, 6H), 2.68 (t, 2H, J = 7.7 Hz), 3.70-3.77 (m, 4H), 5.83 (s, 1H), 6.57-6.62 (m, 2H), 6.66 (d, 1H, J = 15.9 Hz), 7.20-7.23 (m, 2H), 7.30-7.31 (m, 1H), 7.41 (dd, 1H, J = 1.4, 8.2 Hz), 7.47-7.50 (m, 2H), 7.57-7.58 (m, 1H), 7.62-7.66 (m, 2H), 7.81 (d, 1H, J = 15.9 Hz), 8.32 (brs, 1H)
MS (EI) m/z 442 (M⁺).

49-2

1H NMR (δ, CDCl₃): 1.81-1.88 (m, 2H), 2.39 (t, 2H, J = 7.6 Hz), 2.44-2.49 (m, 4H), 2.65 (t, 2H, J = 7.7 Hz), 3.72-3.76 (m, 4H), 6.54-6.56 (m, 1H), 6.64 (s, 1H), 7.00-7.06 (m, 2H), 7.08 (d, 1H, J = 16.6 Hz), 7.16-7.23 (m, 4H), 7.33 (dd, 1H, J = 1.2, 8.5 Hz), 7.40-7.43 (m, 2H), 7.47-7.48 (m, 1H), 7.61 (d, 1H, J = 8.3 Hz), 8.19 (brs, 1H)
MS (EI) m/z 438 (M⁺).

TABLE 33-continued 50-1

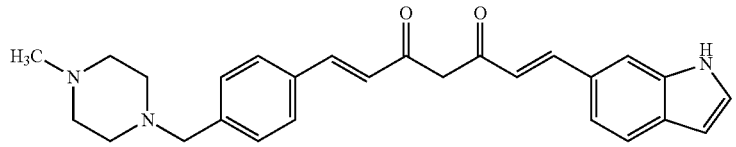 [SMILES: CN1CCN(Cc2ccc(/C=C/C(=O)CC(=O)/C=C/c3ccc4cc[nH]c4c3)cc2)CC1]

1H NMR (δ, CDCl₃): 2.29 (s, 3H), 2.35-2.61 (m, 8H), 3.53 (s, 2H), 5.84 (s, 1H), 6.57-6.59 (m, 1H), 6.61 (d, 1H, J = 15.9 Hz), 6.66 (d, 1H, J = 15.8 Hz), 7.29-7.31 (m, 1H), 7.34-7.37 (m, 2H), 7.40-7.42 (m, 1H), 7.49-7.52 (m, 2H), 7.56-7.58 (m, 1H), 7.64 (d, 1H, J = 8.3 Hz), 7.65 (d, 1H, J = 15.9 Hz), 7.81 (d, 1H, J = 15.7 Hz), 8.33 (brs, 1H), 16.03 (brs, 1H)
MS (EI) m/z 427 (M⁺).

50-2

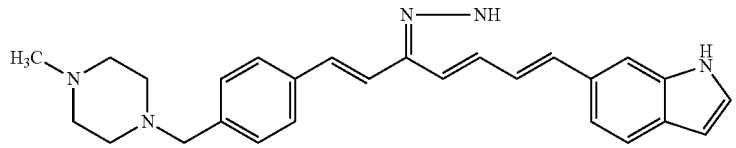 [SMILES: CN1CCN(Cc2ccc(/C=C/C(/C=C/C=C/c3ccc4cc[nH]c4c3)=N/N)cc2)CC1]

1H NMR (δ, CDCl₃): 2.29 (s, 3H), 2.40-2.57 (m, 8H), 3.51 (s, 2H), 6.54-6.56 (m, 1H), 6.63 (s, 1H), 7.02 (d, 1H, J = 16.4 Hz), 7.03 (d, 1H, J = 16.5 Hz), 7.08 (d, 1H, J = 16.5 Hz), 7.19 (d, 1H, J = 16.5 Hz), 7.20-7.23 (m, 1H), 7.29-7.34 (m, 3H), 7.42-7.48 (m, 3H), 7.61 (d, 1H, J = 8.3 Hz), 8.23 (brs, 1H)
MS (EI) m/z 423 (M⁺).

TABLE 34

51-1

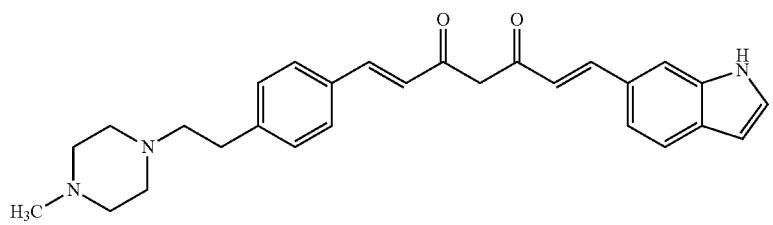 [SMILES: CN1CCN(CCc2ccc(/C=C/C(=O)CC(=O)/C=C/c3ccc4cc[nH]c4c3)cc2)CC1]

1H NMR (δ, CDCl₃): 2.30 (s, 3H), 2.40-2.65 (m, 10H), 2.80-2.85 (m, 2H), 5.83 (s, 1H), 6.56-6.61 (m, 2H), 6.65 (d, 1H, J = 15.9 Hz), 7.23 (d, 2H, J = 8.1 Hz), 7.28-7.30 (m, 1H), 7.40 (dd, 1H, J = 1.5
Hz, 8.05 Hz), 7.47 (d, 2H, J = 8.1 Hz), 7.56 (s, 1H), 7.61-7.65 (m, 2H), 7.80 (d, 1H, J = 15.9 Hz), 8.34 (brs, 1H), 15.96 (brs, 1H)
MS (EI) m/z 441 (M⁺).

51-2

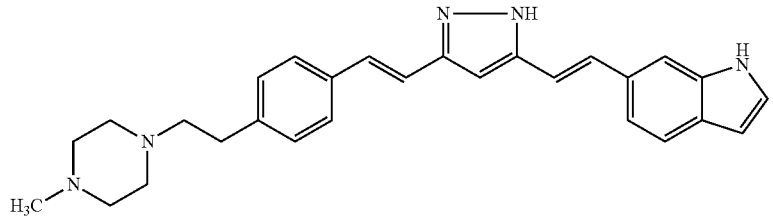 [SMILES: CN1CCN(CCc2ccc(/C=C/c3cc(/C=C/c4ccc5cc[nH]c5c4)[nH]n3)cc2)CC1]

1H NMR (δ, CDCl₃): 2.32 (s, 3H), 2.41-2.69 (m, 10H), 2.78-2.85 (m, 2H), 6.54-6.56 (m, 1H), 6.63 (s, 1H), 7.01 (d, 1H, J = 16.5 Hz), 7.03 (d, 1H, J = 16.4 Hz), 7.07 (d, 1H, J = 16. 5 Hz), 7.16-7.22 (m, 3H), 7.22-7.24 (m, 1H), 7.33 (dd, 1H, J = 1.3 Hz, 8.2 Hz), 7.42 (d, 2H, J = 8.1 Hz), 7.48 (brs, 1H), 7.62 (d, 1H, J = 8.2 Hz), 8.19 (brs, 1H)
MS (EI) m/z 437 (M⁺).

TABLE 34-continued 52-1

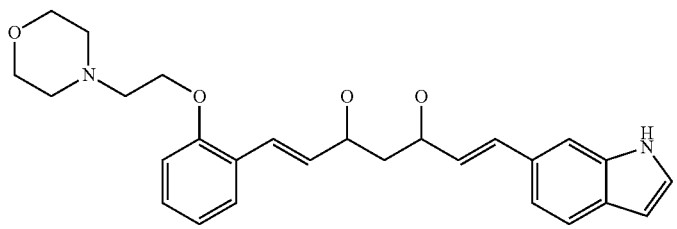 [SMILES: OC(/C=C/c1ccc2cc[nH]c2c1)CC(O)/C=C/c1ccccc1OCCN1CCOCC1]

1H NMR (δ, CDCl₃): 2.63 (t, 4H, J = 4.8 Hz), 2.89 (t, 2H, J = 5.8 Hz), 3.76 (t, 4H, J = 4.8 Hz), 4.20 (t, 2H, J = 5.8 Hz), 5.83 (s, 1H), 6.56-6.58 (m, 1H), 6.65 (d, 1H, J = 16.0 Hz), 6.76 (d, 1H, J = 16.0 Hz), 6.93 (d, 1H, J = 8.0 Hz), 6.96-7.00 (m, 1H), 7.28-7.34 (m, 2H), 7.40 (dd, 1H, J = 1.5 Hz, 8.0 Hz), 7.54-7.58 (m, 2H), 7.64 (d, 1H, J = 8.25 Hz), 7.80 (d, 1H, J = 16.0 Hz), 7.97 (d, 1H, J = 16.0 Hz), 8.31 (brs, 1H), 16.01 (brs, 1H)
MS (EI) m/z 444 (M⁺).

52-2

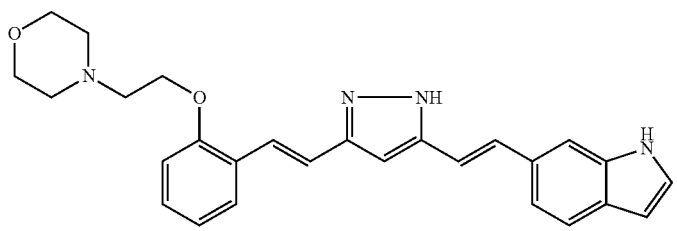 [SMILES: C(=C\c1cc(/C=C/c2ccccc2OCCN2CCOCC2)n[nH]1)/c1ccc2cc[nH]c2c1]

1H NMR (δ, CDCl₃): 2.62 (t, 4H, J = 4.6 Hz), 2.88 (t, 2H, J = 5.8 Hz), 3.75 (t, 4H, J = 4.6 Hz), 4.18 (t, 2H, J = 5.8 Hz), 6.52-6.54 (m, 1H), 6.61 (s, 1H), 6.90 (d, 1H, J = 7.7 Hz), 6.94-6.98 (m, 1H), 7.06 (d, 1H, J = 16.3 Hz), 7.13 (d, 1H, J = 16.7 Hz), 7.18-7.25 (m, 3H), 7.31-7.34 (m, 1H), 7.42-7.47 (m, 2H), 7.55 (dd, 1H, J = 1.6 Hz, 7.7 Hz), 7.60 (d, 1H, J = 8.2 Hz), 8.15 (brs, 1H)
MS (EI) m/z 440 (M⁺).

TABLE 35

53-1

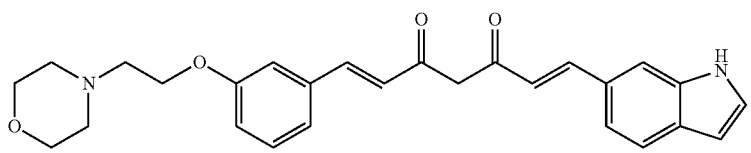 [SMILES: O=C(/C=C/c1cccc(OCCN2CCOCC2)c1)CC(=O)/C=C/c1ccc2cc[nH]c2c1]

1H NMR (δ, CDCl₃): 2.56-2.62 (m, 4H), 2.81-2.84 (m, 2H), 3.72-3.76 (m, 4H), 4.13-4.17 (m, 2H), 5.84 (s, 1H), 6.56-6.59 (m, 1H), 6.60 (d, 1H, J = 15.9 Hz), 6.65 (d, 1H, J = 15.9 Hz), 6.92 (dd, 1H, J = 2.45 Hz, 8.1 Hz), 7.08-7.10 (m, 1H), 7.15 (d, 1H, J = 7.85 Hz), 7.27-7.32 (m, 2H), 7.39-7.42 (m, 1H), 7.57 (s, 1H), 7.60 (d, 1H, J = 15.9 Hz), 7.64 (d, 1H, J = 8.1 Hz), 7.81 (d, 1H, J = 15.9 Hz), 8.32 (brs, 1H), 15.97 (brs, 1H)
MS (EI) m/z 444 (M⁺).

53-2

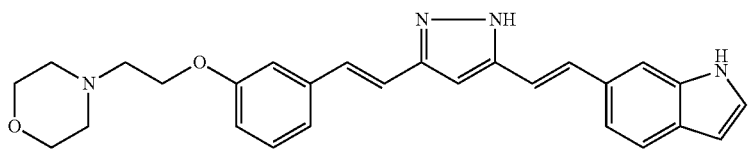 [SMILES: C(=C\c1cc(/C=C/c2ccc3cc[nH]c3c2)[nH]n1)/c1cccc(OCCN2CCOCC2)c1]

1H NMR (δ, CDCl₃): 2.68 (brs, 4H), 2.90 (brs, 2H), 3.79 (brs, 4H), 4.21 (brs, 2H), 6.54-6.56 (m, 1H), 6.63 (s, 1H), 6.82-6.85 (m, 1H), 7.02 (d, 1H, J = 16.3 Hz), 7.04-7.06 (m, 3H), 7.10 (d, 1H, J = 7.7 Hz), 7.19 (d, 1H, J = 16.3 Hz), 7.22-7.24 (m, 1H), 7.25-7.29 (m, 1H), 7.33 (dd, 1H, J = 1.4 Hz, 8.3 Hz), 7.48 (s, 1H), 7.62 (d, 1H, J = 8.3 Hz), 8.19 (brs, 1H)
MS (EI) m/z 440 (M⁺).

TABLE 35-continued

54-1

MS (EI) m/z 466 (M+).

54-2

1H NMR (δ, CDCl₃): 3.29 (t, 2H, J = 6.7 Hz), 3.86 (s, 3H), 4.41 (t, 2H, J = 6.7 Hz), 6.47 (d, 1H, J = 2.3 Hz), 6.52-6.56 (m, 2H), 6.62 (s, 1H), 6.96 (d, 1H, J = 16.5 Hz), 7.05 (d, 1H, J = 16.5 Hz), 7.15-7.23 (m, 3H), 7.24-7.28 (m, 1H), 7.30 (d, 1H, J = 16.5 Hz), 7.33 (dd, 1H, J = 1.4 Hz, 8.3 Hz), 7.43 (d, 1H, J = 8.3 Hz), 7.49 (s, 1H), 7.61 (d, 1H, J = 8.7 Hz), 7.61-7.66 (m, 1H), 8.17 (brs, 1H), 8.56-8.59 (m, 1H)
MS (EI) m/z 462 (M+).

TABLE 36

55-1

1H NMR (δ, CDCl₃): 2.15 (s, 3H), 4.25-4.30 (m, 4H), 5.61 (s, 1H), 6.31 (d, 1H, J = 15.7 Hz), 6.86 (d, 1H, J = 8.3 Hz), 7.02 (dd, 1H, J = 2.0 Hz, 8.3 Hz), 7.05 (d, 1H, J = 2.0 Hz), 7.48 (d, 1H, J = 15.7 Hz), 15.41 (brs, 1H)

55-2

MS (EI) m/z 493 (M+).

55-3

1H NMR (δ, CDCl₃): 2.58-2.61 (m, 4H), 2.81 (t, 2H, J = 5.7 Hz), 3.73-3.76 (m, 4H), 3.86 (s, 3H), 4.14 (t, 2H, J = 5.7 Hz), 4.26-4.27 (m, 4H), 6.48-6.51 (m, 2H), 6.58 (s, 1H), 6.84 (d, 1H, J = 8.3 Hz), 6.89 (d, 1H, J = 16.5 Hz), 6.93-6.99 (m, 3H), 7.01 (d, 1H, J = 1.8 Hz), 7.29 (d, 1H, J = 16.5 Hz), 7.43 (d, 1H, J = 8.7 Hz)
MS (EI) m/z 489 (M+).

56-1

1H NMR (δ, CDCl₃): 2.56-2.60 (m, 8H), 2.81 (t, 4H, J = 5.7 Hz), 3.72-3.75 (m, 8H), 3.88 (s, 6H), 4.15 (t, 4H, J = 5.7 Hz), 5.79 (s, 1H), 6.48 (d, 2H, J = 2.5 Hz), 6.51 (dd, 2H, J = 2.5 Hz, 8.5 Hz), 6.62 (d, 2H, J = 16.0 Hz), 7.47 (d, 2H, J = 8.5 Hz), 7.77 (d, 2H, J = 16.0 Hz), 16.13 (brs, 1H).
MS (EI) m/z 594 (M+).

TABLE 36-continued
56-2 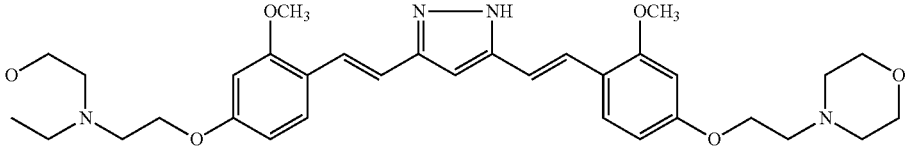 [SMILES: CCN(CCO)CCOc1ccc(/C=C/c2cc(/C=C/c3ccc(OCCN4CCOCC4)cc3OC)[nH]n2)c(OC)c1]
1H NMR (δ, CDCl₃): 2.57-2.61 (m, 8H), 2.81 (t, 4H, J = 5.7 Hz), 3.73-3.76 (m, 8H), 3.86 (s, 6H), 4.14 (t, 4H, J = 5.7 Hz), 6.47-6.52 (m, 4H), 6.61 (s, 1H), 6.97 (d, 2H, J = 16.5 Hz), 7.30 (d, 2H, J = 16.5 Hz), 7.44 (d, 2H, J = 8.3 Hz)
MS (EI) m/z 590 (M⁺).
TABLE 37
57-1 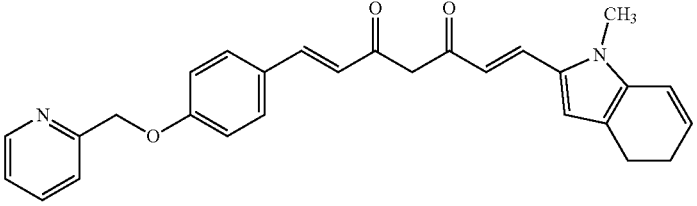 [SMILES: Cn1c(/C=C/C(=O)CC(=O)/C=C/c2ccc(OCc3ccccn3)cc2)cc2c1C=CCC2]
MS (EI) m/z 436 (M⁺).
57-2 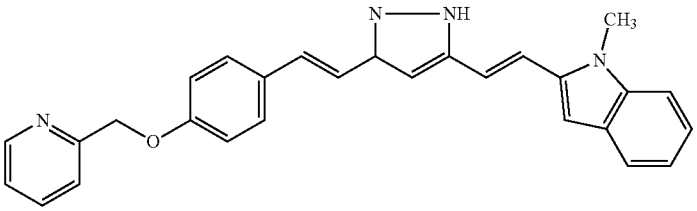 [SMILES: Cn1c(/C=C/C2=CC(/C=C/c3ccc(OCc4ccccn4)cc3)NN2)cc2ccccc21]
1H NMR (δ, CDCl₃): 3.81 (s, 3H), 5.23 (s, 2H), 6.62 (s, 1H), 6.80 (s, 1H), 6.89 (d, 1H, J = 16.4 Hz), 6.97 (d, 2H, J = 8.7 Hz), 7.04 (d, 1H, J = 16.4 Hz), 7.07-7.12 (m, 1H), 7.10 (d, 1H, J = 16.3 Hz), 7.17 (d, 1H, J = 16.3 Hz), 7.18-7.30 (m, 3H), 7.41 (d, 2H, J = 8.7 Hz), 7.52 (d, 1H, J = 7.9 Hz), 7.58 (d, 1H, J = 7.8 Hz), 7.70-7.74 (m, 1H), 8.61 (d, 1H, J = 4.4 Hz)
MS (EI) m/z 432 (M⁺).
58-1 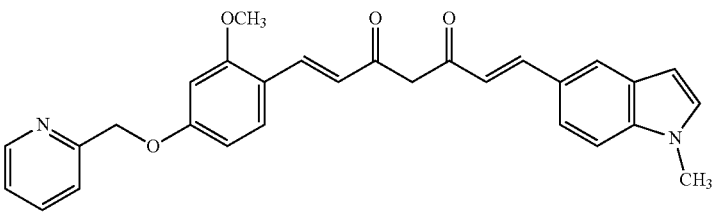 [SMILES: COc1cc(OCc2ccccn2)ccc1/C=C/C(=O)CC(=O)/C=C/c1ccc2c(ccn2C)c1]
MS (EI) m/z 466 (M⁺).
58-2 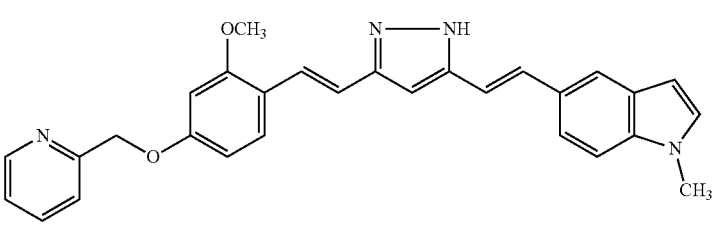 [SMILES: COc1cc(OCc2ccccn2)ccc1/C=C/c1cc(/C=C/c2ccc3c(ccn3C)c2)[nH]n1]
1H NMR (δ, Acetone-d₆): 3.84 (s, 3H), 3.91 (s, 3H), 5.23 (s, 2H), 6.44-6.46 (m, 1H), 6.65-6.68 (m, 2H), 6.74 (d, 1H, J = 2.3 Hz), 7.04-7.09 (m, 2H), 7.21 (d, 1H, J = 3.2 Hz), 7.29-7.34 (m, 2H), 7.36-7.41 (m, 2H), 7.46 (dd, 1H, J = 1.4, 8.7 Hz), 7.53 (d, 1H, J = 8.3 Hz), 7.56-7.58 (m, 1H), 7.70-7.72 (m, 1H), 7.80-7.84 (m, 1H), 8.58-8.60 (m, 1H), 11.93 (brs, 1H)
MS (EI) m/z 462 (M⁺).

TABLE 38

59-1

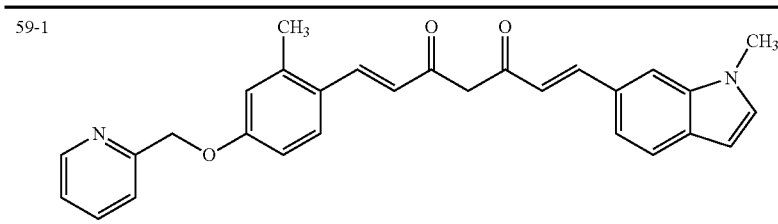

1H NMR (δ, CDCl₃): 2.45 (s, 3H), 3.83 (s, 3H), 5.23 (s, 2H), 5.82 (s, 1H), 6.45-6.50 (m, 2H), 6.67 (d, 1H, J = 15.8 Hz), 6.84-6.87 (m, 2H), 7.13 (d, 1H, J = 3.0 Hz), 7.22-7.27 (m, 1H), 7.37-7.40 (m, 1H), 7.48-7.52 (m, 2H), 7.56-7.63 (m, 2H), 7.70-7.74 (m, 1H), 7.83 (d, 1H, J = 15.8 Hz), 7.89 (d, 1H, J = 15.8 Hz), 8.60-8.62 (m, 1H)
MS (EI) m/z 450 (M⁺).

59-2

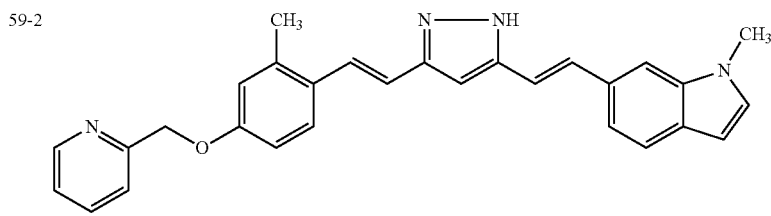

1H NMR (δ, CDCl₃): 2.41 (s, 3H), 3.80 (s, 3H), 5.22 (s, 2H), 6.46-6.48 (m, 1H), 6.63 (s, 1H), 6.82-6.87 (m, 3H), 7.06 (d, 1H, J = 3.1 Hz), 7.07 (d, 1H, J = 16.5 Hz), 7.21-7.28 (m, 3H), 7.31-7.33 (m, 1H), 7.40-7.42 (m, 1H), 7.50-7.54 (m, 2H), 7.59 (d, 1H, J = 8.2 Hz), 7.70-7.74 (m, 1H), 8.60-8.62 (m, 1H)
MS (EI) m/z 446 (M⁺).

Pharmacological Test Example 1: Determination of Tau Aggregation Inhibitory Activity Recombinant three-repeat microtubule-binding domain (3R-MBD) of tau protein was expressed in *E. coli* and was purified and used for the experiment. The purified tau solution was diluted with a 50 mM Tris-HCl buffer (pH 7.6) to a final concentration of 10 μM. The test compounds were prepared using dimethylsulfoxide (hereinafter also referred to as DMSO) at 20-fold of their final concentrations and added to the tau solution so that the DMSO concentration would be 5%. To this solution, heparin was added so that the final concentration would be 10 μM and the plate was left to stand at 37° C. for 16 hours. Thioflavin T was added to the plate so that the concentration would be 10 μM and the fluorescence intensity was measured with a fluorescence plate reader (PerkinElmer, Inc.) (excitation wavelength: 440 nm; fluorescence wavelength: 486 nm).

The final concentration of each compound at the time of measurement was set at 0.1, 0.3, 1, 3, and 10 μM. The sample to which only DMSO was added was used as a negative control and its fluorescence intensity was taken as 0% inhibitory activity to determine the 50% inhibitory concentration (IC₅₀) of each compound. The results are shown in Table 39. Table 39 also shows the calculated maximum inhibition (%) of the compounds that exhibited particularly high maximum inhibition (%) at the concentrations used for the determination of the tau aggregation inhibitory activity.

TABLE 39

| Compound | IC₅₀ (μM) | Maximum inhibition (%) |
|---|---|---|
| Example 16-2 | 0.6 | — |
| Example 17-2 | 0.65 | — |

TABLE 39-continued

| Compound | IC₅₀ (μM) | Maximum inhibition (%) |
|---|---|---|
| Example 19-4 | 0.51 | — |
| Example 20-3 | 0.55 | 89 |
| Example 21-2 | — | 89 |
| Example 22-2 | 0.66 | 90 |
| Example 23-2 | 0.59 | 92 |
| Example 25-2 | 0.84 | — |
| Example 27-3 | — | 91 |
| Example 28-2 | — | 93 |
| Example 32-5 | 0.64 | 90 |
| Example 42-2 | 0.83 | — |
| Example 43-2 | — | 92 |
| Example 53-2 | 0.84 | — |

As is apparent from Table 39, some of the compounds of the present invention exhibited a particularly high tau aggregation inhibitory activity. The compounds that exhibited high maximum inhibition are expected to have improved therapeutic effects and are thus more preferred.

Pharmacological Test Example 2: Determination of β-Secretase Inhibitory Activity The β-secretase inhibitory activity was measured with BACE-1 FRET assay Kit (Invitrogen). The test compounds were prepared using DMSO at 30-fold of their final concentrations and added to an assay buffer so that the DMSO concentration would be 10%. To each of the solutions, equal volumes of a human recombinant β-secretase (1 U/mL) and a fluorescent substrate peptide (750 nM), each dissolved in an assay buffer, were added and the solutions were left to stand for 1 hour. The fluorescence intensity was measured with a fluorescence plate reader (excitation wavelength: 545 nm; fluorescence wavelength: 590 nm).

The final concentration of each compound at the time of measurement was set at 0.1, 0.3, 1, 3, and 10 μM, at 0.3, 1, 3, 10, and 30 µM, or at 1, 3, 10, 30, and 100 µM. The sample to which only DMSO was added was used as a negative control and its fluorescence intensity was taken as 0% inhibitory activity to determine the 50% inhibitory concentration ($IC_{50}$) of each compound for the evaluation of β-secretase inhibitory activity of each compound. The fluorescent substrate peptide had the amino acid sequence of Ser-Glu-Val-Asn-Leu-Asp-Ala-Glu-Lys-Arg, in which the Ser residue at position 1 was labeled with a fluorescent donor (Cy3) and the Lys at position 9 was labeled with a fluorescence quencher (Cy5Q).

The compounds of the present invention exhibited a high β-secretase inhibitory activity.

Pharmacological Test Example 3: Determination of Aβ Aggregation Inhibitory Activity Aβ 1-42 (Peptide Institute, Inc.) was dissolved in 0.1% ammonia water so that the concentration would be 0.5 mM, and then diluted with PBS to 20 µM. The test compounds were prepared using DMSO at 100-fold of their final concentrations and then diluted with PBS so that the DMSO concentration would be 2%. The Aβ solution and each of the test compound solutions were mixed at an equivalent ratio and the mixtures were left to stand at 37° C. for 24 hours. To each of the mixtures, an equal volume of a thioflavin T solution adjusted with a 100 mM Tris-glycine buffer (pH 8.5) to 6 µM was added. The fluorescence intensity was measured with a fluorescence plate reader (excitation wavelength: 440 nm; fluorescence wavelength: 486 nm).

The final concentration of each compound at the time of measurement was set at 0.1, 0.3, 1, 3, and 10 µM or at 2, 4, 8, and 16 µM. The sample to which only DMSO was added was used as a negative control and its fluorescence intensity was taken as 0% inhibitory activity. With the use of the fluorescence intensity of the control taken as 0% inhibitory activity, the 50% inhibitory concentration ($IC_{50}$) of each compound was calculated to evaluate the Aβ aggregation inhibitory activity of each compound.

The compounds of the present invention exhibited a high Aβ aggregation inhibitory activity.

Pharmacological Test Example 4: Concentration Measurement in Brain after Oral Administration Each of the compounds of the present invention shown in Tables 40 and 41 and the compound of Example 2 of JP 2012-229208 A was orally administered to ICR mice (male, 7 weeks old) in a single dose of 5 mg/kg. At 3, 6 and 9 hours after the administration, 1, 3, 6 and 9 hours after the administration, or 1, 3, 6, 9 and 24 hours after the administration, the mice were subjected to perfusion by infusing physiological saline into the heart under inhalational anesthesia with isoflurane, and the whole brain was harvested. Physiological saline was added to the harvested brain in an amount equal to twice the wet weight of the brain and the brain was homogenized. Then, an equal volume of methanol was added thereto, and the mixture was deproteinized. The concentration of each compound in the sample was measured by LC/MS/MS. The test results are shown in Tables 40 and 41.

TABLE 40

| Compound | $AUC_{0-9\ h}$ in brain (ng · hr/g-tissue) |
|---|---|
| Example 22-2 | 458 |
| Example 44-2 | 869 |
| JP 2012-229208 A, Example 2 | 224 |

TABLE 41

| Compound | $AUC_{0-24\ h}$ in brain (ng · hr/g-tissue) |
|---|---|
| Example 14-2 | 24639 |
| Example 18-2 | 9781 |
| Example 19-4 | 3499 |
| Example 20-3 | 5306 |
| Example 27-3 | 1302 |
| JP 2012-229208 A, Example 2 | 645 to 677 |

INDUSTRIAL APPLICABILITY

The compound of the present invention is useful as a prophylactic drug, a therapeutic drug, and the like for Alzheimer's disease and therefore the present invention can be applied to industrial fields such as pharmaceutical industry.

The invention claimed is:
1. A method for treating a disease in which tau, β-secretase or Aβ is involved, the method comprising the step of administering the compound represented by the following general formula (I):

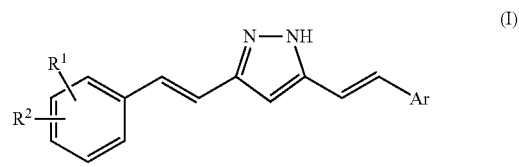

[wherein
R¹ represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, or a carbamoyl group optionally having one or more substituents;
R² represents a group represented by the following general formula (II):

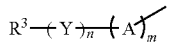

(wherein m and n each represent an integer of 0 or 1,
A represents —O—, —NH—, —S—, —SO— or —SO$_2$—,
Y represents a $C_{1-6}$ alkylene group, a $C_{2-6}$ alkenylene group or a $C_{2-6}$ alkynylene group, and
$R^3$ represents a nitrogen-containing heterocyclic group optionally having one or more substituents, a methoxy group having one or more substituents, a $C_{2-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents);
$R^1$ and $R^2$ may be joined to form a ring together with the benzene ring; and
Ar represents a homocyclic or heterocyclic group optionally having one or more substituents],
or a salt thereof.

2. The method according to claim 1, wherein m is 1 and A is —O—.

3. The method according to claim 2, wherein $R^2$ is a morpholinomethoxy group, a morpholinoethoxy group, a pyridylmethoxy group, a pyridylethoxy group, a 2-pyrrolidinoethoxy group, a 2-piperidinoethoxy group, a 2-(4-(substituted)piperazino)ethoxy group, or a 2-(1,1-dioxo-1,4-thiazinan-4-yl)ethoxy group.

4. The method according to claim 3, wherein $R^2$ is a morpholinoethoxy group.

5. The method according to claim 1, wherein $R^2$ is a morpholinomethyl group, a (4-(substituted)piperazino)methyl group, a (1,1-dioxo-1,4-thiazinan-4-yl)methyl group, a piperidinomethyl group, a pyrrolidinomethyl group, a 2-morpholinoethyl group, a 2-(4-(substituted)piperazino)ethyl group, a 2-(1,1-dioxo-1,4-thiazinan-4-yl)ethyl group, a 2-piperidinoethyl group, a 2-pyrrolidinoethyl group, or a 2-morpholinoethanesulfonyl group.

6. The method according to claim 1, wherein $R^2$ is a 4-(substituted)piperazino group or a 4-(substituted)-1,4-diazepano group, with the exception of the case where Ar is a homocyclic group optionally having a substituent.

7. The method according to claim 1, wherein Ar is a bicyclic group having a benzene skeleton and optionally having one or more substituents.

8. The method according to claim 7, wherein the bicyclic group having a benzene skeleton is a 1,3-benzodioxole group, a 1,4-benzodioxan-5-yl group, a 1,4-benzodioxan-6-yl group, a 1,4-benzodioxin-2-yl group, a quinolino group, or an indolyl group.

9. The method according to claim 1, wherein Ar is a phenyl group optionally having one or more substituents, a pyrrolyl group optionally having one or more substituents, a pyridyl group optionally having one or more substituents, a pyrazyl group optionally having one or more substituents, an imidazolyl group optionally having one or more substituents, or a furyl group optionally having one or more substituents.

10. The method according to claim 6 or a salt thereof, wherein Ar is a pyrrolyl group optionally having one or more substituents, a pyridyl group optionally having one or more substituents, a pyrazyl group optionally having one or more substituents, an imidazolyl group optionally having one or more substituents, or a furyl group optionally having one or more substituents.

11. The method according to claim 1, wherein Ar is represented by the following general formula (III):

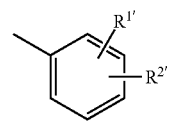

(wherein
$R^{1'}$ represents a hydrogen atom, a halogen atom, a hydroxy group, a nitro group, an amino group, a cyano group, a $C_{1-6}$ alkyl group optionally having one or more substituents, a $C_{1-6}$ alkoxy group optionally having one or more substituents, a mono- or di($C_{1-6}$ alkyl)amino group optionally having one or more substituents, a $C_{1-6}$ alkylthio group optionally having one or more substituents, a $C_{1-6}$ alkylsulfonyl group optionally having one or more substituents, a $C_{1-6}$ acyl group optionally having one or more substituents, a $C_{1-6}$ acylamino group optionally having one or more substituents, a $C_{2-6}$ alkenyl group optionally having one or more substituents, a $C_{2-6}$ alkenyloxy group optionally having one or more substituents, a mono- or di($C_{2-6}$ alkenyl)amino group optionally having one or more substituents, a $C_{2-6}$ alkenylthio group optionally having one or more substituents, or a carbamoyl group optionally having one or more substituents;
$R^{2'}$ represents a group represented by the following general formula (IV):

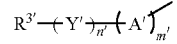

(wherein m' and n' each represent an integer of 0 or 1,
A' represents —O—, —NH—, —S—, —SO— or —SO$_2$—,
Y' represents a $C_{1-6}$ alkylene group, a $C_{2-6}$ alkenylene group or a $C_{2-6}$ alkynylene group, and
$R^{3'}$ represents a nitrogen-containing heterocyclic group optionally having one or more substituents, a $C_{1-6}$ alkoxy group optionally having one or more substituents, a mono- or di($C_{1-6}$ alkyl)amino group optionally having one or more substituents, a mono- or di($C_{2-6}$ alkenyl)amino group optionally having one or more substituents, or a carbamoyl group optionally having one or more substituents), and
$R^{1'}$ and $R^{2'}$ may form a ring together with the benzene ring).

12. The method of claim 1 wherein the disease is Alzheimer's disease.

* * * * *